US006905670B2

(12) United States Patent  
Ausubel et al.

(10) Patent No.: US 6,905,670 B2  
(45) Date of Patent: Jun. 14, 2005

(54) METHODS OF SCREENING COMPOUNDS USEFUL FOR PREVENTION OF INFECTION OR PATHOGENICITY

(75) Inventors: Frederick M. Ausubel, Newton, MA (US); Stephen B. Calderwood, Wellesley, MA (US); Eleftherios Mylonakis, Boston, MA (US); Andrew Diener, Cambridge, MA (US); Julia Plotnikova, Quincy, MA (US); Costi D. Sifri, Quincy, MA (US); Laurence G. Rahme, Brookline, MA (US); Man-Wah Tan, Somerville, MA (US); Gary B. Ruvkun, Newton, MA (US); Georg Jander, Ithaca, NY (US); Jacqueline Heard, San Mateo, CA (US)

(73) Assignee: The General Hospital Corporation, Boston, MA (US)

( * ) Notice: Subject to any disclaimer, the term of this patent is extended or adjusted under 35 U.S.C. 154(b) by 156 days.

(21) Appl. No.: 10/153,754

(22) Filed: May 22, 2002

(65) Prior Publication Data

US 2003/0086871 A1 May 8, 2003

Related U.S. Application Data

(63) Continuation-in-part of application No. 08/962,750, filed on Nov. 3, 1997, which is a continuation-in-part of application No. 08/852,927, filed on May 8, 1997, now abandoned, which is a continuation-in-part of application No. 08/411,560, filed on Mar. 28, 1995, now Pat. No. 6,461,854.

(51) Int. Cl.$^7$ .................. A61K 49/00; A01N 63/00; A01N 63/04

(52) U.S. Cl. ............ 424/9.1; 424/93.1; 424/93.2; 424/93.5; 424/234.1; 435/4; 435/4.2; 435/243; 435/254.1; 435/254.11; 435/440; 536/23.1; 536/23.24

(58) Field of Search .................. 424/9.1, 93.1, 424/93.2, 93.5, 234.1; 435/4, 4.2, 440, 243, 254.1, 254.11; 536/23.1, 23.24

(56) References Cited

U.S. PATENT DOCUMENTS

| 4,713,378 | A | 12/1987 | Perrone et al. |
| 5,270,448 | A | 12/1993 | Payne |
| 5,366,995 | A | 11/1994 | Savage et al. |
| 5,853,998 | A | 12/1998 | Ohno et al. |
| 6,461,854 | B1 | * 10/2002 | Ausubel et al. .......... 435/252.3 |

FOREIGN PATENT DOCUMENTS

| WO | WO 94/16077 | 7/1994 |
| WO | WO 95/11969 | 5/1995 |
| WO | WO 96/30053 | 10/1996 |
| WO | WO 98/12205 | 3/1998 |
| WO | WO 98/20157 | 5/1998 |
| WO | WO 98/50080 | 11/1998 |
| WO | WO 98/50554 | 11/1998 |
| WO | WO 99/18996 | 4/1999 |

OTHER PUBLICATIONS

Alexander et al., "Surgical Infections and Choice of Antibiotics" *Surgical Infections*, 13:221–236 W.B. Saunders (ed) Philadelphia, PA (1991).

Bent et al., "RPS2 of *Arabidopsis thaliana:* A Leucine–Rich Repeat Class of Plant Disease Resistance Genes," *Science* 265:1856–1860 (1994).

Berka and Vasil, "Phospholipase C (Heat–Labile Hemolysin) of *Pseudomonas aeruginosa:* Purification and Preliminary Characterization," *Journal of Bacteriology* 152:239–245 (1982).

Bestwick et al., "Localization of Hydrogen Peroxide Accumulation during the Hypersensitive Reaction of Lettuce Cells to *Pseudomonas syringae* pv *phaseolicola,*" *The Plant Cell* 9:209–221 (1997).

Bucher, "Pathogens of Tobacco and Tomato Hornworms," *Journal of Invertebrate Pathology* 9:82–89 (1967).

Bulla et al., "Bacteria as Insect Pathogens," *Annu. Rev. Microb.* 29:163–190 (1975).

Chadwick et al., "Adherence Patterns and Virulence for *Galleria mellonella* Larvae of Isolates of *Serratia marcescens,*" *Journal of Invertebrate Pathology* 55:133–134 (1990).

Chadwick et al., "Serological Responses of Insects," *Federation Proceedings* 26:1675–1679 (1967).

Charpentier et al., "The Bacterial Flora of the Midgut of Two Danish Populations of Healthy Fifth Instar Larvae of the Turnip Moth, *Scotia segetum,*" *Journal of Invertebrate Pathology* 32:59–63 (1978).

Cho et al., "Ornamental Plants as Carriers of *Pseudomonas aeruginosa,*" *Phytopathology* 65:425–431 (1975).

Cohen et al., "The Effect of Amiloride on Pigment Expression in a Clinical Isolate of *Pseudomonas Aeruginosa,*" *Current Therapeutic Research* 51:562–567 (1992).

Conrad et al., "Efficacy of Aztreonam in the Treatment of Skeletal Infections Due to *Pseudomonas aeruginosa,*" *Review of Infectious Research* 13:S634–S639 (1991).

Debener et al., "Identification and molecular mapping of a single *Arabidopsis thalianan* locus determining resistance to a phytopathogenic *Pseudomonas syringae* isolate," *The Plant Journal* 1:289–302 (1991).

Dong et al., "Induction of Arabidopsis Defense Genes by Virulent and Avirulent *Pseudomonas syringae* Strains and by a Cloned Avirulence Gene," *The Plant Cell* 3:61–72 (1991).

(Continued)

*Primary Examiner*—Rodney P Swartz  
(74) *Attorney, Agent, or Firm*—Clark & Elbing, LLP

(57) ABSTRACT

Screening procedures are disclosed for identifying compounds useful for inhibiting fungal infection or pathogenicity. Methods are also disclosed for identifying fungal pathogenic virulence factors.

13 Claims, 27 Drawing Sheets

(1 of 27 Drawing Sheet(s) Filed in Color)

OTHER PUBLICATIONS

Dunphy et al., "Octopamine, a Modulator of the Haemocytic Nodulation Response of Non–immune *Galleria mellonella* Larvae," *J. Insect Physiol.* 40:267–272 (1994).

Dunphy, "Interaction of mutants of *Xenorhabdus nematophilus* (*Enterobacteriaceae*) with antibacterial systems, of *Galleria mellonella* larvae (Insecta: Pyralidae)," *Can. J. Microbiol.* 40:161–168 (1994).

Elrod et al., "A Phytopathogenic Bacterium Fatal to Laboratory Animals," *Science* 94:520–521 (1941).

Elrod et al., "*Pseudomonas Aeruginosa*; Its Role As Plant Pathogen," *Journal of Bacteriology* 46: 633–645 (1942).

Fenselau et al., "Determinants of Pathogenicity in *Xanthomonas campestris* pv. *vesicatoria* are Related to Proteins Involved in Secretion in Bacterial Pathogens of Animals," *Molecular Plant–Microbe Interactions* 5:390–396 (1992).

Finlay et al., "Common Themes in Microbial Pathogenicity Revisited," *Microbiology and Molecular Biology Reviews* 61:136–169 (1997).

Fuqua et al., "Quorum Sensing in Bacteria: the LuxR–LuxI Family of Cell Density–Responsive Transcriptional Regulators," *Journal of Bacteriology* 176:269–275 (1994).

Geels, "*Pseudomonas tolaasii* control by Kasugamycin in Cultivated Mushrooms (*Agaricus bisporus,*)" *Journal of Applied Bacteriology* 79:38–42 (1995).

Gingrich, "Acquired Humoral Immune Response of the Large Milkweed Bug, *Oncopeltus Fasciatus* (Dallas), To Injected Materials," *J. Ins. Physiol.* 10:179–194 (1964).

Glazebrook et al., "Isolation of Arabidopsis Mutants with Enhanced Disease Susceptibility by Direct Screening," *Genetics* 143:973–982 (1996).

Gough et al., "hrp Genes of *Pseudomonas solanacearum* are Homologous to Pathogenicity Determinants of Animal Pathogenic Bacteria and are Conserved Among Plant Pathogenic Bacteria," *Molecular Plant–Microbe Interactions* 5:384–389 (1992).

Green et al., "Agricultural Plants and Soil as a Reservoir for *Pseudomonas aeruginosa,*" *Applied Microbiology* 28:987–991 (1974).

Grewal et al., "Effects of Bacteria isolated from a Saprophagous Rhabditid Nematode *Caenorhabditis Elegans* on the Mycelial growth of *Agaricus bisporus,*" *J. Applied Bacteriology* 72:173–179 (1992).

Hacker et al., "Pathogenicity Islands of Virulent Bacteria: Structure, Function and Impact on Microbial Evolution," *Molecular Microbiology* 23:1089–1097 (1997).

Harshey et al., "Spinning tails: Homologies among Bacterial Flagellar Systems," *Trends in Microbiology* 4:226–231 (1996).

Hoffmann et al., "Insect Immunity: *Galleria Mellonella* And Other Lepidoptera Have Cecropia–P9–Like Factors Active Against Gram Negative Bacteria," *Insect Biochem* 11:537–548 (1981).

Holloway, "Genetic Recombination in *Pseudomonas aeruginosa,*" *J. Gen. Microbiol.* 13:572–581 (1955).

Huang et al., "Characterization of the *Pseudomonas syringae* pv. *syringae* 61 hrpJ and hrpI Genes: Homology of HrpI to a Superfamily of Proteins Associated with Protein Translocation," *Molecular Plant–Microbe Interactions* 6:515–520 (1993).

Huang et al., "The *Pseudomonas syringae* pv. syringae 61 hrpH Product, and Envelope Protein Required for Elicitation of the Hypersensitive Response in Plants," *Journal of Bacteriology* 174:6878–6885 (1992).

Iglewski et al., "NAD–Dependent Inhibition of Protein Synthesis by *Pseudomonas aeruginosa* Toxin," *Proc. Nat. Acad. Sci. USA* 72:2284–2288 (1975).

Ishimoto et al., "Formation of Pilin in *Pseudomonas aeruginosa* Requires the Alternative σ factor (RpoN) of RNA Polymerase," *Proc. Nat. Acad. Sci. USA* 86:1954–1957 (1989).

Jarosz, "Interaction of *Pseudomonas aeruginosa* proteinase with the Inducible Non–Self Response System of Insects," *Cytobios* 83:71–84 (1995).

Johnston et al., "Transcriptional Activation of *Salmonella typhimurium* Invasion Genes by a Member of the Phosphorylated Response–Regulator Superfamily," *Molecular Microbiology* 22:715–727 (1996).

Kamon et al., "Immune Response of Locusts to Venom of the Scorpion," *Journal of Invertebrate Pathology* 7:192–198 (1965).

Kanost et al., "Isolation and Characterization of a Hemocyte Aggregation Inhibitor From Hemolymph of *Manduca sexta* Larvae," *Archives of Insect Biochemistry and Physiology* 27:123–136 (1994).

Kaska, "The Toxicity of Extracellular Proteases of the Bacterium *Serratia marcescens* for Larvae of Greater Wax Moth, *Galleria mellonella,*" *Journal of Invertebrate Pathology* 27:271 (1976).

Kominos et al., "Introduction of *Pseudomonas aeruginosa* into a Hospital via Vegetables," *Applied Microbiology* 24:567–570 (1972).

Kovalchik et al., "*Neisseria gonorrhoeae:* Colonial Morphology of Rectal Isolates," *Applied Microbiology* 23:986–989 (1972).

Kunkel et al., "RPS2, an Arabidopsis Disease Resistance Locus Specifying Recognition of *Pseudomonas syringae* Strains Expressing the Avirulence Gene avrRpt2," *The Plant Cell* 5:865–875 (1993).

Laville et al., "Global Control in *Pseudomonas fluorescens* Mediating Antibiotic Synthesis and Suppression of Black Root Rot of Tobacco," *Proc. Natl. Acad. Sci. USA* 89:1562–1566 (1992).

Lee, "Type III Secretion Systems: Machines to Deliver Bacterial Proteins into Eukaryotic Cells?," *Trends Microbiol.* 5:148–156 (1997).

Lemaitre et al., "The Dorsoventral Regulatory Gene Cassette *spätzle/Toll/cactus* Controls the Potent Antifungal Response in Drosophila Adults," *Cell* 86:973–983 (1996).

Lysenko, "Pseudomonas–An Attempt at a General Classification," *J. Gen. Microbiol.* 25:379–408 (1961).

Lysenko, "The Mechanisms of Pathogenicity of *Pseudomonas aeruginosa* (Schroeter) Migula I. The Pathogenicity of Strain N–06 for Larvae of the Greater Wax Moth, *Galleria mellonella* (Linnaeus)," *Journal of Insect Pathology* 5:78–82 (1963).

Lysenko, "The Mechanisms of Pathogenicity of *Pseudomonas aeruginosa* (Schroeter) Migula II. A Toxic Substance Produced in Filtrates of Cultures," *Journal of Insect Pathology* 5:83–88 (1963).

Lysenko, "The Mechanisms of Pathogenicity of *Pseudomonas aeruginosa* (Schroeter) Migula III. The Effect of N–06 Toxin on the Oxygen Consumption of *Galleria Prepupae,*" *Journal of Insect Pathology* 5:89–93 (1963).

Lysenko, "The Mechanisms of Pathogenicity of *Pseudomonas aeruginosa* (Schroeter) Migula IV. The Antigenic Character of the Toxin Produced by Strain N–06," *Journal of Insect Pathology* 5:94–97 (1963).

Lysenko, "Chitinase of *Serratia marcescens* and Its Toxicity to Insects," *J. of Invertebrate Patho.* 27:385–386 (1976).

Meyers et al., "Infections Caused by Microorganisms of the Genus Erwinia," *Annals of Internal Medicine* 76:9–14 (1972).

Mittler et al., "Inhibition of Programmed Cell Death in Tobacco Plants during a Pathogen–Induced Hypersensitive Response at Low Oxygen Pressure," *The Plant Cell* 8:1991–2001 (1996).

Mullett et al., "Analysis of Immune Defences of the Wax Moth, *Galleria mellonella*, with Anti–haemocytic Monoclonal Antibodies," *J. Insect Physiol.* 39:897–902 (1993).

Ohman et al., "Toxin A–Deficient Mutants of *Pseudomonas aeruginosa* PA103: Isolation and Characterization," *Infection and Immunity* 28:899–908 (1980).

Ostroff et al., "Identification of a New Phospholipase C Activity by Analysis of an Insertional Mutation in the Hemolytic Phospholipase C Structural Gene of *Pseudomonas aeruginosa*," *Journal of Bacteriology* 169:4597–4601 (1987).

Pant et al., "Cellulolytic Activity In A Phytophagous Lepidopteran Insect *Philosamia Ricini:*The Origin of the Enzymes," *Insect Biochem.*, 19:269–276 (1989).

Preston et al., "Rapid and Sensitive Method for Evaluating *Pseudomonas aeruginosa* Virulence Factors during Corneal Infections in Mice," *Infection and Immunity* 63:3497–3501 (1995).

Pye et al., "Hemocytes Containing Polyphenoloxidase in Galleria Larvae after Injections of Bacteria," *Journal of Invertebrate Pathology* 19:166–170 (1972).

Rahme et al., "Common Virulence Factors for Bacterial Pathogenicity in Plants and Animals," *Science* 268:1899–1902 (1995).

Raun et al., "Bacterial Pathogens in Iowa Corn Insects," *Journal of Insect Pathology* 5:66–71 (1963).

Reimmann et al., "The Global Activator GacA of *Pseudomonas aeruginosa* PAO Positively Controls the Production of the Autoinducer N–butyryl–homoserine Lactone and the Formation of the Virulence Factors Pyocyanin, Cyanide, and Lipase," *Molecular Microbiology* 24:309–319 (1997).

Rich et al., "Genetic Evidence that the gacA Gene Encodes the Cognate Response Regulator for the lemA Sensor in *Pseudomonas syringae*," *Journal of Bacteriology* 176:7468–7475 (1994).

Ritter et al., "tRNA Genes and Pathogenicity Islands: Influence on Virulence and Metabolic Properties of Uropathogenic *Escherichia coli*," *Molecular Microbiology* 17:109–121 (1995).

Russell et al., "Antibacterial Proteins in the Midgut of *Manduca sexta* During Metamorphosis," *J. Insect Physiol.* 42:65–71 (1996).

Schroth et al., "Epidemiology of *Pseudomonas Aeruginosa* in Agricultural Areas," *Pseudomonas aeruginosa: Ecological Aspects and Patient Colonization*, pp. 1–29 (1977).

Sorn et al., "Isolation & Identification of *Pseudomonas aeruginosa* Pathogenic to Insect Larvae," *Indian Journal of Experimental Biology* 18:590–593 (1980).

Stephens et al., "Some Properties of an Immune Factor Isolated From The Blood Of Actively Immunized Wax Moth Larvae," *Canadian Journal of Microbiology* 8:719–725 (1962).

Stephens, "Bacteridical Activity Of The Blood Of Actively Immunized Wax Moth Larvae," *Canadian Journal of Microbiology* 8:491–499 (1962).

Stephens, "Immune Responses Of Some Insects To Some Bacterial Antigens," *Canadian Journal of Microbiology* 5:203–228 (1959).

Stevens et al., "A Quantitative Model of Invasive Pseudomonas Infection in Burn Injury," *Journal of Burn Care & Rehabilitation* 15:232–235 (1994).

Swift et al., "Quorum Sensing: A Population–Density Component in the Determination of Bacterial Phenotype," *Trends Biochem. Sci.* 21:214–219 (1996).

Turner et al., "Occurrence, Biochemistry and Physiology of Phenazine Pigment Production," *Advances in Microbial Physiology* 27:210–275 (1986).

Vlayen et al., "Identification Of The Gut Bacterial Micro Flora In Armyworms Mamestra–Brassicae Lepidoptera Noctuidae Importance Of The Environment," *Annales de la Societe Royale Zoologique de Belgique* 112:23–39 (1982).

Webster's II, New Riverside University Dictionary, The Riverside Publishing Company. Definitions of "Mushroom" and "Fungus," pp. 512 and 778 (1988).

Winans et al., "Adaptation of a conjugal Transfer System for the Export of Pathogenic Macromolecules," *Trends In Microbiology* 64:64–68 (1996).

Xu et al., "Molecular Cloning of Genes that Specify Virulence in *Pseudomonas solanacearum*" *Journal of Bacteriology* 170:617–622 (1988).

\* cited by examiner

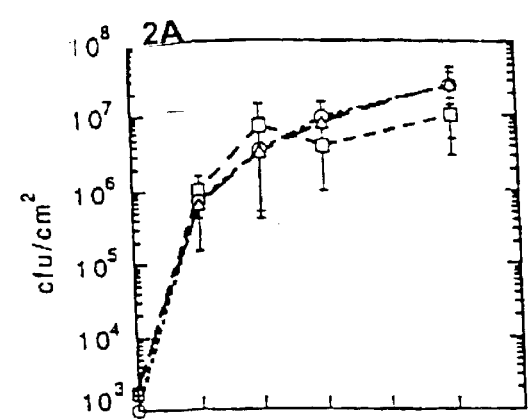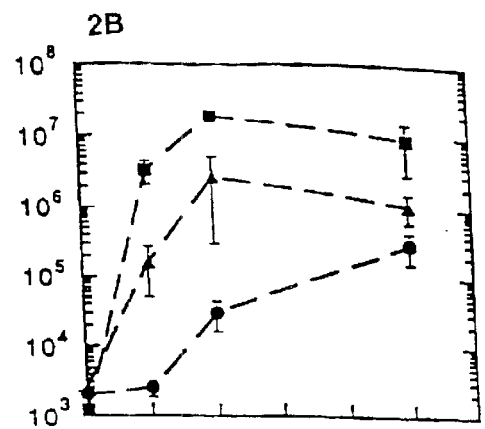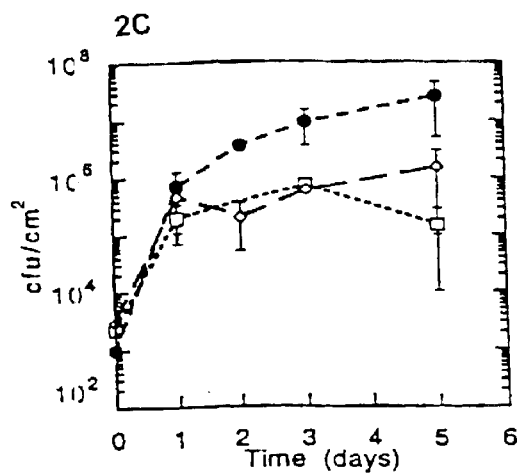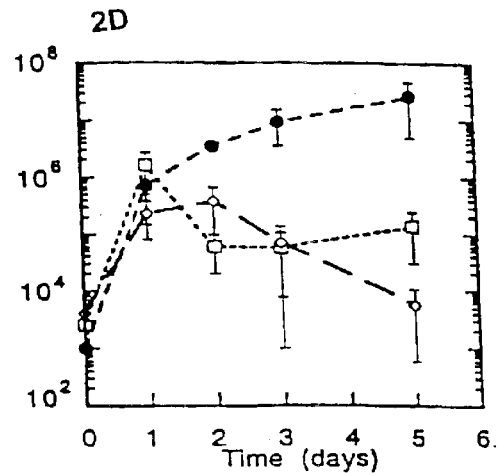
Figs. 2 A-D

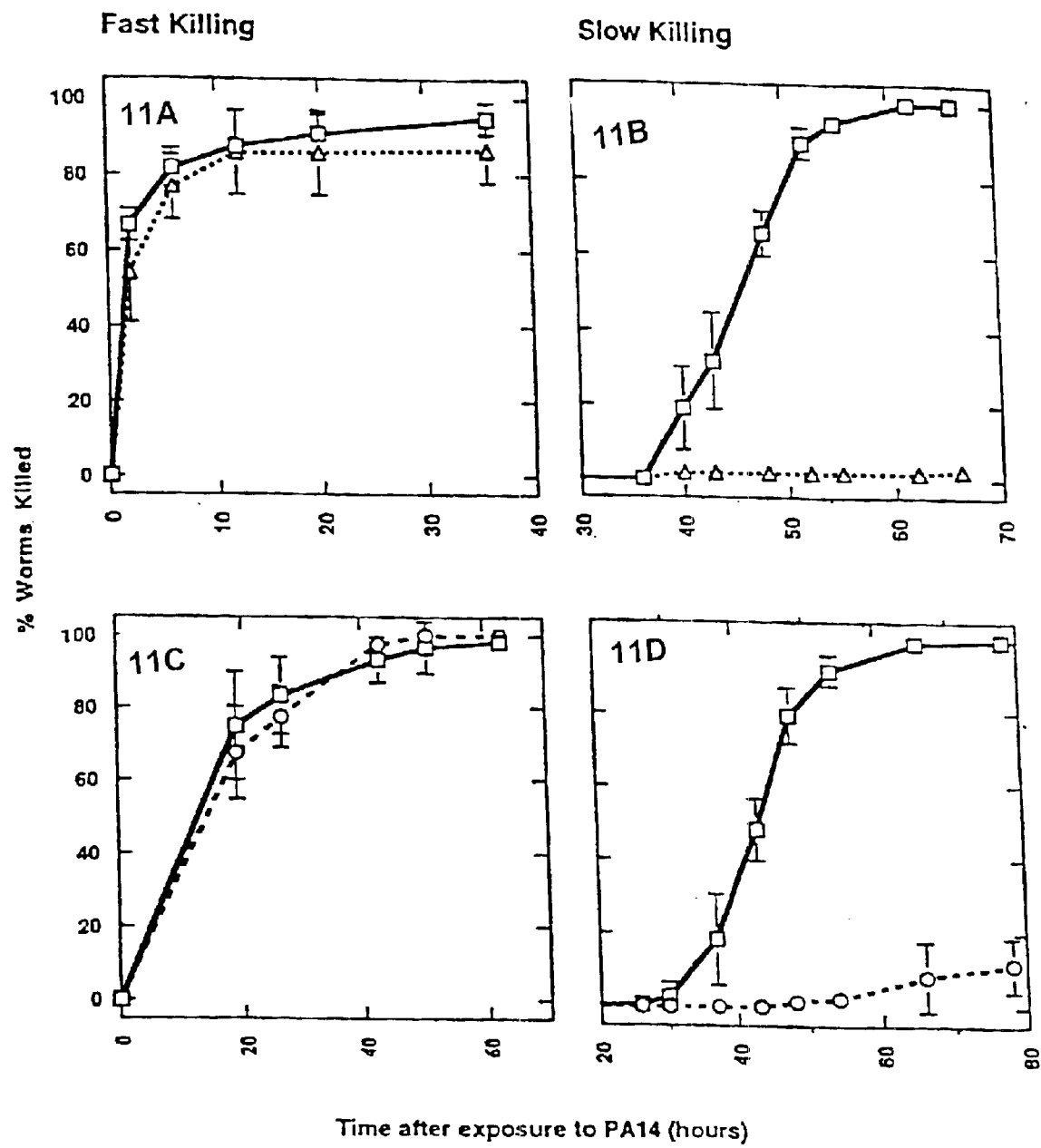
Figs. 11 A-D

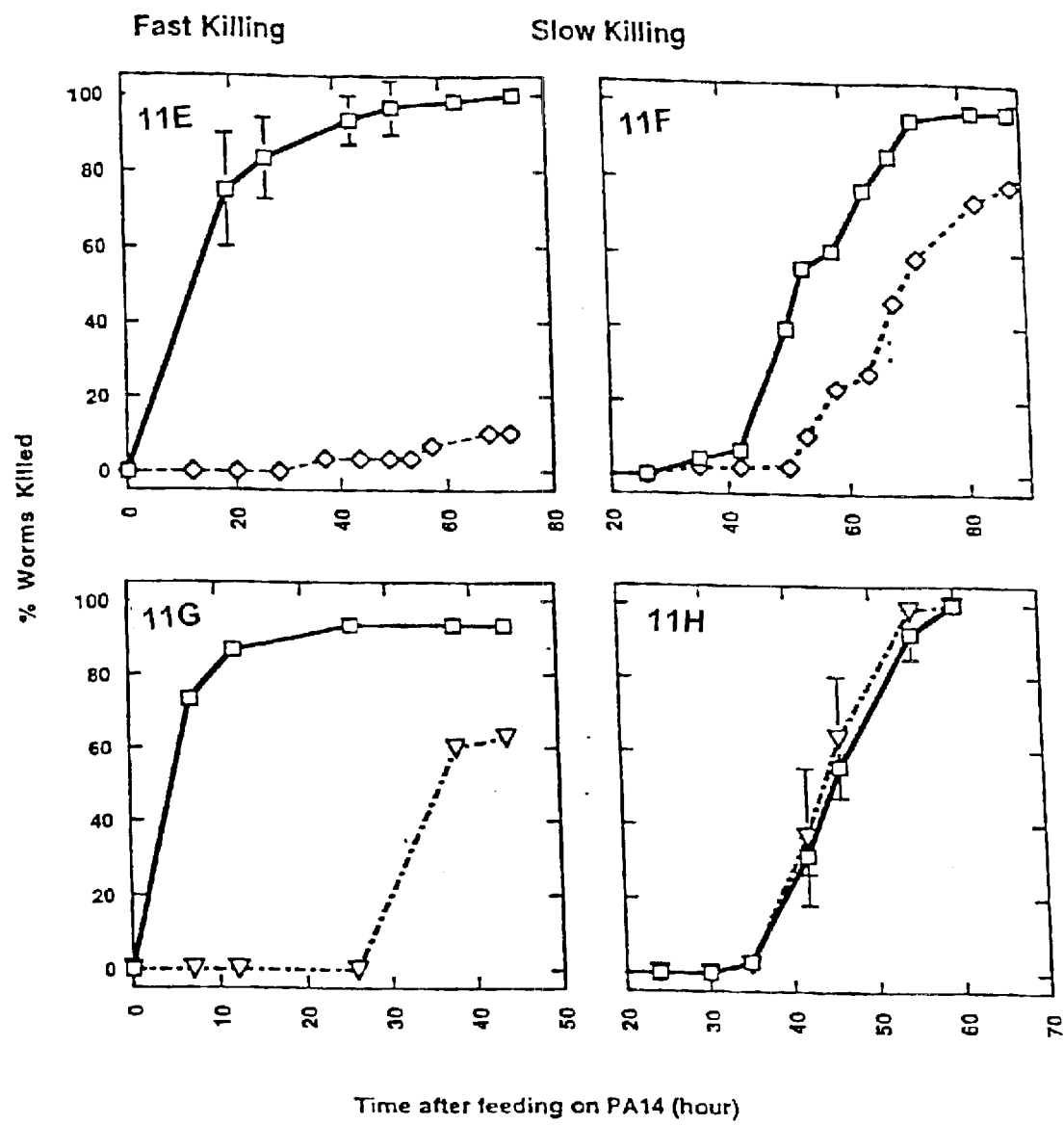
Figs. 11 E-H

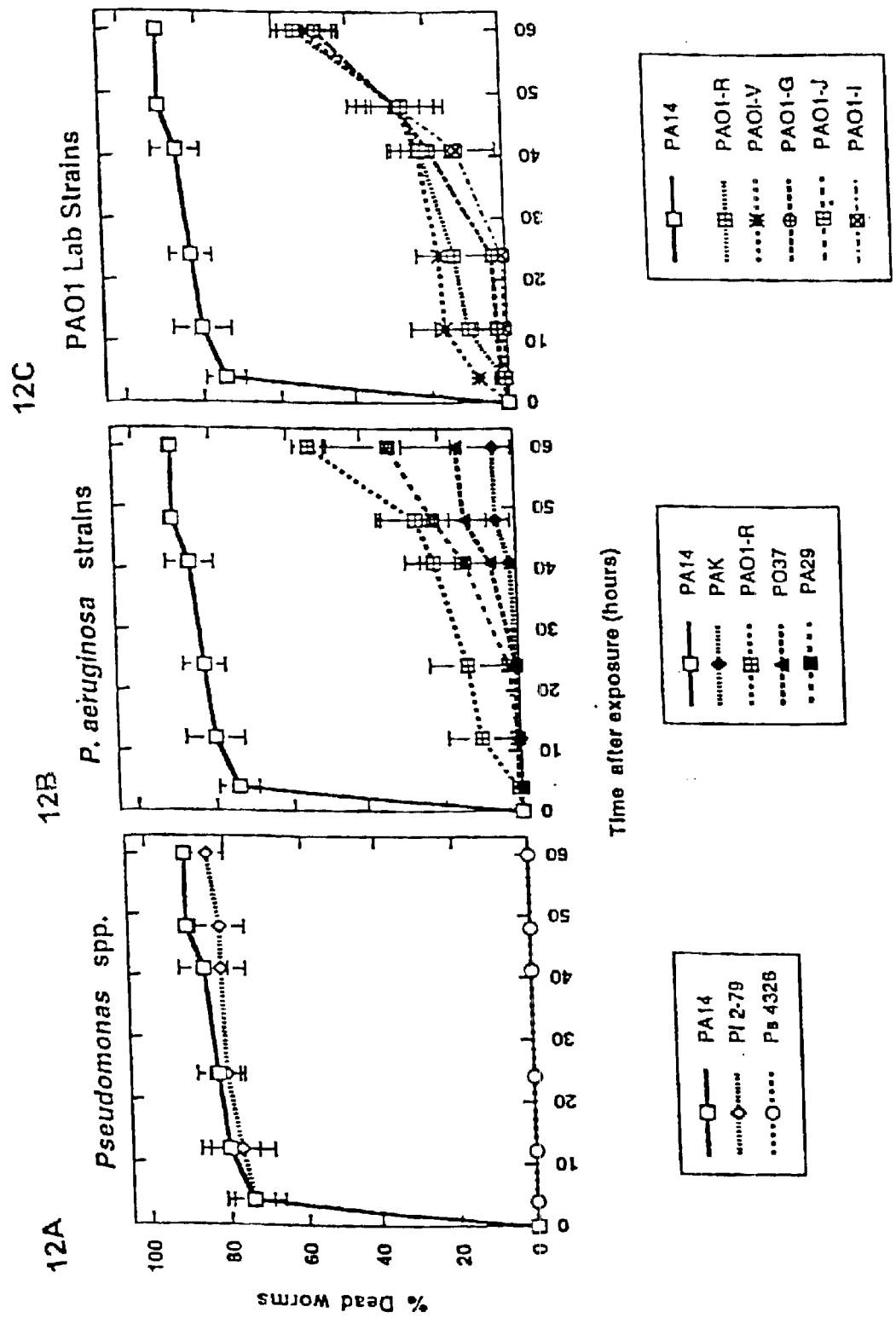
Figs. 12 A-C

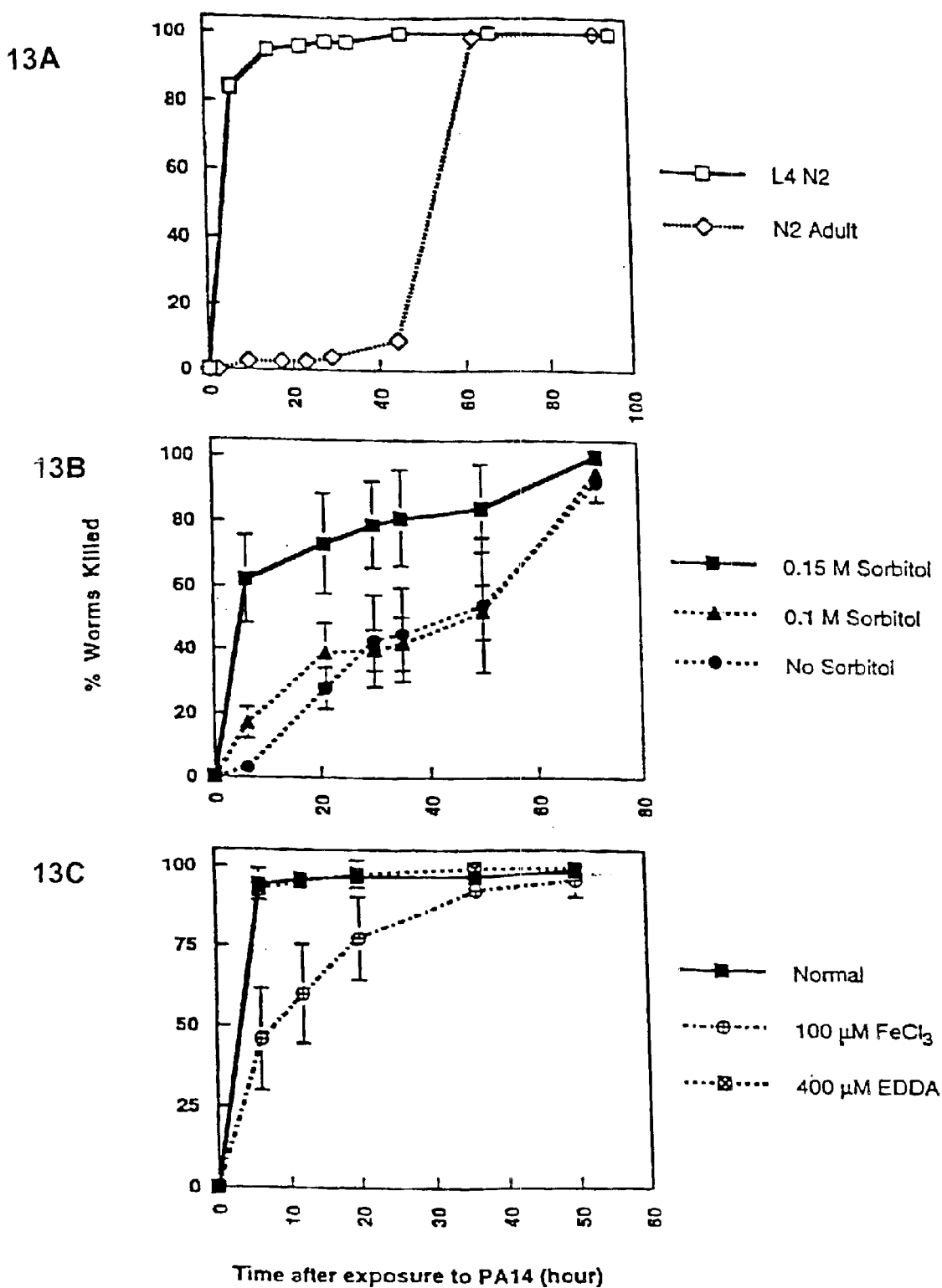
Figs. 13 A-C

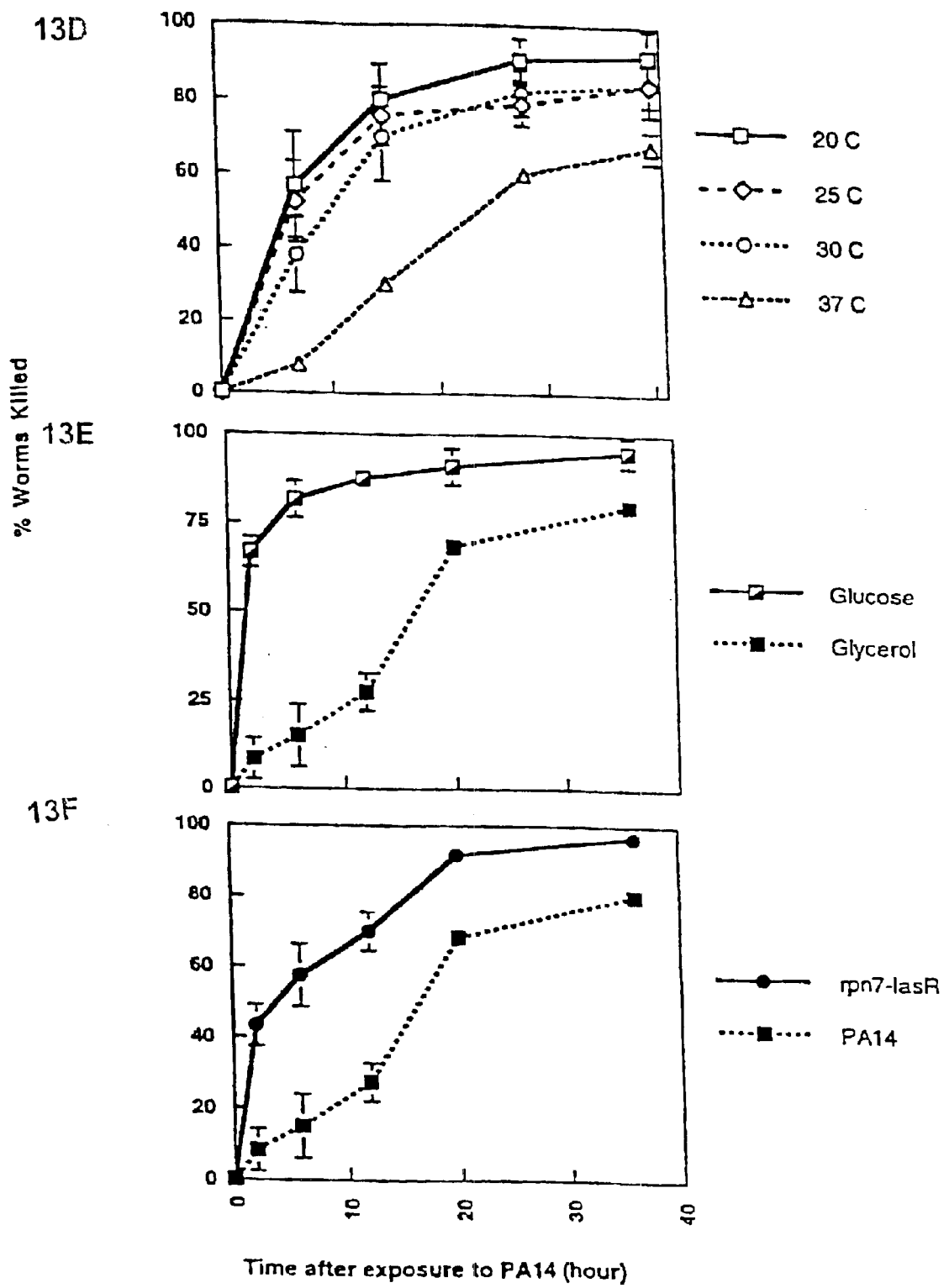
Figs. 13 D-F

14A
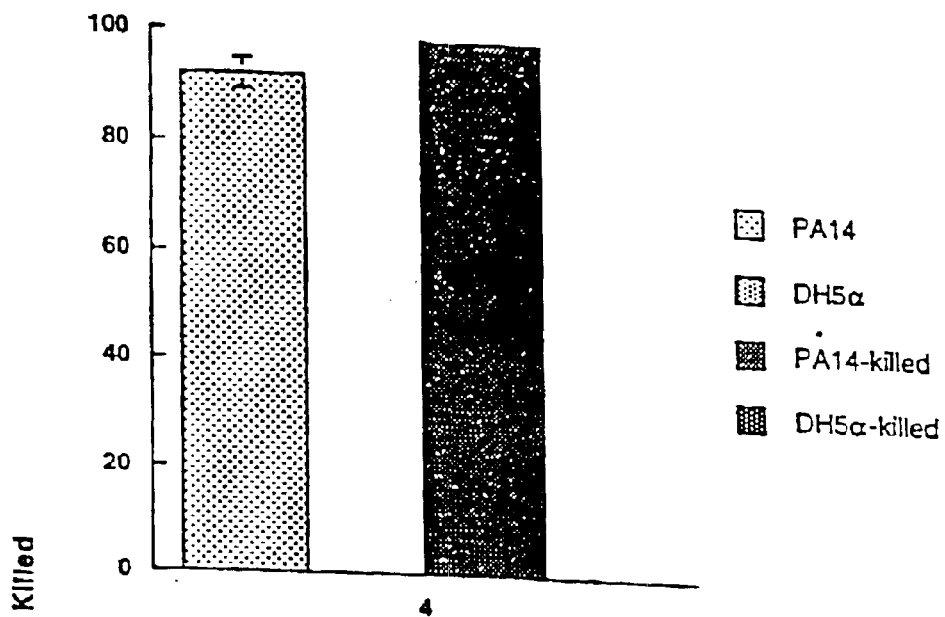
14B
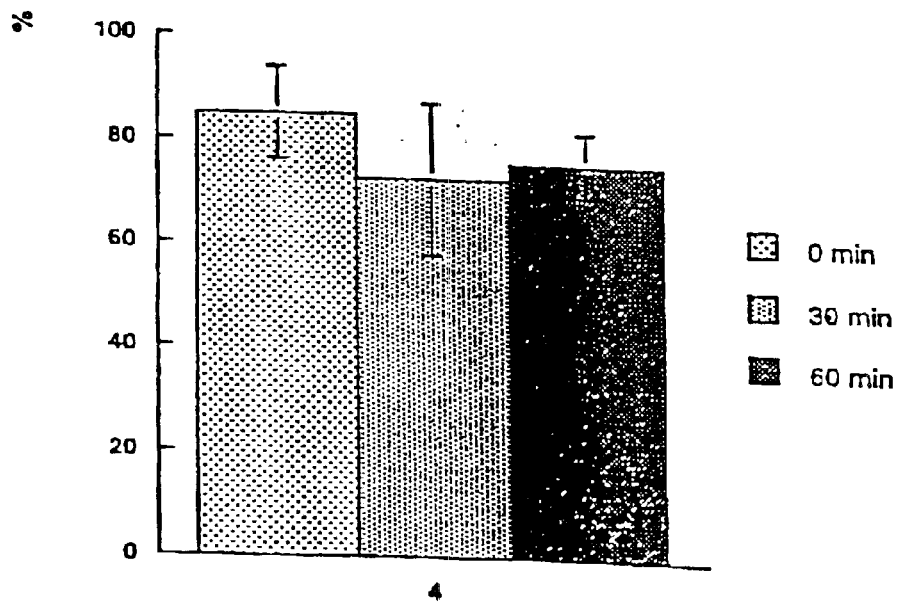
Time in hours
Figs. 14 A-B

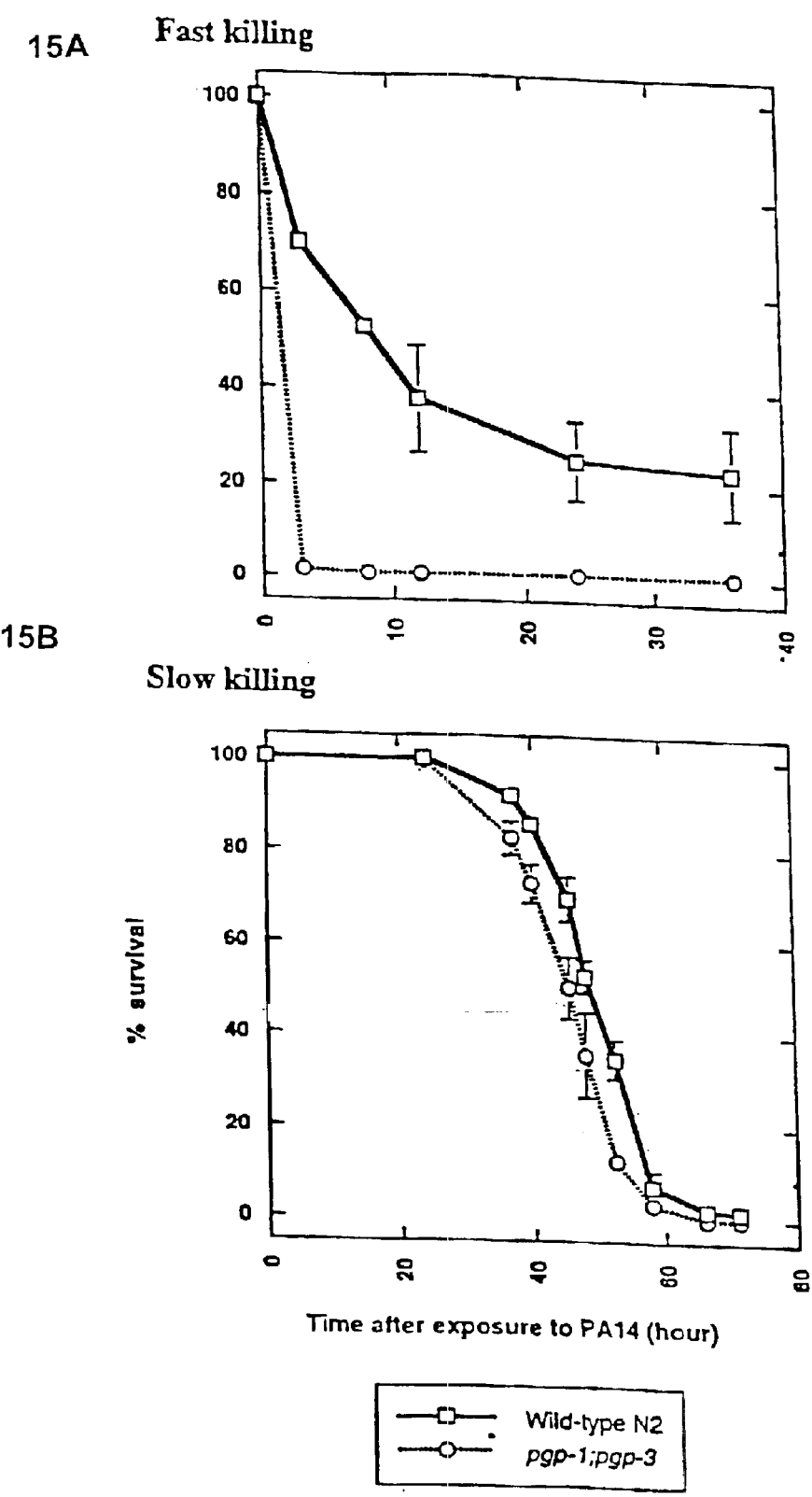
Figs. 15 A-B

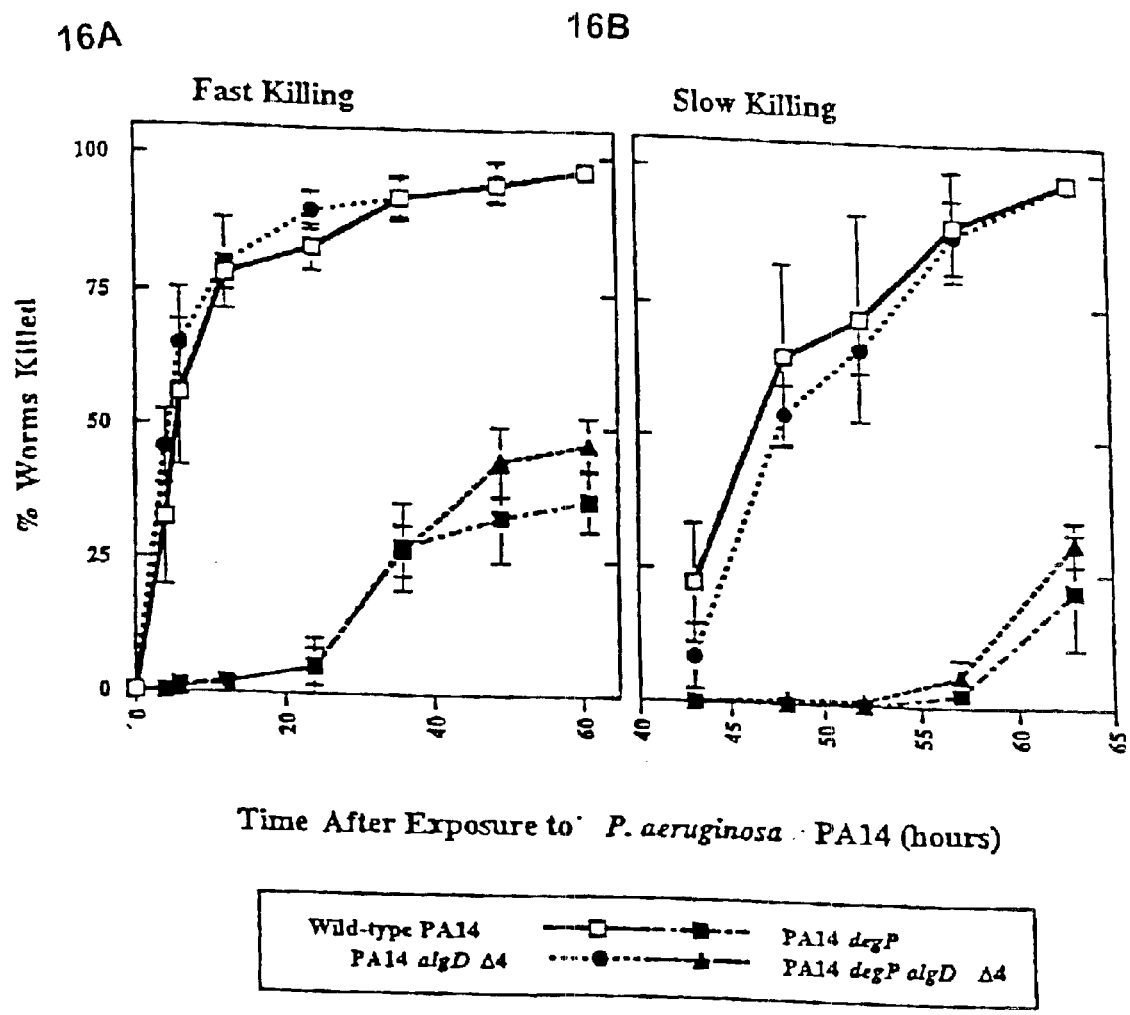
Figs. 16 A-B

Figs. 18 A-B

SEQUENCE LISTING

```
<160> NUMBER OF SEQ ID NOS: 2
<210> SEQ ID NO 1
<211> LENGTH: 17
<212> TYPE: DNA
<213> ORGANISM: Pseudomonas aeruginosa PA14

<400> SEQUENCE: 1
gctagtagtc gatgacc                                                  17

<210> SEQ ID NO 2
<211> LENGTH: 17
<212> TYPE: DNA
<213> ORGANISM: Pseudomonas aeruginosa PA14

<400> SEQUENCE: 2
gctggcatca accatgc                                                  17
```

METHODS OF SCREENING COMPOUNDS USEFUL FOR PREVENTION OF INFECTION OR PATHOGENICITY

This application is a continuation-in part of co-pending application U.S. Ser. No. 08/962,750, filed on Nov. 3, 1997, which is a continuation-in-part of Ser. No. 08/852,927, filed on May 8, 1997, now abandoned, which is a continuation-in-part of application U.S. Ser. No. 08/411,560 (now U.S. Pat. No. 6,461,854), filed Mar. 28, 1995.

BACKGROUND OF THE INVENTION

The invention relates to screening procedures which identify compounds for inhibiting infection or disease in a eukaryotic host organism, or which induce or stimulate a host's pathogenic defense mechanisms. The invention also relates to the use of such compounds as anti-pathogens. In addition, the invention relates to procedures which identify pathogenic virulence factors.

Microbial pathogens such as bacteria, protozoa, fungi, nematodes, and viruses include a large and diverse group of organisms capable of infecting animals and plants. Initiation of an infection occurs when the infecting organism is pathogenic, and the host is susceptible to pathogenic invasion. After establishing contact with susceptible cells or tissues of the host, the pathogen acquires nutrients from its host, facilitating its own survival. During the infection process the pathogen activates a cascade of molecular, biochemical, and physiological processes, the result of which is the release of substances detrimental to the host and the development of disease (See, e.g., *Scientific American Medicine*, W. H. Freeman and Co., Calif., San Francisco, 1995; Agrios, G. N., *Plant Pathology*, Academic Press, 1988). The pathogenic effects of microbes are produced in a variety of ways.

Some pathogens act through secreted products. Diphtheria, for instance, is caused by the bacillus, *Cornynebacterium diptheriae*. This organism is inhaled by the host and establishes infection in the upper respiratory tract. While the bacterium does not itself invade the bloodstream, its powerful toxins do. These toxins are then absorbed by the cells of the body, enzyme function is impaired, and host cells are destroyed.

Other diseases are the result of the body's reaction to a pathogen. For example, in pneumonia, a disease caused by *Streptococcus pneumoniae*, infection causes an outpouring of fluid and cells into the air sacs of the lungs, interfering with respiration. Fungal infections of the skin similarly result from such inflammatory responses.

Yet other bacteria are opportunistic pathogens. *Pseudomonas aeruginosa*, for example, infects patients with thermal burns and patients who are immunodeficient or otherwise immunologically compromised. *P. aeruginosa* infections can be acute and localized as in corneal ulcers and otitis media, chronic as in the lungs of cystic fibrosis patients, or systemic following bloodstream invasion.

Plant pathogenic diseases are also of concern because they cause damage to plants and plant products. Phytopathogens produce disease in plants by any number of methods including: (1) consuming host cell nutrients; (2) killing or disrupting host cell metabolism through toxins, enzymes, or growth-regulators; (3) affecting photosynthesis by inducing chlorosis (e.g., by degrading chloroplasts); and (4) blocking conductive tissues and interfering with normal physiological processes.

Crop plants, ornamentals, trees, and shrubs are especially vulnerable to diseases caused by bacteria, fungi, viruses, and nematodes. Phytopathogenic bacteria, for example, cause the development of many disease symptoms including leaf spots and blights, soft-rots, wilts, overgrowths, scabs, and cankers. Bacterial diseases occur most commonly on vegetables (and some ornamentals) that have fleshy storage tissues, such as potatoes, carrots, onions, iris, or hyacinth. They may also occur in plants bearing fleshy fruit (such as cucumber, squash, eggplant, or tomato), as well as in leafy plants (such as cabbage, celery, lettuce, or spinach). Plant bacterial diseases occur throughout the world and cause serious damage to crops in the field, in transit, and in storage.

The mechanisms of plant pathogenesis are many and varied. One bacterial phytopathogen Erwinia, for example, causes plant diseases such as soft-rot and fire-blight by penetrating a plant through a wound or an accessible natural opening. Once inside, the bacteria secrete enzymes which break down the plant's middle lamellae, resulting in the maceration of tissue and ultimately cell death. Other bacteria, such as certain strains of Pseudomonas, may interfere with water translocation by disrupting xylem within the plant. Pseudomonads invade the xylem of roots and stems and, once inside, secrete enzymes and toxins which destroy the plant. Still other phytopathogenic bacteria, like Agrobacterium and Corynebacterium, stimulate cell division and cell enlargement in affected tissues. This generally leads to the development of amorphous overgrowths, galls, or tumors on roots, stems, or other organs (e.g., crown gall caused by *Agrobacterium tumefaciens*), or in the proliferation of infected organs (e.g., hairy root caused by *Agrobacterium rhizogenes*).

Prompt identification of the causative organism is essential to the appropriate selection of anti-pathogenic agents and successful management of clinical and agricultural infections. However, the extensive use of anti-pathogenic agents, such as sulfonamides, tetracyclines, ampicillins, cephalosporins, and aminoglycosides, in both medicine and agriculture has strongly favored the selection of resistant microbial species. This is especially true of bacterial strains containing transmissible resistance plasmids. For example, outbreaks of nosocomial infections from highly resistant strains of Serratia, Klebsiella, Pseudomonas, Acinetobacter, Enterobacter, and Streptococcus have become important and recurrent problems. As a result of selecting resistant strains, over the past few decades, *P. aeruginosa* has emerged as an important and problematic clinical pathogen, causing between 10% and 20% of infections in hospitals. Currently, several aminoglycosides and third-generation cephalosporins are efficacious against *P. aeruginosa*, but the relative ease with which *P. aeruginosa* acquires resistance necessitates the search for new compounds as potential replacements or alternative therapies.

SUMMARY OF THE INVENTION

We have discovered that common pathogenic virulence factors are involved in the infection and pathogenicity of both animal and plant hosts. The identification of such host-independent virulence factors has facilitated improved screening methods designed to evaluate and identify therapeutic agents useful for inhibiting pathogenesis in either animal or plant hosts, or both. Furthermore, our discovery provides the basis for screening methods useful for identifying a variety of new virulence factors. Identification of such virulence factors also facilitates the development of targeted reagents for use as anti-pathogens.

In a first aspect, therefore, the invention generally features a method for identifying a compound which is capable of inhibiting a fungal pathogen in a eukaryotic organism. The method involves (a) exposing (either sequentially or simultaneously) at least two eukaryotic organisms to a single fungal pathogen in the presence of at least one candidate compound; and (b) identifying a compound that inhibits the fungal pathogen in each of the eukaryotic organisms.

In preferred embodiments, one of the eukaryotic host organisms is a non-rodent; the fungal pathogen is a yeast (e.g., Cryptococcus, Candida, Rhodotorula, or Saccharomyces); and the eukaryotic organisms include a vertebrate and a plant; a vertebrate and an invertebrate, or a plant and an invertebrate. Preferably, the invertebrate is a nematode (e.g., a member of the genus Caenorhabditis); and the plant is a member of the genus Arabidopsis. In other preferred embodiments each of the eukaryotic host organisms is a plant, is a vertebrate, or is an invertebrate.

In a second aspect, the invention features a method for identifying a compound which is capable of inhibiting a fungal pathogen in a eukaryotic host organism. The method involves (a) exposing the eukaryotic host organism to a single fungal pathogen in the presence of at least one candidate compound; and (b) identifying a compound that inhibits the fungal pathogen in the eukaryotic host organism.

In preferred embodiments, one of the eukaryotic host organisms is a non-rodent; the fungal pathogen is a yeast (e.g., Cryptococcus, Candida, Rhodotorula, or Saccharomyces); the eukaryotic organisms include a vertebrate and a plant, a vertebrate and an invertebrate; or a plant and an invertebrate. Preferably, the invertebrate is a nematode (e.g., a member of the genus Caenorhabditis) or an insect (e.g., a member of the genus Galleria or Drosophila), and the plant is a member of the genus Arabidopsis.

In a third aspect, the invention features a method for identifying a fungal virulence factor. The method involves (a) identifying a fungal pathogen which is capable of infecting at least two different eukaryotic organisms, the two different eukaryotic organisms being chosen from (i) an animal and a plant or (ii) a vertebrate and an invertebrate; (b) generating a mutant of the fungal pathogen; (c) exposing each of the organisms to the mutated pathogen; (d) determining whether the mutated fungal pathogen is capable of causing disease in each of the organisms, a reduction of disease in both of the organisms relative to that caused by the wild-type fungal pathogen indicating a mutation in the fungal virulence factor, and (e) using the mutation as a marker for identifying the fungal virulence factor.

In a fourth aspect, the invention features a method for mutating a pathogenic fungal virulence factor. The method involves (a) identifying a fungal pathogen which is capable of infecting at least two different eukaryotic organisms, the two different eukaryotic organisms being chosen from (i) an animal and a plant or (ii) a vertebrate and an invertebrate; (b) generating a mutant of the fungal pathogen; (c) exposing each of the organisms to the mutated fungal pathogen; and (d) determining whether the mutated fungal pathogen is capable of causing disease in each of the organisms, a reduction of disease in both of the organisms relative to that caused by the wild-type fungal pathogen indicating a mutation in the fungal virulence factor.

In a fifth aspect, the invention features a method of reducing the virulence of a fungal pathogen. The method involves (a) identifying a fungal pathogen which is capable of infecting at least two different eukaryotic organisms, the two different eukaryotic organisms being chosen from (i) an animal and a plant or (ii) a vertebrate and an invertebrate; (b) generating a mutant of the fungal pathogen; (c) exposing each of the organisms to the mutated fungal pathogen; and (d) determining whether the mutated fungal pathogen is capable of causing disease in each of the organisms, a reduction of disease in both of the organisms relative to that caused by the wild-type fungal pathogen indicating a reduction in fungal virulence.

In preferred embodiments of the third, fourth, and fifth aspects of the invention, the animal is a vertebrate (e.g., a rodent) and the plant is a crucifer. In another preferred embodiment, the animal is an invertebrate, preferably a nematode, and the plant is a crucifer. In other preferred embodiments of these aspects, the fungal pathogen is a yeast (e.g., Cryptococcus, Candida, Fusarium, Rhodotorhula, or Saccharomyces).

In a sixth aspect, the invention generally features an isolated nematode infected with a pathogen. In one preferred embodiment, the pathogen is a bacterium (e.g., Pseudomonas). In another preferred embodiment, the pathogen is a fungus (e.g., Cryptococcus, Candida, Fusarium, Rhodotorula, or Saccharomyces).

By "non-rodent" is meant any organism that is not a mouse, a rat, a guinea pig, or a hamster.

By a "fast killing" assay is meant an assay in which greater than fifty percent of the nematodes in a test population are killed in less than about thirty-six hours. In preferred embodiments, such killing is accomplished in a time period ranging from about twelve to twenty-four hours. In yet a further preferred embodiment, killing is accomplished in about four hours.

By "pathogenic virulence factor" is meant a cellular component (e.g., a protein such as a transcription factor) without which the pathogen is incapable of causing disease or infection in a eukaryotic host organism.

The invention provides long awaited advantages over a wide variety of standard screening methods used for distinguishing and evaluating the efficacy of a compound against microbial pathogens. For example, the screening methods described herein allow for the simultaneous evaluation of host toxicity as well as anti-pathogen potency in a simple in vivo screen. Moreover, the methods of the invention allow one to evaluate the ability of a compound to inhibit microbial pathogenesis, and, at the same time, to evaluate the ability of the compound to stimulate and strengthen a host's response to pathogenic attack.

Accordingly, the methods of the invention provide a facile means to identify compounds that are safe for use in eukaryotic host organisms (i.e., compounds which do not adversely affect the normal development and physiology of the organism), and efficacious against pathogenic microbes (i.e., by suppressing the virulence of a pathogen). In addition, the methods of the invention provide a route for analyzing virtually any number of compounds for anti-pathogenic effect with high-volume throughput, high sensitivity, and low complexity. The methods are also relatively inexpensive to perform and enable the analysis of small quantities of active substances found in either purified or crude extract form. Furthermore, the methods disclosed herein provide a means for identifying anti-pathogenic compounds which have the capability of crossing eukaryotic cell membranes and which maintain therapeutic efficacy in an in vivo method of administration.

Other features and advantages of the invention will be apparent from the following description of the preferred embodiments thereof, and from the claims.

DETAILED DESCRIPTION

The drawings will first be described.

DRAWINGS

The patent file contains one drawing executed in color. Copies of this patent with the color drawing will be provided by the Patent and Trademark Office upon request and payment of the necessary fee.

FIG. 1 is a color photograph showing the symptoms caused by *Pseudomonas syringae* and *Pseudomonas aeruginosa* on Arabidopsis (ecotype Llagostera (Ll)) leaves. Mock-inoculated (left); *Pseudomonas syringae* pv. *maculicola* strain ES4326 (center); *Pseudomonas aeruginosa* strains UCBPP-PA14 (right).

FIGS. 2A–D are graphs showing the growth of *Pseudomonas syringae* and *Pseudomonas aeruginosa* in Arabidopsis leaves. FIG. 2A is a graph showing the growth of *Pseudomonas syringae* pv. *maculicola* strain ES4326 (open squares), *Pseudomonas aeruginosa* strain UCBPP-PA14 (open circles), and *Pseudomonas aeruginosa* strain UCBPP-PA29 (open triangles) in ecotype Llagostera. FIG. 2B is a graph showing the growth of *Pseudomonas aeruginosa* strain UCBPP-PA14 in three Arabidopsis ecotypes: Columbia (solid squares); Argentat (solid circles); and Bensheim (solid triangles). FIG. 2C is a graph showing the growth of *Pseudomonas aeruginosa* strain UCBPP-PA14 (solid circles) and isogenic plcS (open squares), and toxA (open diamonds) mutants. FIG. 2D is a graph showing the growth of *Pseudomonas aeruginosa* strain UCBPP-PA14 (solid circles), isogenic gacA (open diamonds), and degP (open squares) mutants in ecotype Llagostera. Bacterial counts in Arabidopsis leaves were performed as described herein. Means of four samples±SD are shown. Three independent experiments gave similar results. Incubation conditions for the plants were identical to the experiments presented in Table I, infra.

Figure 6A:
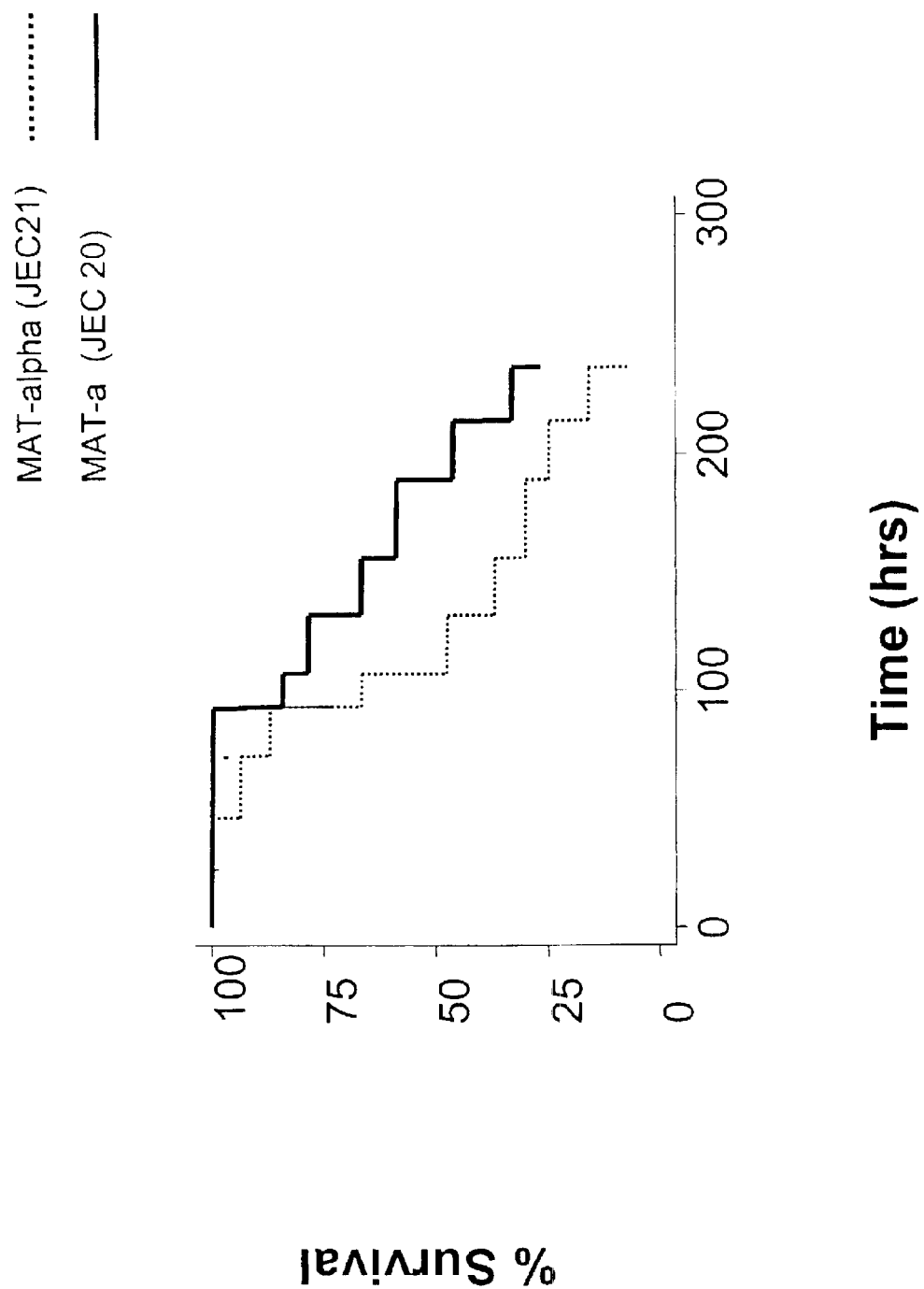
Figure 6B:
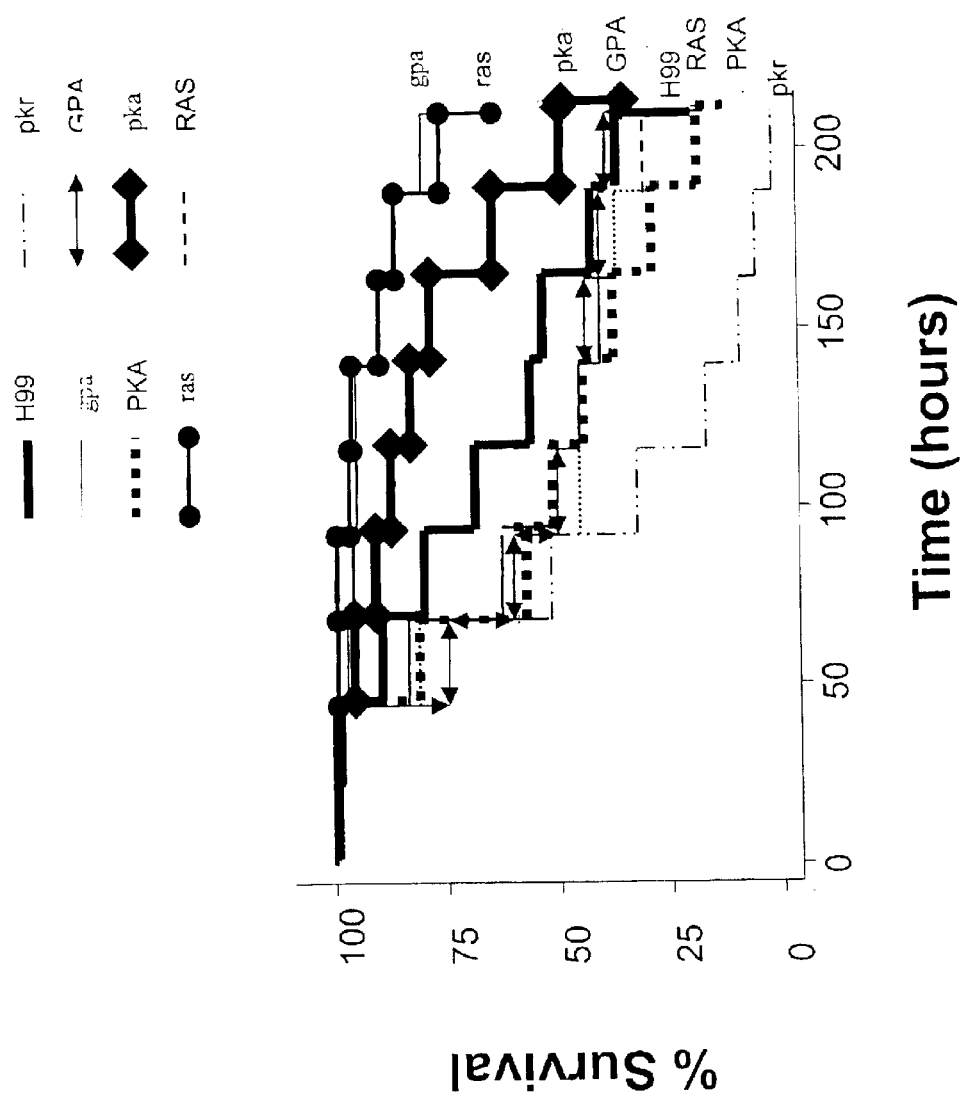
Figure 6C:
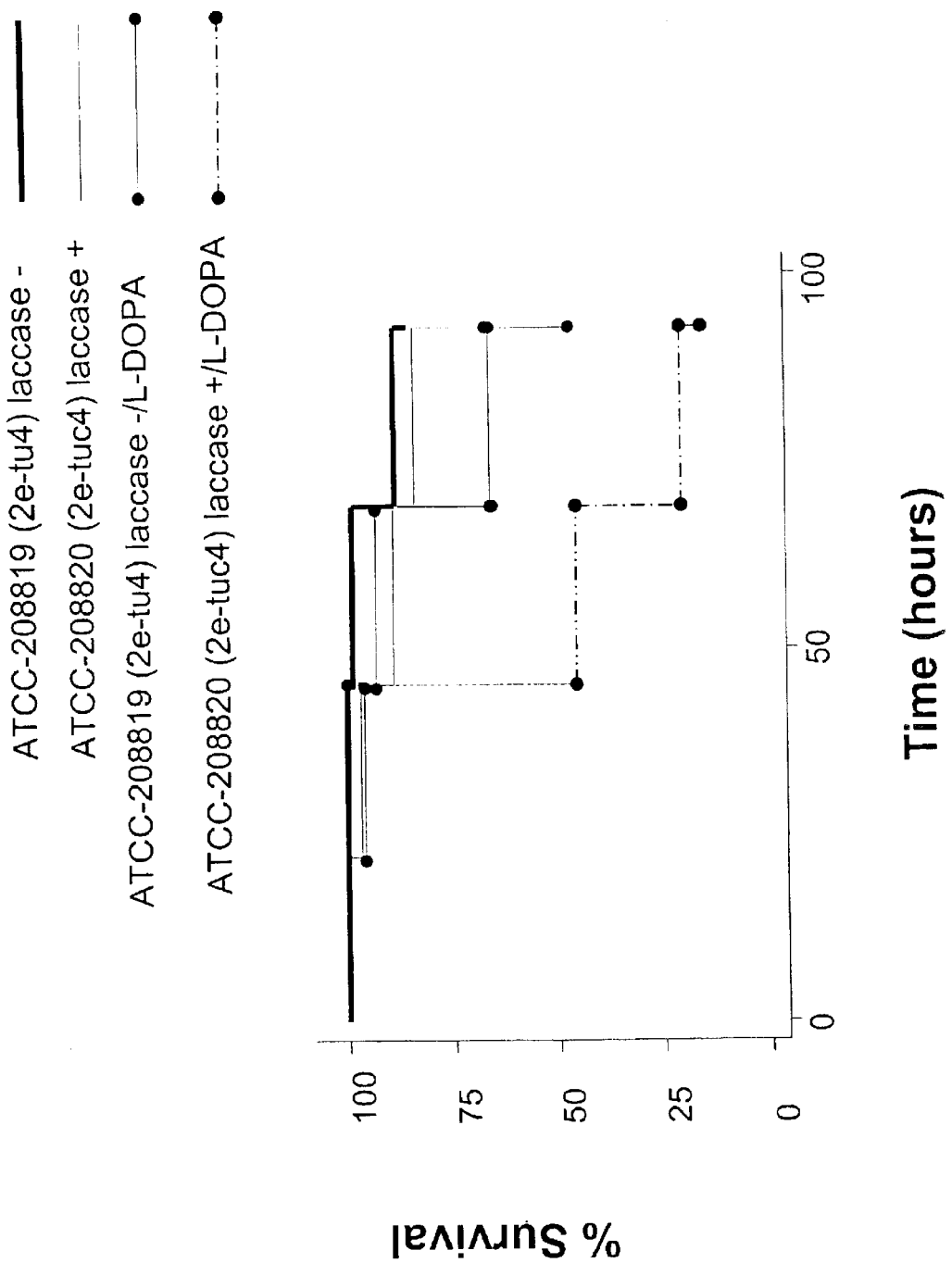

FIGS. 6A–6C are graphs showing *C. elegans* killing by strains of *C. neoformans*. FIG. 6A is a graph showing that two isogenic *C. neoformans* strains, MAT-alpha (JEC 21) and MAT-a (JEC 20), displayed significantly different levels of virulence as measured by *C. elegans* killing. FIG. 6B is a graph showing that *C. neoformans* mutants with disruptions in genes encoding G protein alpha (gpa), RAS (ras), or protein kinase A (PKA) were hypovirulent in *C. elegans* relative to wild-type *C. neoformans* H99. A *C. neoformans* mutant containing a mutation in the gene encoding the protein kinase A regulatory subunit (pkr) was hypervirulent. Reconstitution of the mutations gpa1, ras, and pka hypovirulent mutants with wild-type nucleic acids encoding G protein alpha (GPA), RAS, or protein kinase A (PKA), respectively, restored virulence. FIG. 6C is a graph showing that a laccase-positive strain of *C. neoformans* (ATCC No. 208820) was significantly more virulent than a laccase-deficient strain (ATCC NO. 208819) in the presence of the melanin substrate L-dopamine.

Figure 7A:
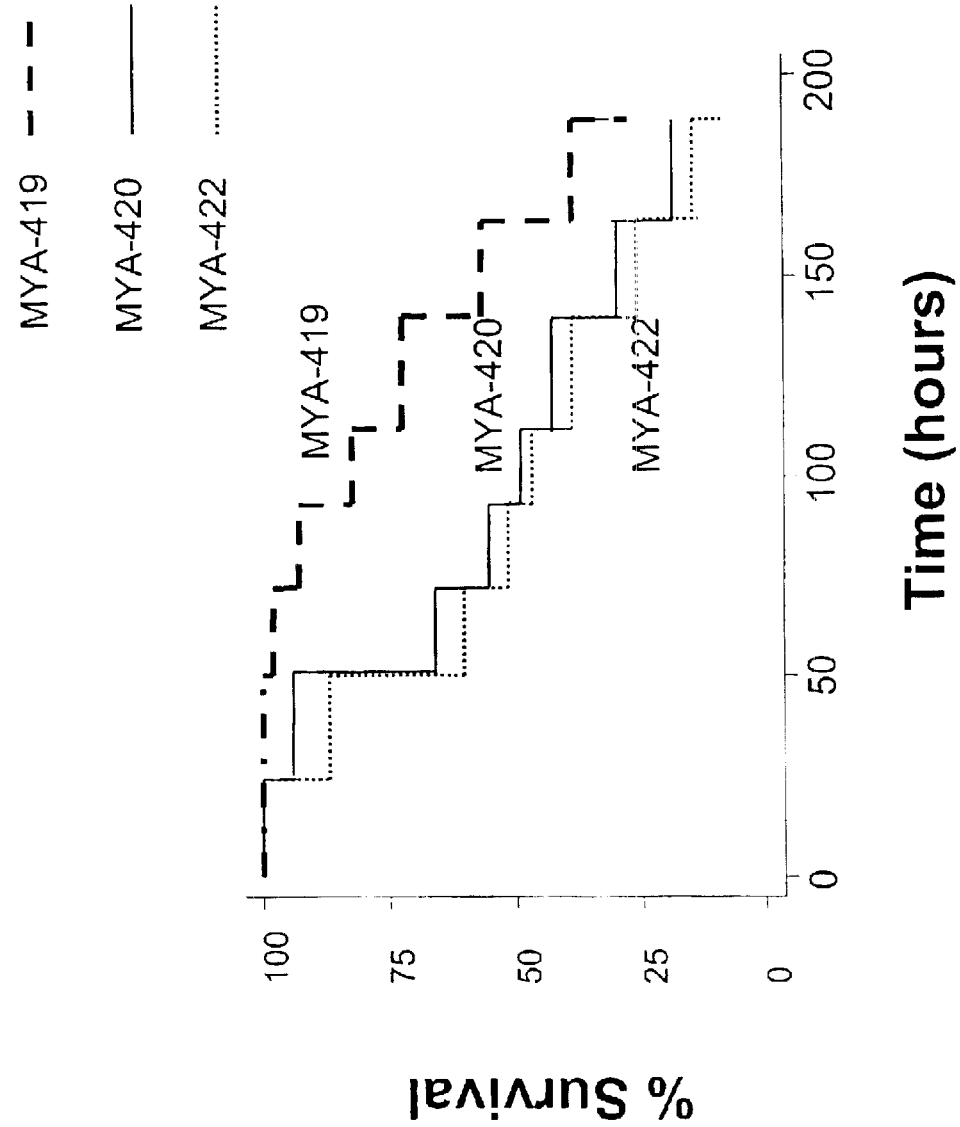
Figure 7B:
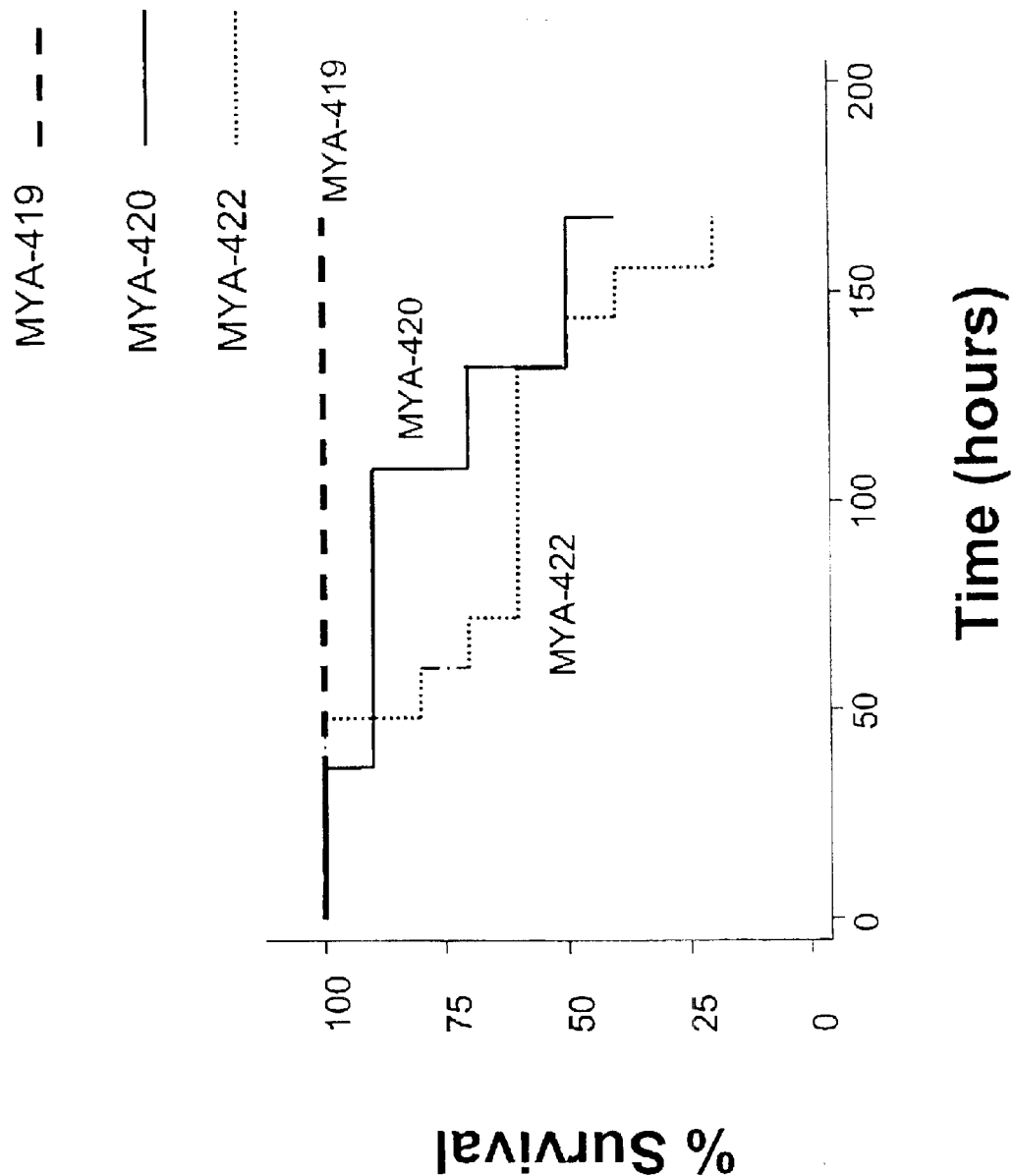

FIGS. 7A–7B are graphs showing killing of *C. elegans* or mice, respectively, by *C. neoformans* strains. FIG. 7A is a graph showing *C. elegans* killing on lawns of mutant (MYA-419 and MYA-420) *C. neoformans* or on lawns of wild type *C. neoformans* (MYA-422). FIG. 7B is a graph showing the killing of mice injected with $2.5 \times 10^7$ cfu of *C. neoformans* strains MYA-419, MYA-420, or MYA-422. *C. neoformans* MYA-419 strain was less virulent than wild-type in this murine model of cryptococcosis ($P<0.0001$, for the comparison of MYA-419 with the wild type strain). Mutant MYA-420 was no less virulent than wild-type in mouse and *C. elegans*.

Figure 8:
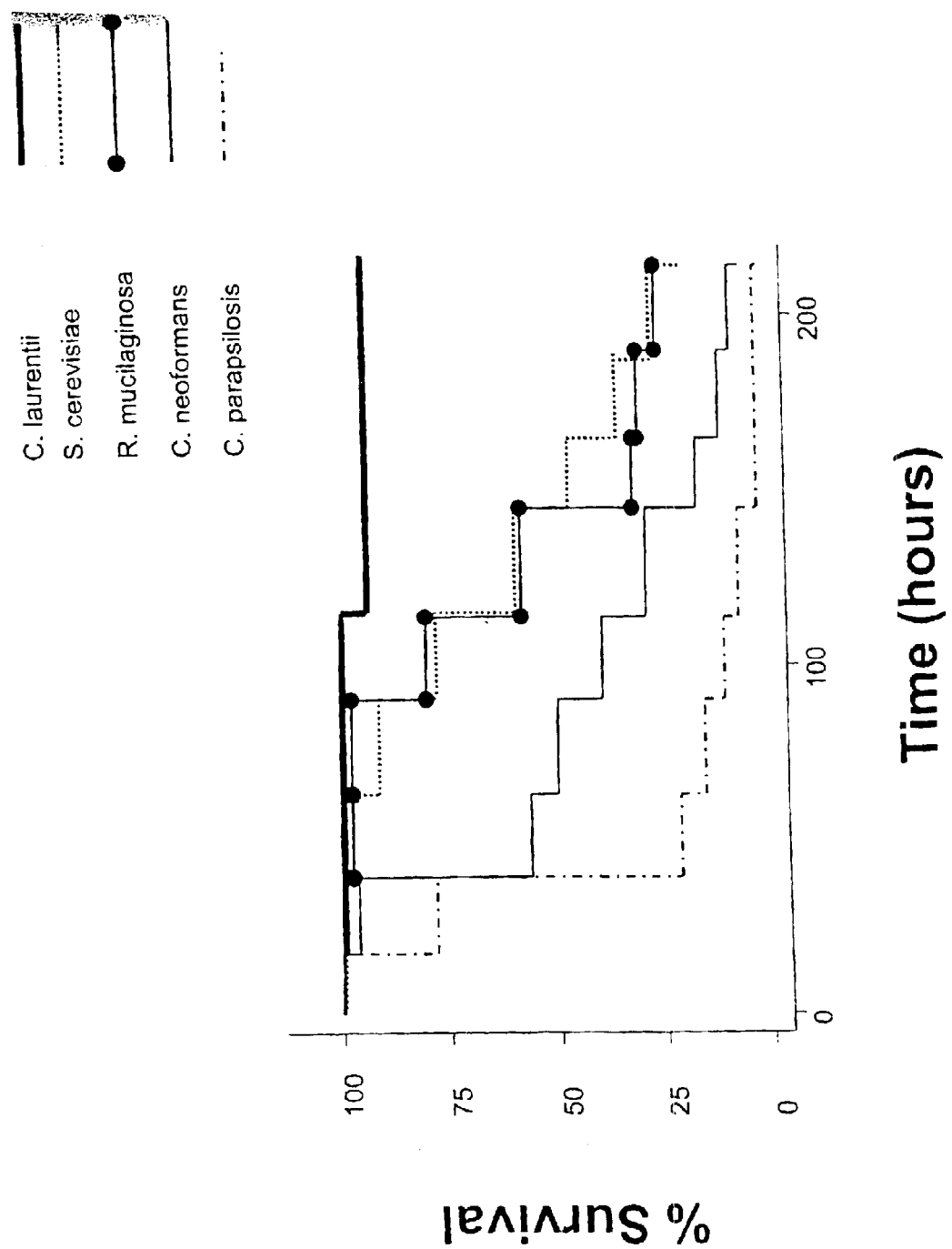

FIG. 8 is a graph showing *C. elegans* killing by *C. laurentii*, *S. cerevisiae*, *R. mucilaginosa*, *C. neoformans*, and *C. parapsilosis*.

Figure 9A:
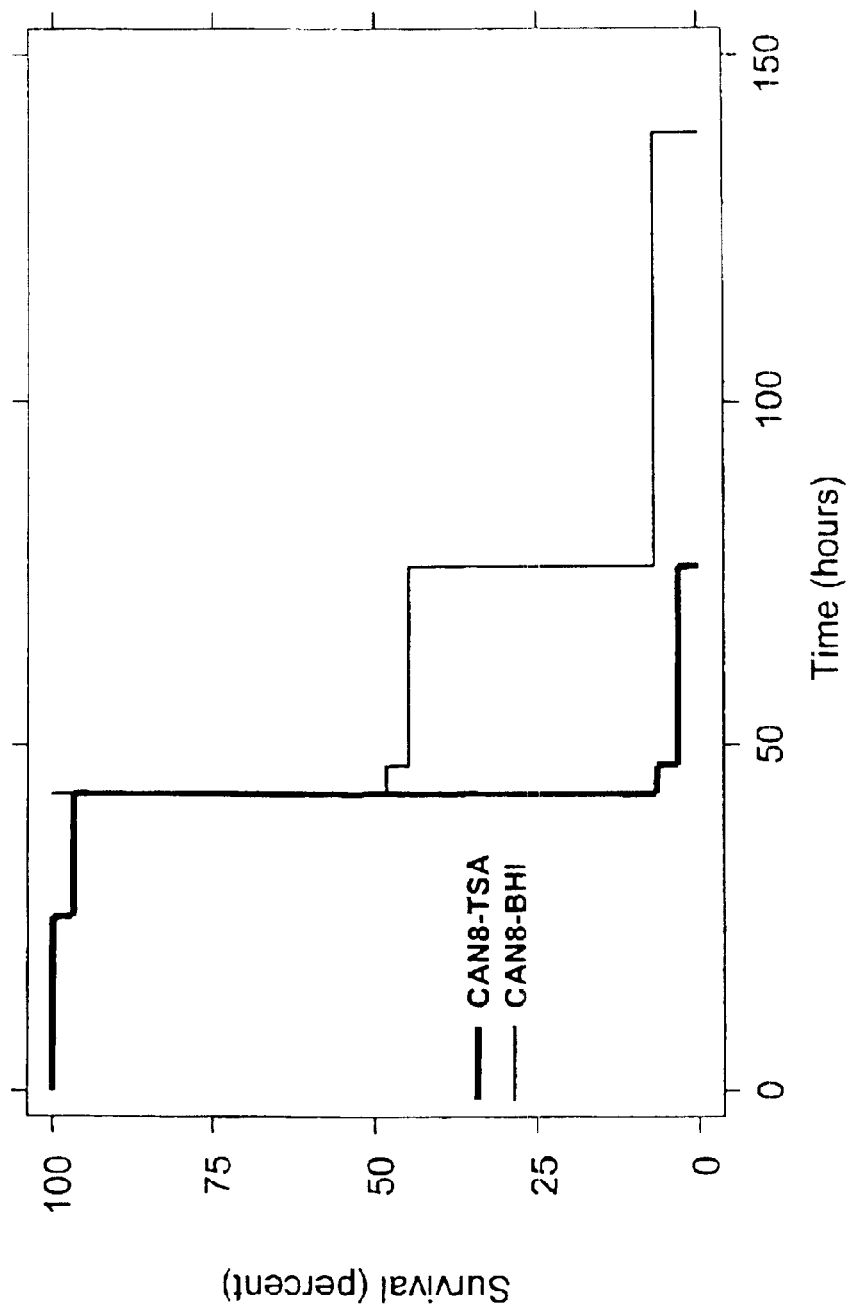
Figure 9B:
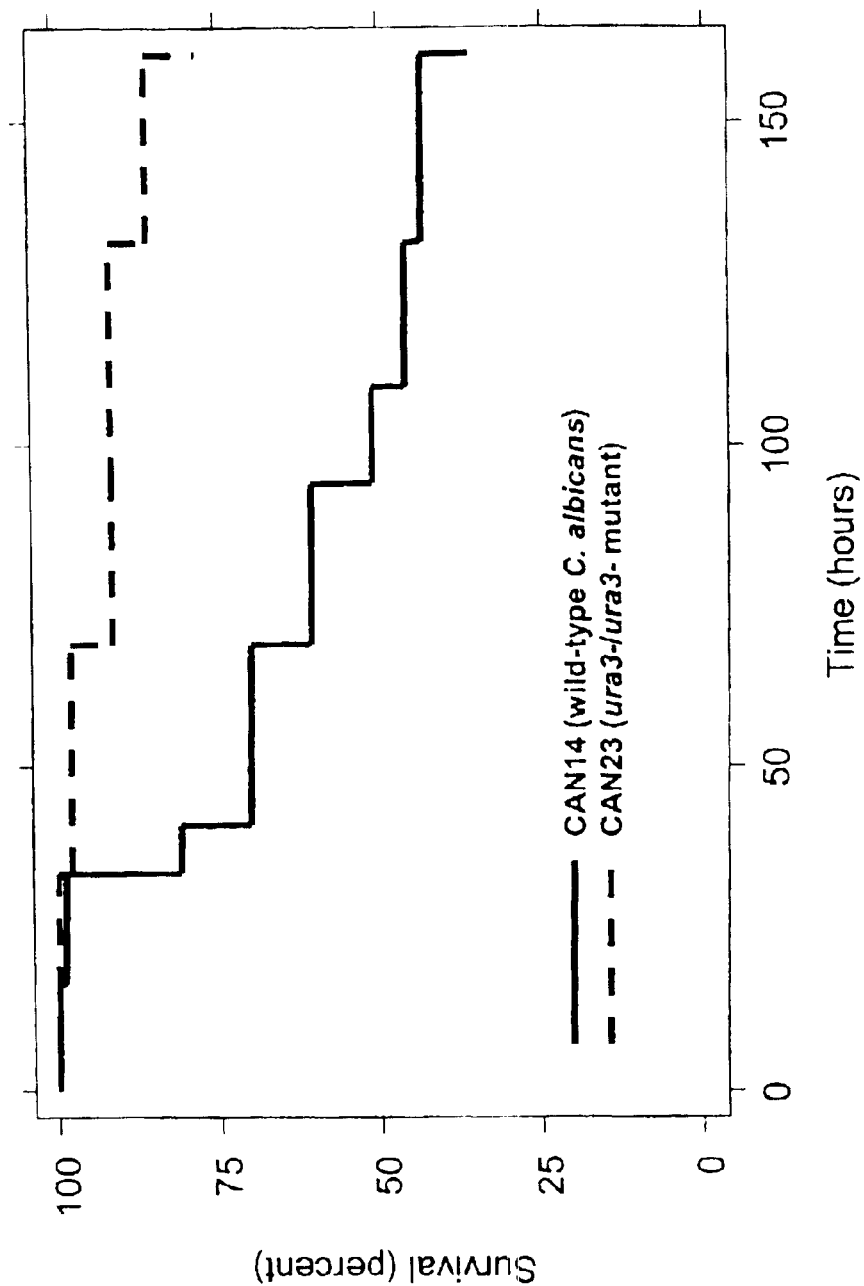

FIGS. 9A and 9B are graphs showing *C. elegans* killing on lawns of Candida. FIG. 9A shows *C. elegans* killing on lawns of *Candida glabrata* (CAN8) grown on tryptic soy agar (TSA) or brain heart infusion (BHI) agar plates. FIG. 9B is a graph showing that CAN23 (ura3-/ura3-), a uracil auxotroph, virulence is attenuated relative to CAN14 (SC5314), wild-type Candida.

Figure 10:
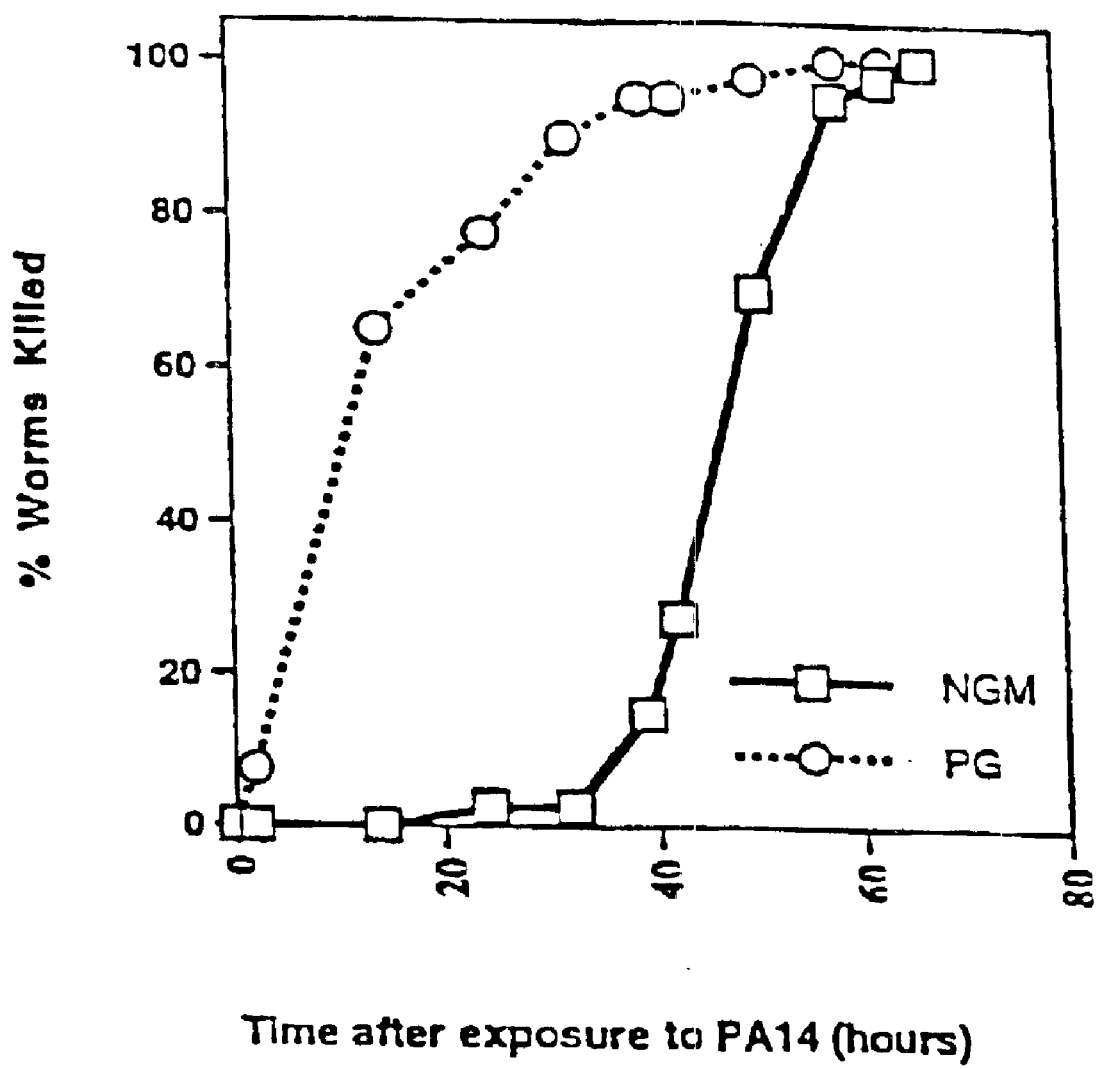

FIG. 10 illustrates the kinetics of the nematode fast and slow-killing assays. *P. aeruginosa* killed L4 worms more rapidly when they were grown on a low-phosphate peptone-glucose (PG) agar than on NGM agar. Forty L4 worms were exposed to PA14 grown on either PG (circles) or NGM (squares) and the percentages of worms killed are indicated as the mean of three replicates.

FIGS. 11A–11H are graphs showing that fast and slow killing utilize distinct mechanisms. The *P. aeruginosa* mutants, lasR (FIGS. 11A and 11B), gacA (FIGS. 11C and 11D), degP (FIGS. 11E and 11F) and 49H2 (FIGS. 11G and 11H) were compared to the parental wild-type PA14 for fast (left panels) and slow (right panels) killing. Both the lasR (triangles) and gacA (circles) mutants were debilitated in their abilities to kill worms compared to the wild-type PA14 (triangles) in slow killing (FIGS. 11B and 11D), but their pathogenicity was not compromised under fast killing conditions (FIGS. 11A and 11C). In contrast, a mutation in the degP gene (diamonds) was found to delay slow killing (FIG. 11F) and reduce fast killing (FIG. 11E). Mutant 49H2 (inverted triangles) displayed an opposite effect from the gacA and lasR mutants; it was indistinguishable from wild-type in slow killing (FIG. 11H) but dramatically reduced in fast killing (FIG. 11G). Each data point represents the mean±SD from three replicates. For fast killing experiments, bacteria were grown on either PGS (FIGS. 11A and 11G) or PG (FIGS. 11C and 11E) agar. All the slow killing experiments were carried out on NGM agar.

FIGS. 12A–12C are graphs showing that the efficacy of fast killing is species and strain dependent. FIG. 12A compares the fast killing among closely related fluorescent pseudomonads. *P. fluorescens* strain 2–79 (open diamonds) is as pathogenic as *P. aeruginosa* PA14 (open squares), but *P. syringae* pv. *syringae* strain 4326 is not pathogenic. FIG. 12B compares the virulence of different *P. aeruginosa* strains. PA14 is most virulent among the strains tested: 80% of the worms exposed to PA14 were killed after 12 hours. At the 12 hour time point, strains, PAK, PAO1-R, PO37, and PA29, accounted for less than 20% worm mortality. FIG. 12C compares the pathogenicity of PAO1 variants. No significant difference was seen between different laboratory collections of PAO1. Each data point represents mean±SD from three replicates. These experiments were carried out twice with similar results.

FIGS. 13A–13F are graphs showing the factors affecting *P. aeruginosa*-mediated killing of *C. elegans*: worm developmental stage (FIG. 13A) and environmental factors (FIGS. 13B–13F). Unless stated otherwise, all experiments were carried out using synchronized cultures of L4 stage wild-type N2 *C. elegans* grown at 20° C. The percentages of worms killed are mean±SD from four replicates. All plates were seeded with forty worms and were maintained at 25° C. FIG. 13A is a graph showing the kinetics of killing of L4 (squares) or one-day-old adults (diamonds) that were exposed to PA14 grown on PGS agar. FIG. 13B is a graph showing the effect of osmolarity on the fast killing response. Kinetics of killing of L4 worms exposed to PA14 grown on Peptone-Glucose medium with 0.15M sorbitol (closed squares), 0.1M sorbitol (closed triangles), or no sorbitol (closed circles). The addition of 0.15 M sorbitol significantly increased the rate of killing compared to 0.1 M or no sorbitol. The mean±SD was determined from four replicates. FIG. 13C is a graph showing the effect of iron concentration on the fast killing response. L4 worms were tested on PGS with either no additional iron (closed squares), the addition of 100 $\mu$M FeCl$_3$ (crossed circles), or the addition of 400 $\mu$M of an iron chelator EDDA (crossed squares). The rate of killing was significantly reduced in plates with added iron when compared to those plates with no additional iron or with the addition of an iron chelator. This experiment was performed three times with similar results. FIG. 13D is a graph showing the effect of temperature on the fast killing response. PA14 was grown on PGS agar plates for thirty-six hours at 20° C. (open squares), 25° C. (open diamonds), 30° C. (open circles), or 37° C. (open triangles) prior to the addition of one-day-old adult worms. Growth at 37° C. was found to reduce the rate of killing when compared to lower temperatures. A second experiment where PA14 was grown at the above temperatures for twenty-four hours showed a similar trend. FIGS. 13E and 13F are graphs showing the effect of carbon source on the fast killing response. Replacing the 1% glucose (half-filled squares) from the PGS medium with 1% glycerol (filled squares) resulted in a decrease in the killing rate of wild-type PA14 (FIG. 13E). However, the strain rpn7-lasR (filled circles) was observed to kill more rapidly than wild-type PA14 when glycerol was used as the carbon source instead of glucose (FIG. 13F). rpn7-lasR was also found to produce more pyocyanin than wild-type PA14 when glycerol was used as a carbon source.

FIGS. 14A–14B are histograms illustrating that fast killing is mediated by heat stable diffusible factors. Cultures of PA14 were grown on PGS agar plates for twenty-four hours prior to experimental treatments. Synchronized cultures of L4 stage wild-type N2 animals grown at 20° C. were used for all experiments. The percentages of worms killed are shown as the mean ±SD from three replicates. FIG. 14A shows that the fast killing response does not require live bacteria. Mortality of L4 worms in plates containing live PA14 bacteria and plates with dead bacteria were measured at four hours post-exposure (HPE). Live or chloroform-killed *E. coli* DH5α were used to control for the effect of chloroform treatment. Plates containing live PA14 or chloroform-killed PA14 showed the same efficacy of killing. None of the worms was killed in the live or chloroform-killed *E. coli* plates. FIG. 14B illustrates that the main factors mediating worm killing were heat stable. The efficacy of killing at four hours HPE for unheated plates (0 minutes) was compared to PA14-containing plates heated at 65° C. for thirty minutes or sixty minutes. Both the heat-treated plates were cooled to room temperature prior to the addition of worms. No significant differences in killing efficacy were seen among the three treatments, suggesting that the factors responsible for killing were stable for at least one hour at 65° C.

FIGS. 15A–15B are graphs showing that the P-glycoprotein worm mutant is highly sensitive to fast killing, but not to slow killing. Survival rates of the L4 stage P-glycoprotein double deletion strain NL130 [pgp-1 (pk17); pgp-3 (pk18)] (circles) were compared to the parental N2 strain (squares) on fast killing PG (FIG. 15A) and slow killing NGM (FIG. 15B) media. In both experiments, synchronized cultures of L4 stage worms grown at 20° C. were used. The percentages of worms killed are shown as the mean±SD from three replicates. Approximately forty L4 worms were added to each plate, and all the plates were incubated at 25° C. Similar results were obtained from two independent sets of experiments.

FIGS. 16A–16B are graphs showing that alginate is not important for fast killing. The rates of killing of the degP insertional mutant PA14degP (filled squares), the algD in-frame deletion mutant PA14algD 4 (filled circles), and the double mutant PA14degP algD 4 (filled triangles) were compared to wild-type PA14 (open squares) under fast killing (FIG. 16A) and slow killing (FIG. 16B) conditions. Approximately forty L4 N2 worms were added to each plate. The PGS agar was used for fast killing and NGM agar for slow killing. The percentages of worms killed are the mean±SD from three replicates.

Figure 17:
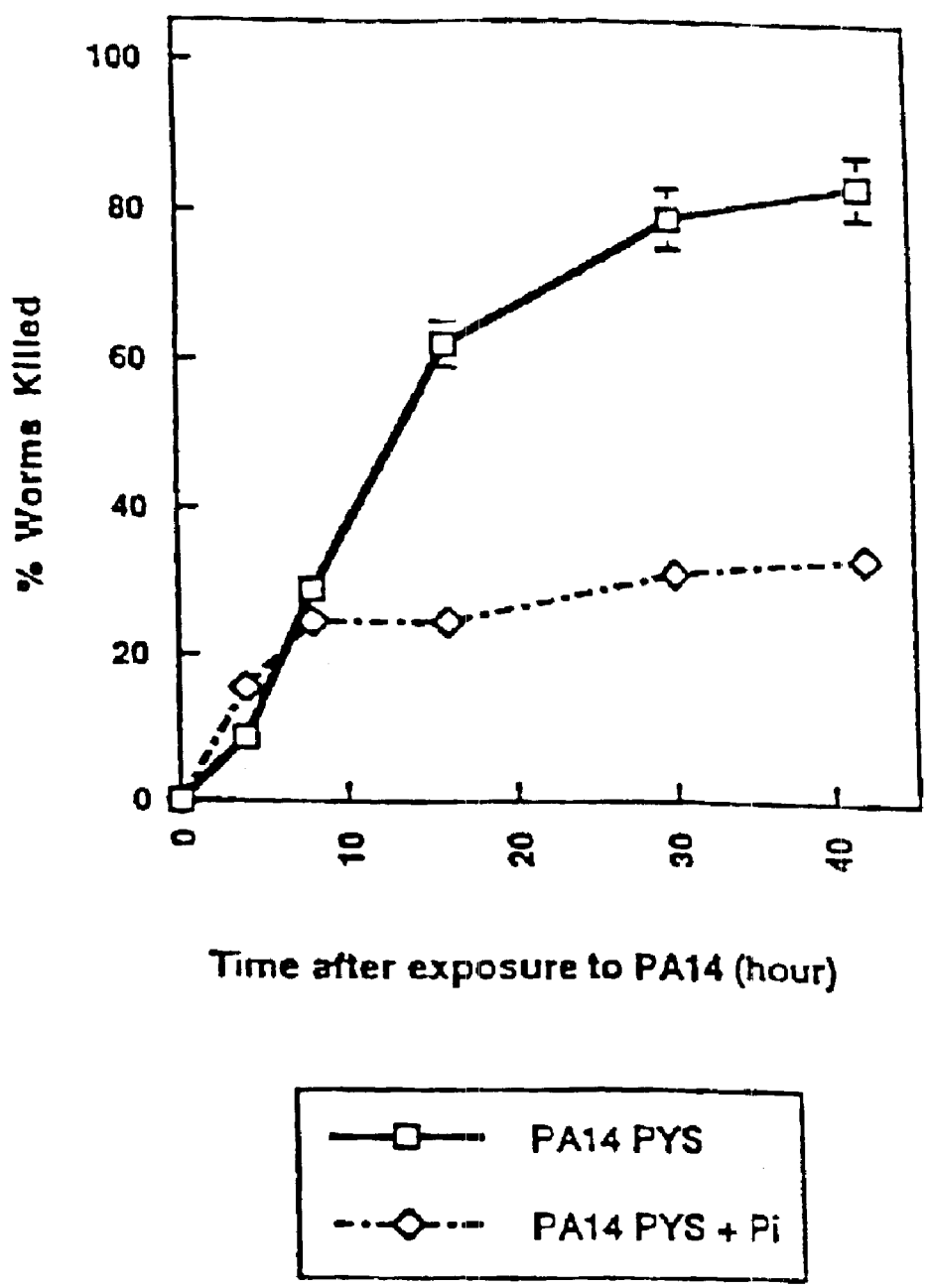

FIG. 17 is a graph showing that phosphate reduces the rate of fast killing. The rates of killing of PA14 grown on PYS agar with the addition of 20 mM inorganic phosphate (Pi) (diamonds) or without the addition of Pi (squares) were compared. The percentages of L4 worms killed (mean±SD from three replicates) after eight hours of exposure to PA14 were higher under phosphate-limiting conditions. Two independent experiments yielded similar results.

Figure 18:
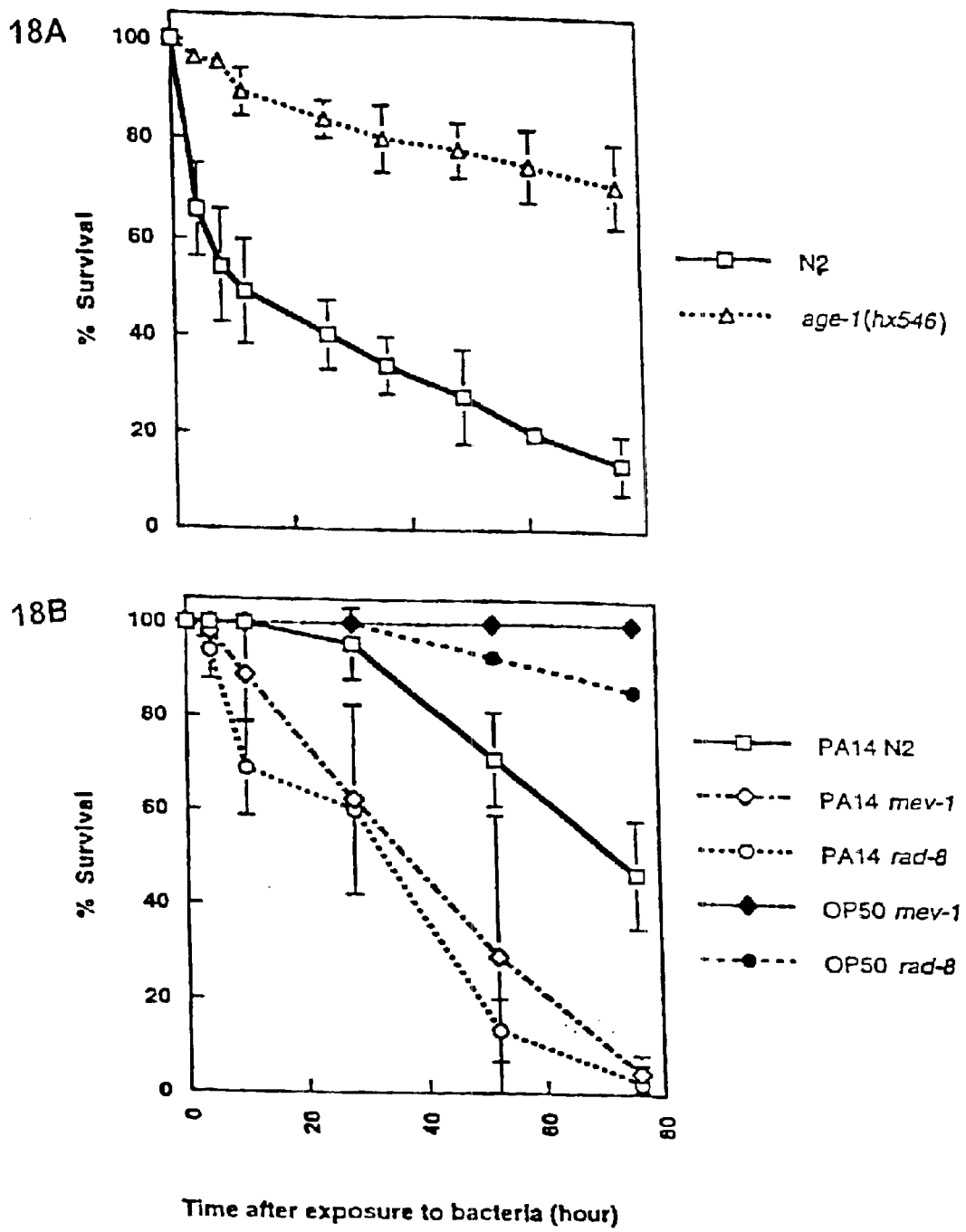

FIGS. 18A–18B are graphs showing that resistance to fast killing correlates with resistance to paraquat. Resistance or susceptibility of *C. elegans* strains TJ1052, age-1(hx546)II; TK22, mev-1(kn1)III; PH13, and rad-8(mn163)I were compared to the wild-type N2 strains under fast killing conditions. The percentages of survival are shown as the mean±SD from three replicates. FIG. 18A shows that a mutation in the age-1 gene confers resistance to PA14 fast-killing. The survival rates of L4 age-1(hx546) (open triangles) worms are significantly higher compared to N2 (open squares). FIG. 18B shows that mutations in the mev-1 and rad-8 genes result in increased sensitivity of PA14 fast killing. The survival rates of adult mev-1(kn1) and rad-8 (mn163) were tested on both PA14 and OP50. The OP50 control was used to control for any mortality due to oxygen toxicity; these mutants have been shown to have increased sensitivity to oxygen. Death on OP50 for both strains (filled diamonds and circles) was negligible. Both mev-1(kn1) (open diamond) and rad-8(mn163) (open circles) mutant adults were found to be more susceptible to fast killing as compared to their parent wild-type N2 strains (open squares).

Figure 19:
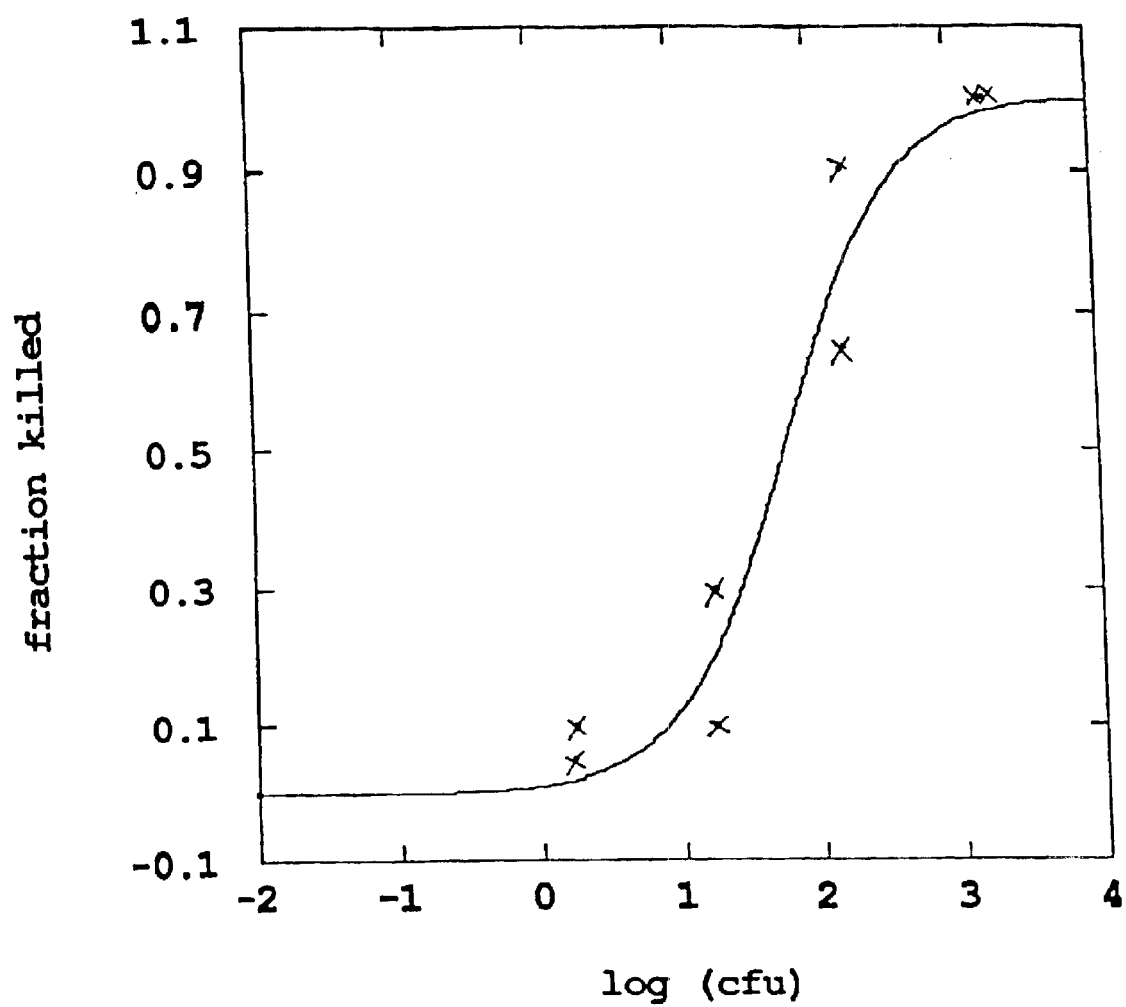

FIG. 19 is a graph showing the killing curve of *F. oxysporum* on *G. mellonella*.

Figure 20:
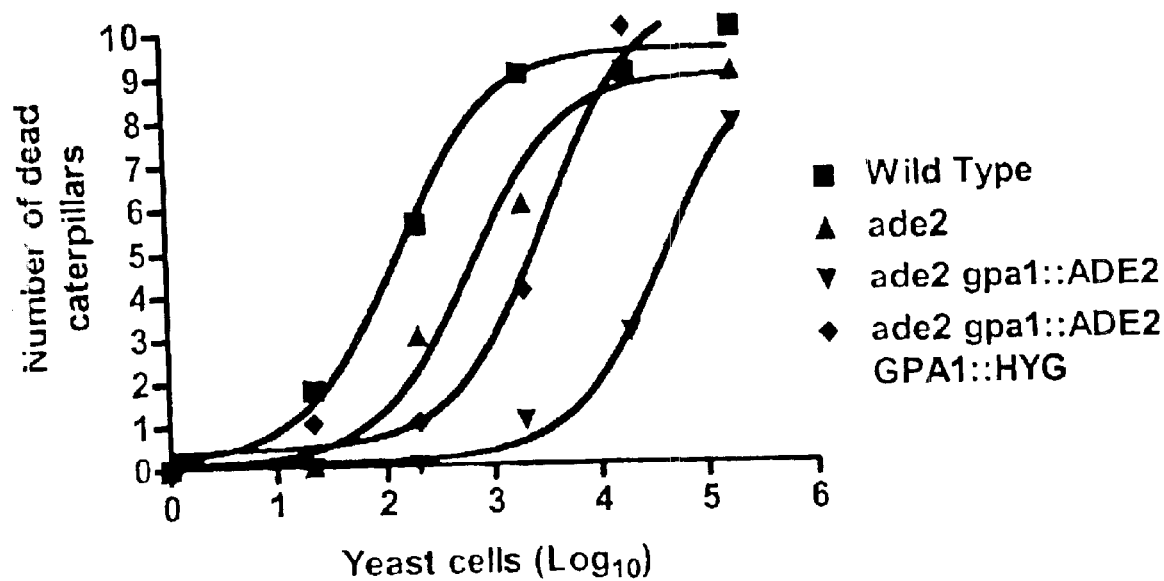

FIG. 20 is a graph showing the killing of *G. mellonella* by Cryptococcus.

Figure 21:
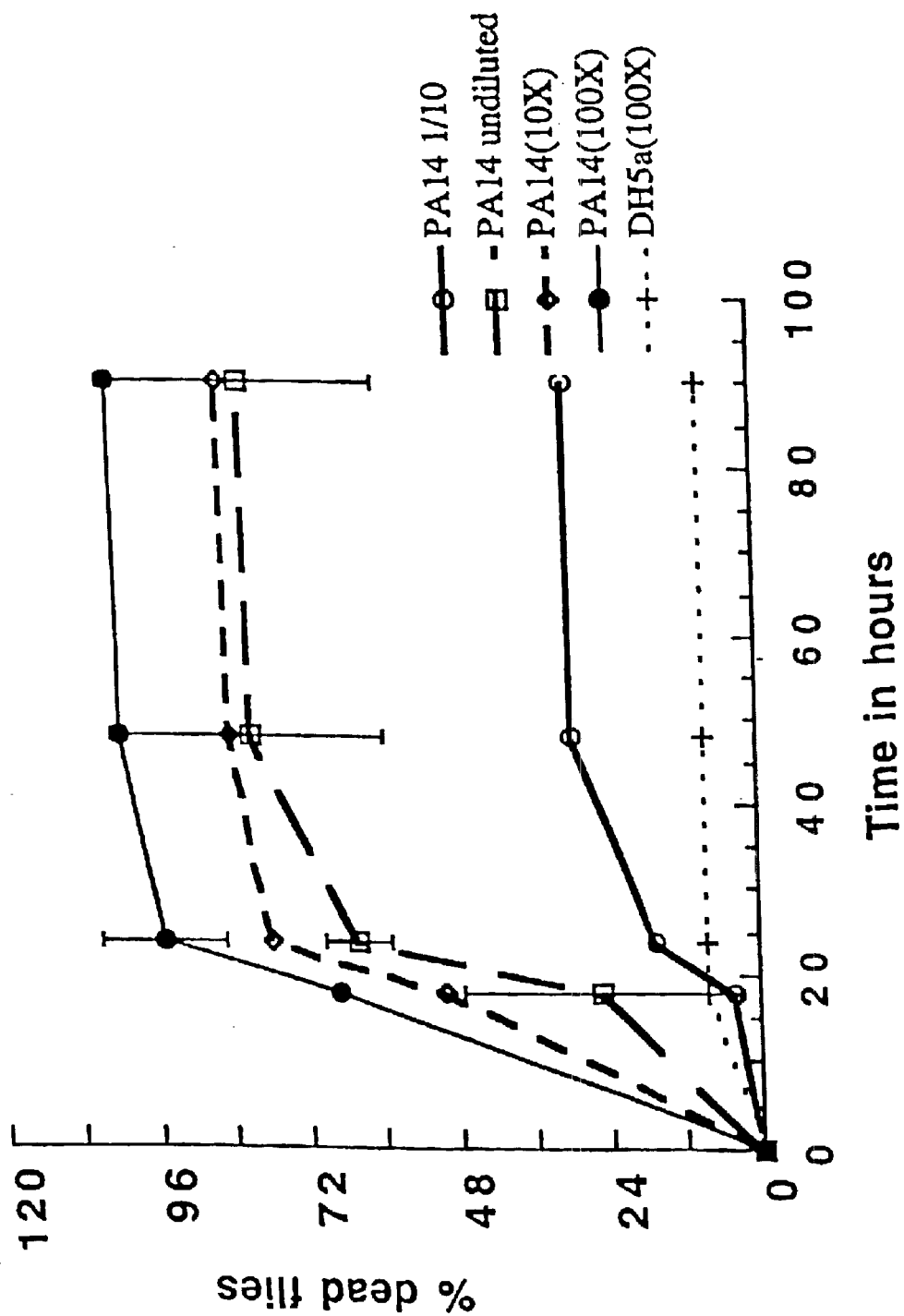

FIG. 21 is a graph showing the killing of Or$^R$ flies by PA14.

Below we describe experimental evidence demonstrating that a bacterial pathogen is capable of causing disease in a plant, in an animal, and in a nematode, and that there is an overlap in virulence factors responsible for causing microbial pathogenic disease in plants, animals, and nematodes. These experimental examples are intended to illustrate, not limit, the scope of the claimed invention.

Identification of Common Virulence Factors Required for *Pseudomonas aeruginosa* Pathogenicity in Plants and Animals To identify multi-host virulence factors, we first searched for bacterial pathogens capable of eliciting disease in both plant and animal pathogenesis models. A variety of *P. aeruginosa* isolates were screened using an *Arabidopsis thaliana* leaf pathogenesis infiltration system. Isolates which elicited disease symptoms in Arabidopsis were then tested for pathogenicity in a mouse full-thickness skin burn model and a nematode feeding assay.

Specifically, we first screened a collection of *P. aeruginosa* strains which included 30 human clinical isolates, 20 soil isolates, and 25 plant isolates (obtained from the University of California at Berkeley, Department of Plant Pathology). Each of these isolates was independently injected into the leaves of four different Arabidopsis ecotypes (land races or wild accessions) to determine whether the isolate was a plant pathogen. Several Arabidopsis ecotypes were assayed to increase the likelihood of identifying a suitable pathogen because plant pathogens, including Arabidopsis pathogens, typically exhibit a high level of host cultivar or ecotype specificity. Multiple host assays were also carried out because *P. aeruginosa* strains exhibiting ecotype specificity were more likely to be bonafide plant pathogens (rather than artifactual pathogens, capable of infecting plants only in the artificial environment created in the laboratory).

Screening experiments using an Arabidopsis leaf pathogenesis infiltration system were performed as follows. *P. aeruginosa* strains were grown in Luria Broth (LB) medium at 37 C, washed twice in 10 mM $MgSO_4$, resuspended at an optical density of 600 [$OD_{600}$]=0.2 in 10 mM $MgSO_4$, diluted 1:100 (corresponding to a bacterial density of $10^3$ cfu/$cm^2$), and injected into leaves of six week old Arabidopsis plants. Plants were kept in a growth chamber during the course of the experiment at 28–30° C. and 90–100% relative humidity. Disease symptoms and growth were monitored daily for five days. Symptoms elicited five days post-injection were characterized as: "none," no symptoms; "weak," localized weak water-soaking and chlorosis (yellowing) of tissue circumscribing the injection site; "moderate," moderate water-soaking and chlorosis with the majority of tissue softened around the inoculation site; or "severe," severe soft-rotting of the entire inoculated leaf characterized by a water-soaked reaction zone and chlorosis circumscribing the injection site at 2–3 days post-injection. The soft-rot symptoms pervaded the leaf at 4–5 days post-injection. Leaf intercellular fluid containing bacteria was harvested at five days, and bacterial counts were determined according to standard methods (see, e.g., Dong et al. (1991) *Plant Cell* 3:61). Four different samples were taken using two leaf discs per sample. Three independent experiments gave similar results. Control plants inoculated with 10 mM $MgSO_4$ showed no symptoms during the course of the experiments. In other control experiments, none of the genetically characterized *P. aeruginosa* strains PAK, PAO1, or PO37 caused appreciable symptoms on any of the Arabidopsis ecotypes tested. These strains were found to be non-pathogenic in the ecotypes tested, but pathogenic in culture.

While the majority of the 75 *P. aeruginosa* strains which were screened caused no symptoms in Arabidopsis leaves, several strains elicited weak to moderate soft-rot symptoms characterized by chlorosis and water-soaking of the tissue circumscribing the injection site. Two strains, UCBPP-PA14 (a human clinical isolate) and UCBPP-PA29 (a plant isolate) caused severe soft-rot symptoms in some of the ecotypes tested, typical of a highly virulent plant bacterial pathogen. Table I shows the growth of *P. aeruginosa* UCBPP-PA14 and UCBPP-PA29 five days post infection, and disease symptoms elicited by these *P. aeruginosa* strains on different Arabidopsis ecotypes. In particular, strain UCBPP-PA14 caused severe soft-rotting in both the Llagostera (Ll) and Columbia (Col) Arabidopsis ecotypes, but caused no symptoms in ecotype Argentat (Ag) and only moderate symptoms in ecotype Bensheim (Be). Table I also illustrates that strain UCBPP-PA29 caused severe symptoms in Ll and weak symptoms in Col, but caused no symptoms in Ag or Be.

TABLE I

| Arabidopsis Ecotype | *P. aeruginosa* UCBPP-PA14 cfu/$cm^2$ leaf area | Symptoms | *P. aeruginosa* UCBPP-PA29 cfu/$cm^2$ leaf area | Symptoms |
| --- | --- | --- | --- | --- |
| Llagostera | $2.6 \times 10^7 \pm 2.0 \times 10^7$ | Severe | $2.7 \times 10^7 \pm 1.3 \times 10^7$ | Severe |
| Columbia | $9.0 \times 10^6 \pm 6.0 \times 10^6$ | Severe | $6.0 \times 10^5 \pm 3.0 \times 10^5$ | Weak |
| Argentat | $3.0 \times 10^5 \pm 1.4 \times 10^5$ | None | $1.5 \times 10^5 \pm 9.0 \times 10^4$ | None |
| Bensheim | $1.1 \times 10^6 \pm 4.9 \times 10^5$ | Moderate | $4.5 \times 10^5 \pm 2.0 \times 10^5$ | None |

Figure 1:
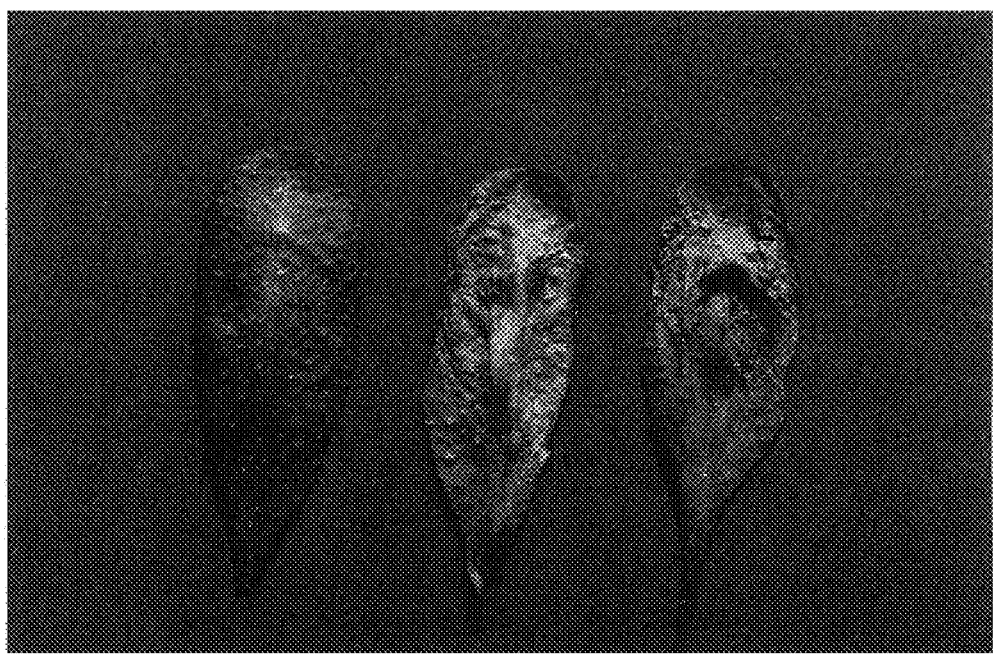

As shown in FIG. 1, the severe symptoms elicited by UCBPP-PA14 (far right) were characterized by a water-soaked reaction zone and chlorosis, resulting in complete maceration and collapse of the leaf 4 to 5 days post-infection (compare with control far left). These symptoms were essentially indistinguishable from the symptoms elicited by the highly virulent Arabidopsis pathogen *Pseudomonas syringae* pv. maculicola strain ES4326 (pictured in center).

To verify that the severity of disease symptoms was correlated with bacterial proliferation, growth of each of the strains UCBPP-PA14 and UCBPP-PA29 was measured over the course of several days in Arabidopsis leaves as described above. As shown in FIG. 2A, strains UCBPP-PA14 (open circles) and UCBPP-PA29 (open triangles) reached maximal bacterial density of approximately $10^7$ cell/$cm^2$ leaf area by five days in ecotype Ll, which corresponded to $10^4$-fold increases from the initial inocula. The growth profiles of these strains in Ll was similar to that of the virulent Arabidopsis pathogen *P. syringae* pv. maculicola strain ES4326 (FIG. 2A, open squares). Strain UCBPP-PA14 also proliferated $10^4$-fold in ecotype Col (FIG. 2B, solid squares; Table I). In contrast, strain UCBPP-PA14 increased only $10^3$- and $10^2$-fold in Be and Ag leaves, respectively (FIG. 2B, solid triangles and solid circles, respectively; Table I), and strain UCBPP-PA29 increased only $10^2$- to $6 \times 10^2$-fold in ecotypes Col, Ag, and Be (Table I). In each case, reduced bacterial counts in leaves reflected less severe symptom development. Accordingly, each of these *P. aeruginosa* strains was similar to other phytopathogenic bacteria in its ability to cause disease in an ecotype-specific manner.

UCBPP-PA14 and UCBPP-PA29 isolates found to elicit disease symptoms in Arabidopsis were then tested in a mouse full-thickness skin burn injury assay. This involves 5% of the murine body surface area fashioned on an outstretched area of abdominal skin (Stevens et al. (1994) *J. of Burn Care and Rehabil.* 15:232). In this model, the damaged epidermis and dermis undergoes coagulation necrosis, but the underlying rectus abdomini (RA) muscles are not injured. In the absence of infection, all animals survive.

To carry out this pathogenesis assay, a *P. aeruginosa* inoculum is injected intradermally into the midline crease of the burn eschar. The bacteria proliferate in the burn wound, and some strains may invade the normal underlying RA muscles. Highly pathogenic strains can also invade the vasculature. The number of bacteria found in the RA muscles underlying and adjacent to the burn after 24 hours gives a quantitative measure of local invasiveness, and mortality indicates both local and systemic invasiveness.

Mouse full-thickness skin burn studies were performed as follows. Six week old male CD-1 mice (Charles River Animal Farms) weighing between 25 and 35 grams were used in all experiments, following an animal burn model (Stevens et al., supra). Mice were injected with $\sim 5 \times 10^3$ cells. No viable bacterial cells were retrieved from the underlying RA muscle immediately after bacterial injection or in animals who received a sham injury in other studies. In mortality studies, immediately following the burn, mice were injected with $10^2$ cells, and the number of animals which died of sepsis was monitored each day for ten days. Two groups of control animals consisting of (i) mice burned but not injected and (ii) mice injected with heat-killed UCBPP-PA14 resulted in 0% mortality.

Data shown in Table II (below) illustrate the proliferation of *P. aeruginosa* strains in a mouse full-thickness skin burn model. Table II indicates that strains UCBPP-PA14 and UCBPP-PA29 proliferated and invaded the RA muscles comparably to the well-characterized *P. aeruginosa* human isolates PO37, PAK, and PAO1. All strains reached titers ranging from $1.8 \times 10^8$ to $3.6 \times 10^8$ cfu per gram tissue in RA muscle biopsies taken directly beneath the burn and infection site (Table II). Furthermore, all strains reached titers ranging from $4.0 \times 10^7$ to $8.2 \times 10^7$ cfu per gram tissue in RA muscle biopsies taken adjacent to the burn. In addition, tissue samples processed for routine histology revealed that strain UCBPP-PA14 invaded the muscle to the same degree as strain PO37.

TABLE II

| *P. aeruginosa* Strain | Mean titer ± S.D. in biopsies underneath burn | Mean titer ± S.D. in biopsies adjacent to burn |
| --- | --- | --- |
| UCBPP-PA14 | $20.0 \times 10^7 \pm 9.0 \times 10^7$ | $6.0 \times 10^7 \pm 2.1 \times 10^7$ |
| UCBPP-PA29 | $36.0 \times 10^7 \pm 10.0 \times 10^7$ | $8.2 \times 10^7 \pm 2.0 \times 10^7$ |
| PO37 | $30.0 \times 10^7 \pm 11.0 \times 10^7$ | $5.8 \times 10^7 \pm 1.0 \times 10^7$ |
| PAK | $18.0 \times 10^7 \pm 9.1 \times 10^7$ | $6.0 \times 10^7 \pm 1.2 \times 10^7$ |
| PAO1 | $31.0 \times 10^7 \pm 10.0 \times 10^7$ | $4.0 \times 10^7 \pm 1.8 \times 10^7$ |

The virulence of strains UCBPP-PA14 and UCBPP-PA29 in comparison to PO37 was also assessed by conducting mortality studies in the mouse full-thickness skin burn model as described above. Strains UCBPP-PA14, UCBPP-PA29, and PO37 caused 77% (17/22), 6% (1/16), and 22% (2/9) mortality, respectively, by the tenth day post-burn and infection (Table III). Additional experiments showed strains PA01 and PAK caused significantly less mortality in this model than UCBPP-PA14.

Strain UCBPP-PA14 was then selected for additional studies because it was infectious in both plant and animal pathogenicity models in which the outcome of pathogenesis could be quantitated, and because the level of virulence in these models was comparable to known plant and animal pathogens. Specifically, we sought to determine whether there were common virulence determinants in strain UCBPP-PA14 required for pathogenicity in both hosts. Our strategy was to use a marker exchange procedure to generate UCBPP-PA14 mutants carrying insertion mutations in four different genes, two known to be virulence determinants for *P. aeruginosa* in animal hosts, one known to be a virulence determinant for phytopathogenic bacteria in plant hosts, and one known to be a virulence determinant for several animal bacterial pathogens in animal hosts. The two animal virulence genes of *P. aeruginosa* were plcS and toxA encoding the exported proteins phospholipase C and exotoxin A, respectively (Ohman et al. (1980) *Infect. Immun.* 28: 899; Ostroff et al. (1987) *J. Bacteriol.* 169: 4597). Exotoxin A ribosylates G proteins, and phospholipase C preferentially degrades phospholipid of eukaryotic cells (Iglewski et al. (1975) *Proc. Natl. Acad. Sci.* 72:2284; Berka et al. (1982) *J. Bacteriol.* 152:239). The plant pathogen virulence determinant was gacA, identified as a global regulator of excreted anti-fungal factors in the non-pathogenic soil bacterium *P. fluorescens* (Laville et al. (1992) *Proc. Natl Acad. Sci.* 89:1562; Gaffney et al. (1994) *Mol. Plant-Microbe Interact.* 7:455). In the phytopathogens *P. syringae* pv. *syringae* and *P. cichorii*, gacA appears to serve as a transcriptional regulator of genes that encode extracellular products involved in pathogenicity (Rich et al. (1994) *J. Bacteriol.* 176:7468). The other animal virulence determinant, degP (also known as htrA), has been identified as a stress-response protease which is responsible for degrading incorrectly folded periplasmic proteins in Brucella and Salmonella (Elzer et al. (1994) *Infect. Immun.* 62: 4135; Johnson et al. (1991) *Mol. Microbiol.* 5: 410).

The UCBPP-PA14 homologues of plcS and toxA were identified in a genomic cosmid library of strain UCBPP-PA14 using cloned DNA fragments corresponding to the plcS and toxA genes of *P. aeruginosa* strain PAK as hybridization probes. A genomic library of strain UCBPP-PA14 was prepared according to standard methods in the cosmid cloning vector pJSR1, which was itself constructed by ligating a 1.6 kb BglII fragment containing the bacteriophage lambda cos site from pHC79 (see, e.g., Hohn et al. (1980) *Gene* 11: 291) into the BglII site of pRR54 (see, e.g., Roberts et al. (1990) *J. Bacteriol.* 172: 6204). A 1.7 kb BamH1 fragment isolated from plasmid pMS150 containing the toxA gene (see, e.g., Lory et al. (1983) *Gene* 22:95) and a 3.0 kb BamH1-PstI fragment isolated from plasmid pSL2 (see, e.g., Lory et al. (1988) *J. Bacteriol.* 170:714) containing the plcS gene were used to probe the UCBPP-PA14 genomic library in pJSR1.

The UCBPP-PA14 homologue of gacA was identified in the same cosmid library using a PCR-amplified product corresponding to a conserved region of the *P. fluorescens* gacA gene according to standard methods. The oligonucleotides 5'-GCTAGTAGTCGATGACC-3' (SEQ ID NO:1) and 5'-GCTGGCATCAACCATGC-3' (SEQ ID NO:2) were designed on the basis of the sequence of the gacA gene (Laville et al. (1992) *Proc. Natl. Acad. Sci.* 89:1562) and used to amplify a 625 base-pair product containing the gacA gene of *Pseudomonas fluorescens*, which in turn was used to probe the UCBPP-PA14 genomic library in pJSR1 described above. The UCBPP-PA14 homologue of the degP gene was identified in the UCBPP-PA14 cosmid library using the degP gene of *Pseudomonas syringae* pv. maculicola as a probe.

All four genes were subcloned and mutagenized by the insertion of a cassette encoding gentamicin resistance using standard methods.

In addition, a 6 kb BamHI fragment isolated from the cosmid clone containing the plcS gene of strain UCBPP-PA14 was subcloned from a pJSR1-derived cosmid into the BamHI site of pBR322. The resulting clone, pLGR101, was mutagenized by insertion of a gentamicin-encoding DNA cassette into the XhoI site of the plcS gene to construct pLGR201. The gentamicin-resistance gene cassette is a 1.8 kb BamHI fragment from plasmid pH1JI (see, e.g., Rubin (1987) Plasmid 18:84). A 1.6 kb BamHI fragment containing the toxA gene was subcloned from a pJSR1-derived cosmid into pBR322 to construct pLGR102 and subsequently mutated by introducing the gentamicin cassette into the BglII site of the toxA gene to construct plasmid pLGR202. And a 2.5 kb HindIII-EcoRI fragment containing the P. aeruginosa strain UCBPP-PA14 gacA gene was subcloned from a pJSR1-derived cosmid into pBR322 to construct pLGR103. The presumptive gacA gene was partially sequenced to confirm that the UCBPP-PA14 gacA had been cloned. pLGR103 was mutagenized by inserting the gentamicin cassette into the SalI site of gacA to construct the plasmid pLGR203. A 1.6 Pst I fragment containing part of the degP gene was subcloned from pPY201 a derivative of the cosmid clone pH126 of the strain UCBPP-PA14 into the PstI site of pUC19 to construct pNAS. A 1.6 kb SalI fragment containing the gentamicin cassette was inserted into the XhoI site of the degP gene in pNAS to construct pNASGm. Next, a 3.2 kb SphI/XhoI fragment was isolated from the pNASGm vector and subcloned into the SphI/XhoI sites of pCVD442 to construct pPY206, which contained the mutated degP gene.

The mutated genes were transferred to the UCBPP-PA14 genome using standard marker exchange techniques, and the structures of the resulting marker exchange mutations were verified by DNA blot analysis. Thus, plasmids pLGR201, pLGR202, pLGR203, and pPY206 were used for gene replacement of the plcS, toxA, gacA, and degP genes respectively, by the method described in Rahme et al. (J. Bacteriol. 170:575, 1991) using gentamicin at 30 mg/mL to screen for the double crossover events and carbenicillin at 300 mg/mL to screen for the loss of the vector. None of these four mutations had any detectable effect on the growth of the bacteria compared to wild-type in either rich or minimal media.

The effects of the plcS, toxA, gacA, and degP mutations on the pathogenicity of UCBPP-PA14 in the Arabidopsis model were tested by infiltrating the mutant strains into Arabidopsis ecotype Ll. Unlike wild-type UCBPP-PA14, none of the mutants caused maceration or collapse of the leaf. Specifically, the isogenic toxA mutant caused attenuated soft-rot and chlorosis symptoms without the accompanying maceration of the affected tissue characteristic of UCBPP-PA14. The plcS, gacA, and degP mutants elicited even weaker symptoms, causing only chlorosis. Consistent with the attenuated symptoms, growth of the toxA, plcS, gacA, and degP mutants after 5 days was approximately 10-fold, $10^2$-fold, $5 \times 10^3$-fold, and $10^2$-fold less, respectively, than the growth of the wild type (FIGS. 2C and 2D).

The growth and symptoms of the three mutants tested (plcS, toxA, and gacA) were fully restored to wild-type levels in plants when these mutants were complemented with the corresponding wild-type genes carried on a plasmid. This was accomplished by subcloning a 6 kb BamH1 fragment from the cosmid clone pB85 of the genomic library containing the plcSR operon of strain UCBPP-PA14 into the BamHI site of plasmid pRR54 to construct pLGR301. Plasmid pLGR301 was then used for the genetic complementation studies of the plcS mutant. A 2.4 kb EcoRI/EcoRV fragment isolated from plasmid pMS150 containing the toxA gene of the strain PAK, was subcloned into the EcoRI/EcoRV sites of plasmid pBR322 to construct pLGR106. From pLGR106 a SphI/PstI fragment containing toxA was cloned into the SphI/PstI sites of pRR54 to construct pLRG206. A 1.2 kb HindIII/XhoI fragment containing the gacA gene was isolated from cosmid clone pH106 and subcloned into the HindIII/SalI sites of plasmid pRR54 to construct pLGR204. Plasmids pLRG206 and pLGR204 were then used for genetic complementation studies of the toxA and gacA mutants.

Table III shows lethality studies corresponding to these three mutant P. aeruginosa strains in a mouse full-thickness skin burn model. In such lethality studies, mice that were burned and infected with either plcS or toxA mutants exhibited significantly lower mortality (40% with both mutants) compared to infection with the wild-type strain (77%). The gacA and degP mutants caused no mortality (Table III). The differences in mortality rates between the mutants and wild-type was statistically significant at the 95% or greater confidence level. Statistical significance for mortality data was determined by using the chi-square test with Yates' correction. Groups were considered statistically significant at $P \leq 0.05$. All the mutants achieved statistical significance (plcS and toxA, P=0.05; gacA, P=0.00005).

TABLE III

| P. aeruginosa Strain | Mortality ratio of mice at 10 days following burn and infection |
| --- | --- |
| UCBPP-PA14 | 17/22 |
| UCBPP-PA14 plcS | 6/15 |
| UCBPP-PA14 toxA | 6/15 |
| UCBPP-PA14 gacA | 0/10 |
| UCBPP-PA14 degP | 0/11 |
| UCBPP-PA29 | 1/16 |
| PO37 | 4/9 |

The above results demonstrate that plcS, toxA, gacA, and degP are involved in both plant and animal pathogenesis and indicate a part of the pathogen's machinery required for disease development is common or shared in animal and plant hosts. One of the shared virulence factors, gacA, is active at the regulatory level, demonstrating that mechanisms for regulation of virulence factors are conserved between plant and animal pathogens. The plcS and toxA gene products are specific virulence determinants which presumably attack the membranes and inhibit protein synthesis in both plant and animal cells, respectively.

To extend these results to a third host system, the pathogenicity of P. aeruginosa UCBPP-PA14 was measured in a nematode feeding assay. The feeding assay was set up as follows. First, 5 µl of an overnight culture of P. aeruginosa UCBPP-PA14, or an isogenic strain of P. aeruginosa UCBPP-PA14 carrying a degP or gacA mutation, was inoculated onto the center of an NGM agar plate and cultured for 24 hours at 37° C. After several hours of cooling at room temperature, the plates were seeded with eight Caenorhabditis elegans L4-stage worms. Plates were subsequently incubated in the dark at 25° C., and deceased worms were scored every 6 hours. A worm is considered dead when it is non-motile, no longer displays any pharyngeal pumping action, and no longer exhibits defecation behavior.

Figure 3:
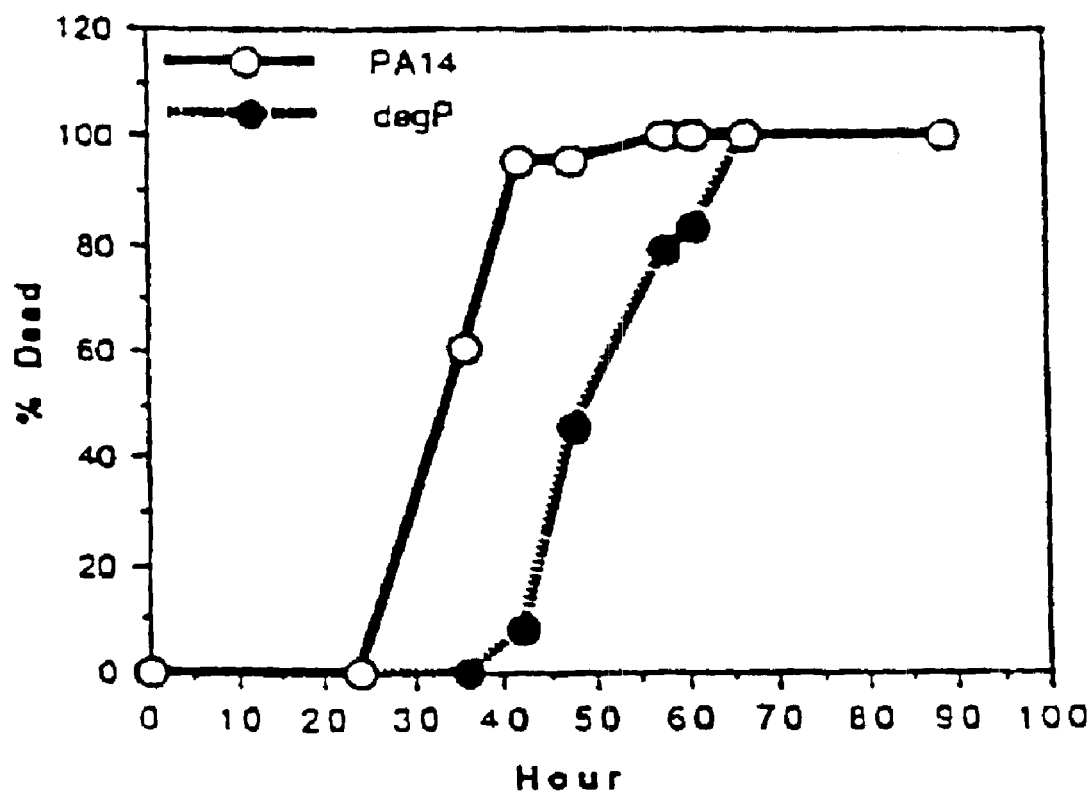
FIG. 3 is a graph showing a comparison of *Caenorhabditis elegans* lethality growing on wild-type *Pseudomonas aeruginosa* strain UCBPP-PA14 and on an isogenic degP mutant.
Figure 4:
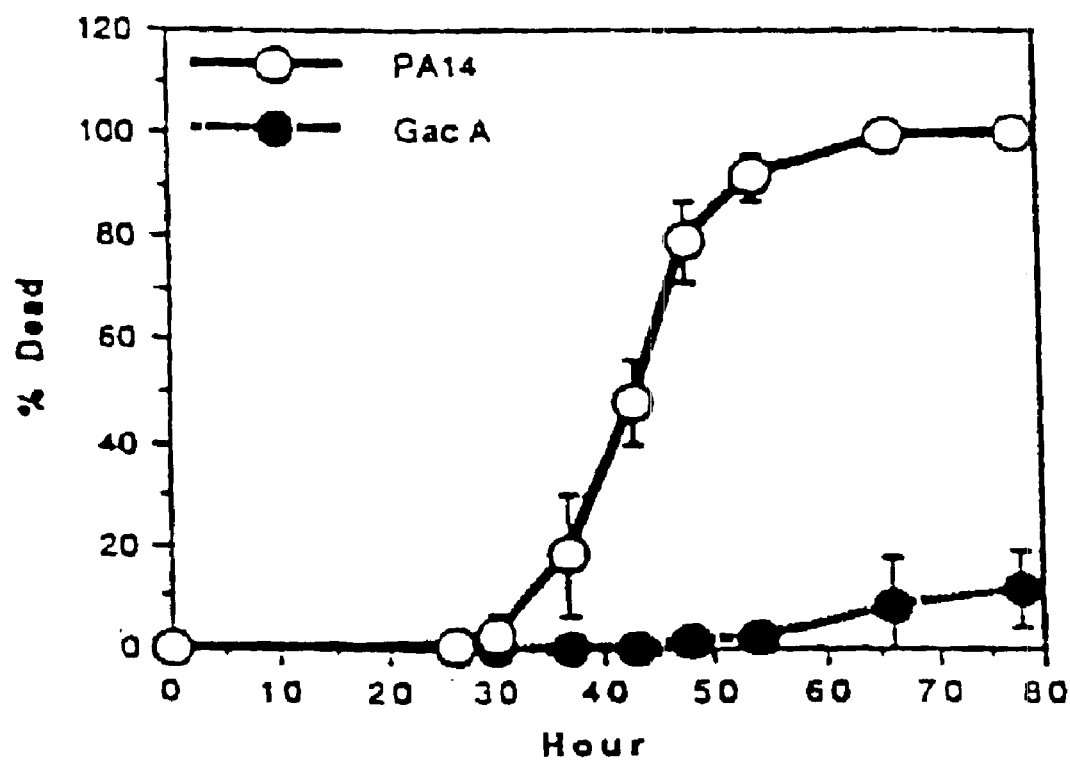
FIG. 4 is a graph showing a comparison of *Caenorhabditis elegans* lethality growing on wild-type *Pseudomonas aeruginosa* strain UCBPP-PA14 and on an isogenic gacA mutant.

FIGS. 3 and 4 show the results of the nematode feeding lethality assay using wild-type UCBPP-PA14 and its degP and gacA isogenic mutants, respectively. The results depicted in both FIG. 3 and FIG. 4 show that P. aeruginosa UCBPP-PA14 kills C. elegans. The results also show that isogenic mutants of P. aeruginosa UCBPP-PA14 carrying insertions which functionally disabled either the degP or gacA gene were significantly reduced in virulence in both the nematode and mouse full-thickness skin burn assay (FIGS. 3 and 4; Table III). The gacA gene is known to be a virulence determinant for *P. syringae* in plant hosts, and degP is known to be a virulence factor for both *P. syringae* and *Salmonella typhimurium*. As is discussed below, we have used these screening methods for identifying several mutants that exhibit reduced pathogenicity in nematodes and Arabidopsis; three of the mutants we isolated were found to be less pathogenic in mice.

Identification of Common Virulence Factors Required for *Cryptococcus neoformans* Pathogenicity in Plants and Animals In addition to the results described above with the bacterial pathogen, *P. aeruginosa*, the pathogenicity of a yeast fungus, *Cryptococcus neoformans*, has also been studied in both animal (nematode and mouse) and plant systems.

Killing of *C. elegans* by Cryptococci

We evaluated killing of *C. elegans* by various strains of *C. neoformans*, including *C. neoformans* serotype A (ATCC Nos. 208821, 62067, and 62070), serotype B/C (ATCC No. 56995) and serotype D (ATCC Nos. 36556 and 24067) and environmental isolates of *C. neoformans* (ATCC Nos. 14116, 34870, 32308, 32045, and 62068) (obtained from the American Type Culture Collection (ATCC), Manassas, Va.). *C. elegans*, at the L4 stage of development, were transferred from plates containing *E. coli* OP50 to test plates containing yeast lawns. Lawns of yeast were grown as follows: 2 ml of YPD (Yeast extract Peptone Dextrose media) was inoculated with a single colony of the appropriate yeast strain and grown at 28° C. for forty-eight hours. 10 $\mu$l of culture was spread on each 35-mm tissue-culture plate (Falcon) containing brain heart infusion (BHI) agar (Difco). Plates were then incubated at 28° C. overnight. Ampicillin (100 $\mu$/ml) or gentamicin (25–50 $\mu$/ml) was added to the medium to prevent the growth of *E. coli* OP50. The worms were incubated on the yeast lawns at 25° C., and then assayed at twenty-four hour intervals for viability. Under a dissecting scope, worms were assayed for touch sensitivity. Worms that failed to respond to a touch with a platinum wire pick were considered to be dead. Each experimental condition was tested in duplicate or triplicate. Contrary to our results with *C. neoformans*, nematodes exposed to *C. laurentii* (ATCC Nos. 18803, 66036, or 76483) or *C. kuetzingii* (ATCC No. 42276) produced progeny. Because it is difficult to distinguish progenitors from their growing progeny, we transferred the original progenitor *C. elegans* to new plates every forty-eight to seventy-two hours. Killing curves were plotted with the Kaplan-Meier method using STATA 6 statistical software (Stata, College Station, Tex.). The same software was used for testing equality of killing using log-rank and Wilcoxon statistical tests. P values of <0.05 were considered statistically significant.

Encapsulated *C. laurentii* and non-capsule forming *C. kuetzingii* produced colonies that allowed us to monitor the survival of nematodes. The control cryptococci that we tested, *C. laurentii* and *C. kuetzingii*, were not pathogenic to *C. elegans*, and nematodes were able to produce progeny when exposed to these nonpathogenic cryptococci.

Figure 5:
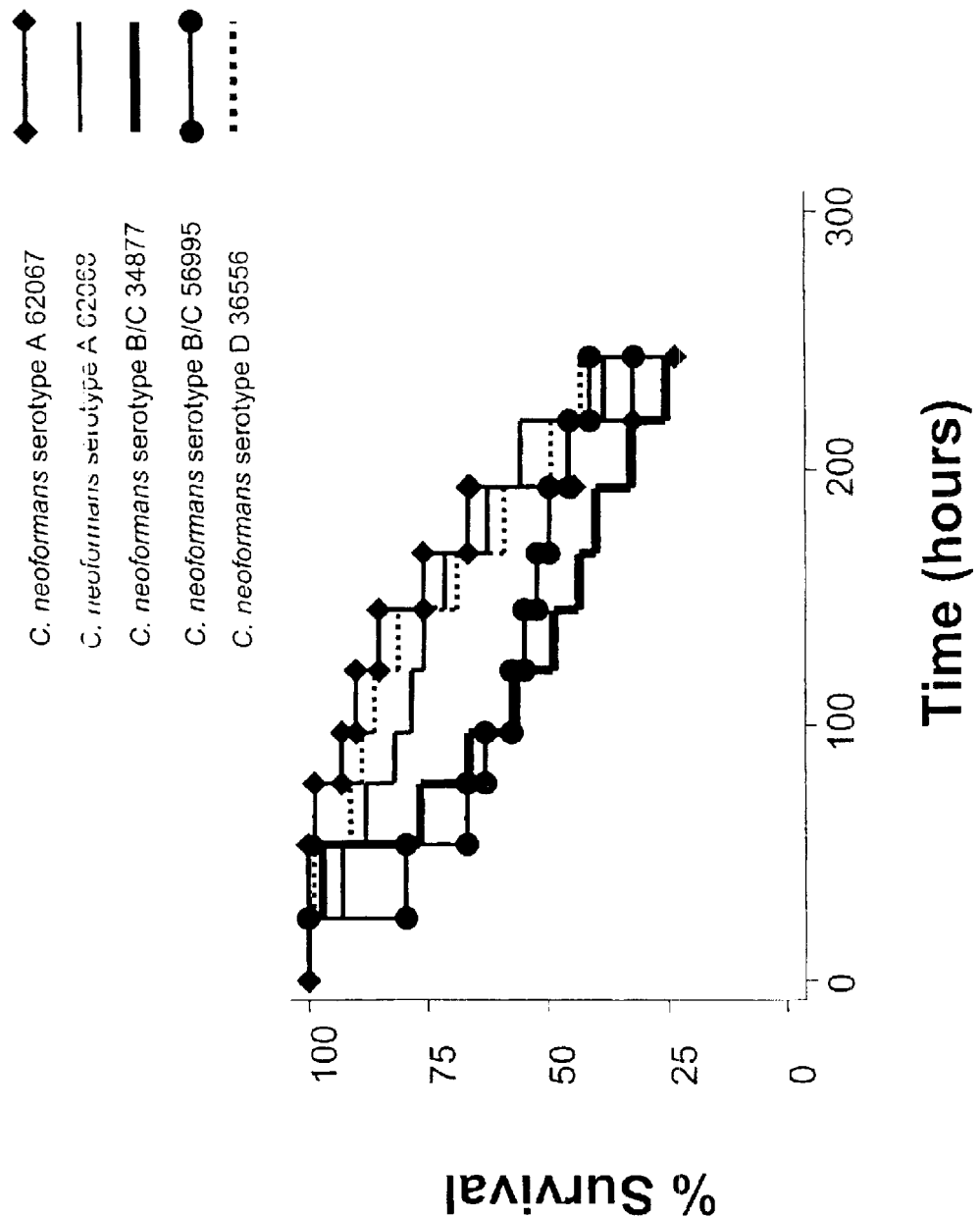
FIG. 5 is a graph showing *C. elegans* killing on lawns of *C. neoformans* serotype A (ATCC Nos. 62067 and 62068), serotype B/C (ATCC Nos. 34877 and 56995), and serotype D (ATCC No. 36556) (obtained from the American Type Culture Collection (ATCC), Manassas, Va.).

Clinical and environmental isolates of *C. neoformans* were observed to infect and kill *C. elegans*. In particular, *C. elegans* killing was seen in clinical isolates of: *C. neoformans* serotype A (ATCC Nos. 208821, 62067, and 62070), serotype B/C (ATCC Nos. 56691 and 56695), and serotype D (ATCC Nos. 36556 and 24067). Exemplary killing curves with ATCC Nos. 62067, 62068, 34877, 36556, and 56995 are shown in FIG. 5. Also, environmental isolates of *C. neoformans* (ATCC Nos. 14116, 34870, 32308, 32045, and 62068) were pathogenic to *C. elegans*. Significant *C. elegans* killing started at day two or three, and most *C. neoformans* strains demonstrated an $LT_{50}$ (time for half of the worms to die) of five to seven days. Two different serotype A isolates, ATCC No. 62067, which makes a small capsule, and ATCC No. 62068, which produces a moderate-size capsule, did not differ in *C. elegans* killing.

We also compared the life-span of wild-type *C. elegans* cultured on plates with lawns of control yeast versus the lifespan of nematodes cultured on plates with lawns of *E. coli* OP50. Evaluation of *C. elegans* life span on *E. coli* OP50, *C. kuetzingii*, and *C. laurentii* was performed at 25° C. using 3 to 4 day-old adult nematodes at developmental stage L4 which were cultured on medium containing 100 mg/ml 5-fluoro-2'-deoxyuridine (FdUrd; Sigma), and seeded with bacteria or yeast. Surviving *C. elegans* were counted each day and dead *C. elegans* were removed.

From these experiments, nematode life-span on *C. laurentii* (ATCC No. 18803) and *E. coli* OP50 ($LD_{50}$=14 days, $LD_{90}$=16 days, in both groups) did not differ. In particular, nematode life-span on *C. kuetzingii* lawns was longer than those cultured on *E. coli* OP50 or *C. laurentii* ($LD_{50}$=20 days, $LD_{90}$=22 days, P<0.000 compared to the group exposed to *E. coli* OP50).

Infection of *C. elegans* by cryptococci

To evaluate cryptococci infection, nematodes were exposed to yeast on BHI plates and then placed on a pad of 2% agarose in a 5-$\mu$l drop of 30 mM $NaN_3$ in M9 medium. The worms were then examined with an AXIOPLAN2™ microscope (Zeiss) with Nomarski optics.

Microscopic evaluation of nematodes exposed to *C. neoformans* H99 showed that yeast cells accumulated inside the nematode's intestine. In particular, yeast cells accumulated posterior to the nematode's grinder, and throughout the gastrointestinal tract. This accumulation was unlikely to be due to *C. neoformans* H99 proliferation within the gastrointestinal tract, since the nematode's gastrointestinal tract was filled six hours after transfer to lawns of *C. neoformans*. In contrast, the nonpathogenic yeast fungi, *C. laurentii* and *C. kuetzingii*, failed to infect *C. elegans*, and there was no dilation of the nematode intestinal tract (even on day seven of the experiment). These observations parallel our results in nematodes cultured in the presence of bacterial pathogens, where pathogen survival within the nematode gastrointestinal tract is often associated with nematode killing.

During mammalian cryptococcosis, *C. neoformans* fails to colonize mammalian cells. To determine whether *C. neoformans* colonizes *C. elegans*, we took advantage of the fact that *C. laurentii* did not kill *C. elegans*. For this experiment, nematodes were allowed to feed on a lawn of *C. neoformans* H99. The worms were subsequently transferred to lawns of *C. laurentii*. These transferred animals survived, even if they were exposed to *C. neoformans* H99 for up to forty-eight hours, indicating that *C. neoformans* did not colonize *C. elegans*.

Killing of *C. elegans* is not due Solely to Maticidial Effect

In previous studies, we found that *C. elegans*, when exposed to certain pathogens, produce eggs that hatch inside the parent. These internally hatching progeny devoured the parent, and expedited killing. This killing can be avoided by using *C. elegans* glp-4, a mutant nematode that is unable to produce eggs when grown at 25° C. We found that *C. neoformans* H99 also killed glp-4 mutants, although this killing occurred more slowly than the killing of wild-type nematodes.

MFα1::GFP Reporter Detected after *C. neoformans* Ingestion by *C. elegans*

*C. neoformans* reproduces either asexually, by budding, and/or sexually, by conjugation with cells of an opposite mating type (MAT-alpha and MAT a). MAT-alpha mating was previously associated with virulence in mammals and we found it to be associated with *C. elegans* killing as well (FIG. 6A). To examine MAT alpha expression in *C. neoformans* during nematode pathogenesis, we monitored the expression of a reporter gene (designated "MFα1::GFP"), consisting of the *C. neoformans* MAT alpha promoter fused to green fluorescent protein (GFP), during yeast infection of *C. elegans*. We exposed *C. elegans* to *C. neoformans* H99 transformed with a MFα1::GFP reporter and then evaluated *C. neoformans* GFP expression at 24-hour intervals. By analyzing GFP-micrographs taken using a Confocal Spectrophotometer Leica TCS NT microscope, we observed that there was no GFP expression twenty-four hours post-infection and minimal GFP expression forty-eight hours post-infection. By seventy-two hours, while no GFP expression was observed in uningested Cryptococcus, significant GFP expression was detected in Cryptococcus within the *C. elegans* intestine, and this GFP expression coincided with *C. elegans* killing (FIG. 6A). These results provide direct evidence demonstrating that the expression of a gene associated with virulence is temporally related to *C. elegans* killing.

Genes Associated with Pathogenesis in Mammals Caused Enhanced Killing of *C. elegans*

We next tested whether cryptococcal virulence factors identified in mammalian studies were also associated with virulence in *C. elegans*. These studies were conducted by exposing nematodes to different cryptococcal strains containing mutations in genes encoding virulence factors associated with signal transduction, capsule production, laccase production, alpha mating, adenine and uracil auxotropy, or the ferric/cupric reductase pathway, then assaying for the ability of the mutated pathogen to kill *C. elegans*.

We tested whether the *C. neoformans* signaling cascade which controls capsule formation and melanin production is associated with virulence in *C. elegans*. *C. neoformans* mutants with disruptions in this signaling cascade displayed attenuated virulence in murine models of cryptococcosis (Alspaugh et al. (2000) *Mol. Microbiol.* 36:352; D'Souza et al. (2001) *Mol. Cell Biol.* 21:3179). *C. neoformans* mutants with disruptions in PKA1, the gene encoding the major cyclic AMP (cAMP)-dependent protein kinase catalytic subunit or G alpha protein (GPA1) were also significantly less virulent than wild type *C. neoformans* H99 (in both cases $P<0.001$, FIG. 6B) when tested in *C. elegans*. Expression of wild-type GPA1 and PKA1 in gpa1 and pka1 mutants, respectively, restored virulence in *C. elegans*. *C. neoformans* pkr1, which contains a mutation in the gene encoding the protein kinase A regulatory subunit, was hypervirulent in mammals (D'Souza et al. (2001) *Mol. Cell Biol.* 21:3179), and in *C. elegans* ($P<0.01$, FIG. 6B).

The RAS1-specific signaling cascade regulates mating, filamentation, and growth at high temperature, and is associated with virulence in mammalian models of cryptococcosis (Alspaugh et al. (2000) *Mol. Microbiol.* 36:352). The RAS1 pathway is required for the maintenance of infection at high temperature. We tested a *C. neoformans* ras mutant, which had attenuated virulence in mammalian models, for virulence in *C. elegans*, and found that the ras mutant was significantly attenuated in virulence relative to wild-type *C. neoformans*. Expression of wild-type RAS in the ras mutant ($P<0.001$, FIG. 6B) restored virulence in *C. elegans*. These results indicated that RAS1 plays a role in *C. neoformans* virulence at lower temperatures (i.e., the *C. elegans* cultivation temperature of 25° C.).

We tested *C. neoformans* melanin mutants, CNLAC1 (laccase-positive) and cnlac1 (laccase-deficient) (Williamson et al. (1998) *J. Bacteriol.* 180:1570), for virulence in *C. elegans*. The laccase-positive and laccase-deficient strains showed no difference in virulence when the experiment was done using standard media (FIG. 6C). In contrast, when L-dopa (100 mg/L) was added to the culture media and plates, CNLAC1, which metabolized L-dopa to make melanin, was significantly more virulent than cnlac1, the laccase deficient strain (FIG. 6C).

*C. neoformans*' polysaccharide capsule distinguishes *C. neoformans* from other pathogenic fungi. The capsule protects *C. neoformans* during phagocytosis by immune effector cells, cytokine production, and antigen presentation to T cells (Doering. (2000) *Trends Microbiol.* 8:547; Feldmesser et al. (2000) *Infect. Immun.* 68:4225). *C. neoformans* mutants with deletions in the CAP59 gene, which is required for capsule formation, were attenuated in virulence when tested in a mouse model of cryptococcosis (Nelson et al. (2001) *Genetics* 157:935). We tested cap59 mutants for virulence in *C. elegans*. We found that cap59 was also attenuated in virulence in *C. elegans*. Specifically, while lawns of heat killed wild-type *C. neoformans* H99 killed *C. elegans*, nematodes survived for at least twelve days on lawns of the non-capsule forming mutants cap59 and 602. These results indicated that the cryptococcal capsule is a virulence factor in *C. elegans* as well as in mammals.

The phosphoribosylaminoimidazole gene (ADE2) of *C. neoformans* was shown to be essential for growth in mammalian cerebrospinal fluid. The *C. neoformans* H99 ade2 auxotroph (M001) was avirulent in a cryptococcal meningitis model in corticosteroid-treated rabbits (Perfect et al. (1993) *Infect. Immun.* 61:4446). We tested ade2 for virulence in *C. elegans* and found that it was significantly less virulent than *C. neoformans* H99 in *C. elegans*. At a time point when 90% of *C. elegans* exposed to *C. neoformans* H99 were dead, only 30% of *C. elegans* exposed to *C. neoformans* ade2 were dead. Virulence increased when the media was supplemented with 300 μM adenine. However, killing of nematodes exposed to *C. neoformans* H99 strain remained significantly higher than killing of nematodes exposed to ade2 ($P<0.0001$, data not shown).

A *C. neoformans* uracil auxotroph, ura5, was also less virulent in a murine model of cryptococcosis (Varma et al. (1992) *Infect. Immun.* 60:1101). We tested ura5 for virulence in *C. elegans*, and found that ura5 was significantly less virulent in *C. elegans* than *C. neoformans* H99 ($P<0.0001$, data not shown).

We have shown that cryptococcal virulence factors (e.g., factors associated with signal transduction, capsule production, melanin production, alpha mating, adenine and uracil auxotropy, and the ferric/cupric reductase pathway) are involved in both nematode and mammalian pathogenesis. These results indicate that a part of the fungal pathogen's virulence machinery required for disease development is common, or shared, in mammalian and worm hosts.

*C. elegans* Killing Predicts Virulence in Mammals

Two mutant strains of *C. neoformans* were tested for their ability to kill *C. elegans*. Both mutant strains have impaired ferric reductase activity. One mutant fungal strain, MYA-419, contained a mutation in frr2, which is associated with an increase in intracellular iron, which is sequestered in mitochondria (Nyhus et al. (1997) *Infect. Immun.* 65:434). The second mutant strain, MYA-418, contained a mutation in frr1, is a regulatory mutant associated with virulence in mammals. We tested frr1 and frr2 mutants for virulence in C. elegans and found that MYA-418 (frr1) and MYA-419 (frr2) were significantly less virulent than wild type C. neoformans (P<0.0001, FIG. 7A).

We then tested whether observations regarding virulence made in C. elegans could predict virulence in mammals. Mutant cryptococci were used to infect 4- to 6- week-old female ICR mice (Charles River Labs) using intraperitoneal injection according to standard procedures (Bava et al., (1989) *Mycopathologia* 108:81–8). Ten mice were inoculated in each experimental group. Preparation of inocula, including evaluation of the inoculum by hemocytometer, culture, killing of mice, and culture of internal organs was performed as previously described by Nelson et al. ((2001) i Genetics 157:935).

We found that frr2 had reduced virulence in a murine model of cryptococcal infection ($2.5 \times 10^7$ colony-forming units). None of the mice injected with the MYA-419 (frr2) strain died during the 8 days of our experiment (P<0.0001, FIG. 7B). In addition, preliminary studies, which did not reach statistical significance, indicated that MYA-420 (frr4) may be less virulent than wild type C. neoformans (P<0.20) in C. elegans and murine models of cryptococcosis. Taken together, these results indicated that C. elegans can be used to predict cryptococcal virulence in mammals.

Other Yeasts

Using the same methods described for Cryptococcus, we tested whether other fungal isolates including *Rhodotorula mucilaginosa* (ATCC No. 9449), *Saccharomyces cerevisiae* (ATCC Nos. 834, 2341, and 2601), *Saccharomyces pastorianus* (ATCC No. 2366), and *Candida parapsilosis* (ATCC No. 90018) killed C. elegans. We found that isolates of *Rhodotorula mucilaginosa, Saccharomyces cerevisiae,* and *Candida parapsilosis* killed C. elegans, while *Cryptococcus laurentii* did not (FIG. 8). *Saccharomyces pastorianus* also killed C. elegans (data not shown).

We next tested whether C. elegans could be used to identify virulence factors of Candida, a human fungal pathogen that causes a variety of infections in hosts with altered immunity. Only a small number of Candida virulence factors have been identified in conventional pathogenesis studies (Calderone et al., (2001) et al. *Trends Microbiol.* 9:327–35). We exposed C. elegans to test lawns of Candida, such as C. albicans, C. glabrata, and C. parapsilosis, then assayed viability daily. We found that while all three species of Candida killed C. elegans, this killing occurred most quickly on lawns of C. glabrata. C. elegans killing on C. glabrata occurred when the tests were done on a variety of laboratory media, including trypic soy, brain heart infusion, and YPD (FIG. 9A). We next tested whether a strain of Candida, ura3, a uracil auxotroph, which had been shown to have reduced virulence in mammals, also showed reduced virulence in C. elegans. We found that ura3 virulence was attenuated in C. elegans relative to the wild-type parent strain (FIG. 9B). This result indicated that C. elegans can be used to screen a library of Candida mutants to identify factors required for C. elegans and mammalian virulence.

Plant Cryptococcosis

To extend these results to a third host system, the pathogenicity of C. neoformans was tested in a plant system. To this end, we tested the ability of C. neoformans H99 to infect *Arabidopsis thaliana* Col-O ecotype. In these experiments, C. neoformans H99 was propagated on the surface of YPD agar at 28° C. for four days. Yeast cells were collected, suspended in 10 $\mu$M MgSO$_4$, and washed two times from the nutrient medium. Leaves of *A. thaliana* Col-O ecotype were then inoculated with $5 \times 10^5$ suspension of haploid yeast cells per ml 10 $\mu$M MgSO$_4$ by pipetting three 5 $\mu$l drops onto the upper epidermis of each detached Arabidopsis leaf. Inoculated leaves were incubated at 100% relative humidity at 30° C. for twenty-four hours, and then incubated at 22° C. for three to seven days. Macro and microscopic symptoms of C. neoformans var. neoformans in Arabidopsis Col-O leaves were evaluated three to seven days post-infection. Leaf punches with infection drop in the center were analyzed under Confocal Spectrophotometer Leica TCS NT (Germany) and Axioscope (Zeiss, Germany) microscopy using bright field and Nomarski optics.

The results of our experiments indicated that C. neoformans H99 caused disease symptoms in Arabidopsis. Characterization of Arabidopsis exposed to C. neoformans H99 revealed localized chlorosis around infection loci at three days post-infection, and soft-rot lesions appeared at seven days post-infection. These are typical symptoms for necrotrophic fungal pathogens in herbaceous plants. Microscopic examination showed numerous C. neoformans cells on the Arabidopsis leaf epidermis. Some of these fungal cells are budding. We also observed that some Arabidopsis cells were filled with round yeasts, surrounded with capsules, some of which where budding inside the plant cell. Neighboring epidermal cells were often free of fungi and had callose deposition.

These results indicated that the human pathogen *Cryptococcus neoformans* H99 can attach to the plant surface, infect a plant, and propagate within a plant cell by budding. *Cryptococcus neoformans* H99 may utilize plant nutrients both from symplast and leached from plant cells into an 'infection drop' on the epidermal surface. These results also indicated that herbaceous plants may be a source of human yeast infection causing fatal meningoencephalitis in immuno-compromized patients. Furthermore, these results indicated that C. neoformans var. neoformans is a multihost pathogen and plants, such as Arabidopsis, are useful for identifying and characterizing cryptococcal virulence factors.

The multi-host animal/plant pathogen system described herein has several practical ramifications. For example, these results indicate the molecular basis of pathogenesis is remarkably similar in plants and animals. Thus, as described below, the multi-host pathogen system can be used for the identification and study of new virulence factors. In particular, the entire *P. aeruginosa* genome can be scanned for pathogenicity-related genes by testing individually mutagenized *P. aeruginosa* in different host organisms, e.g., using the Arabidopsis or nematode assays described herein. A similar approach is applicable to identifying fungal virulence factors such as those found in Cryptococcus. Genes identified in this manner can then be tested in the mouse full-thickness skin burn model. This system also facilitates the elucidation of the molecular basis of host specificity of bacterial pathogens. Virulence factors identified using this model system provide targets for the development of a new generation of chemical therapies for both clinical and agricultural microbial diseases.

Screening Systems for Identifying Common Virulence Genes

Based on the results described above showing that a set of *P. aeruginosa* virulence factors are involved in pathogenicity in three diverse hosts and that these common virulence determinants define fundamental features of bacterial pathogenicity which are host independent, we have developed a method for identifying virulence determinants important for pathogenicity in plants and animals. The screen utilizes a multi-host animal/plant pathogen (e.g., *P. aeruginosa* UCBPP-PA14) and exploits the ability to readily screen thousands of randomly generated microbial mutants in virtually any host organism. Useful eukaryotic host organisms include, without limitation, nematodes (e.g., *Caenorhabditis elegans*), plants (e.g., a seed or leaf from Arabidopsis), yeast or other fungi, fish (e.g., zebrafish), flies (e.g., *Drosophila melanogaster*), mice, and the like. In general, a microbial pathogen is mutated according to standard methods known in the art and then subsequently evaluated for its ability to induce disease in the host organism. Mutagenized pathogens found to have diminished pathogenicity or which are rendered non-pathogenic are useful in the method of the invention. Such mutant pathogens are then used for identifying host-dependent or host-independent virulence factors responsible for pathogenicity according to methods known in the art.

The following is a working example of a virulence factor nematode screening system which utilizes the human clinical isolate *P. aeruginosa* UCBPP-PA14 found to be infectious in three different models: a mouse skin full-thickness burn model, a *C. elegans* nematode feeding model, and an *Arabidopsis thaliana* leaf infiltration model. The advantage of using a nematode as a host for studying a human or plant pathogen such as Pseudomonas is the relative simplicity of identifying non-pathogenic Pseudomonas mutants in the nematode. For example, a *C. elegans* screen consists of putting two L4 stage worms on a lawn of a *P. aeruginosa* mutant and looking for surviving worms after 5 days. A pathogen such as *P. aeruginosa* UCBPP-PA14 is mutated according to any standard procedure, e.g., standard in vivo or in vitro insertional mutagenesis methods (see, e.g., Kleckner et al. (1977) *J. Mol. Biol.* 116:125). Other methods are also available, e.g., chemical mutagenesis. By the fifth day, very few or no live worms can be found in the plate seeded with wild-type, pathogenic bacteria, whereas on a plate with *E. coli* or a non-pathogenic mutant, hundreds or thousands of live progeny of the initial two hermaphrodite worms are present. Thus, worms growing in the presence of mutated *P. aeruginosa* is an indication that a gene responsible for pathogenicity has been inactivated. The positions of an inactivating mutations are mapped, leading to the cloning and identification of the mutated virulence factor (e.g., by nucleotide sequencing).

To identify genes involved in pathogenicity, we generated mutants of *P. aeruginosa* UCBPP-PA14 using standard techniques of transposon mutagenesis (see, e.g. Manoil et al. (1985) *Proc. Natl. Acad. Sci.* 82:8129; Taylor et al. (1989) *J. Bacteriol.* 171:1870); over 8000 mutants were generated. The pathogenicity of 1900 of these mutants was then assessed using the *C. elegans* feeding assay described above. As shown in Table IV, we isolated 8 UCBPP-PA14 mutants that exhibited attenuated pathogenicity in *C. elegans*.

In addition, we also examined the pathogenicity of another collection of mutants generated by transposon mutagenesis in a lettuce leaf pathogenesis assay using standard methods (see, e.g., Cho et al. (1975) *Phytopathology* 65:425). Using this assay, we isolated 2900 UCBPP-PA14 mutants with attenuated pathogenicity on lettuce leaves. These mutants were subsequently tested in the Arabidopsis leaf pathogenesis assay according to the methods described herein. As shown in Table IV, we isolated 12 UCBPP-PA14 mutants that exhibited attenuated pathogenicity in Arabidopsis.

TABLE IV

|  | Arabidopsis thaliana | C. elegans |
|---|---|---|
| No. of mutants tested | 2900 | 1900 |
| No. of attenuated mutants | 12 | 8 |

One UCBPP-PA14 mutant identified in the Arabidopsis infiltration assay was then tested for pathogenicity in both the *C. elegans* feeding assay and the mouse full-thickness skin burn assay. We found that this UCBPP-PA14 mutant was less pathogenic in both systems when compared to the wild-type UCBPP-PA14 strain. Furthermore, we also tested two mutants identified in the Arabidopsis bioassay for pathogenicity in the mouse full-thickness burn assay. These mutants were also found to be less pathogenic in mice when compared to the wild-type UCBPP-PA14 strain. Together these results provide further evidence for the existence of common virulence factors for pathogenicity in plants and animals.

The results described above demonstrate that pathogenic interactions occur between *P. aeruginosa* UCBPP-PA14 and *C. elegans*. Strain UCBPP-PA14 kills *C. elegans*. UCBPP-PA14 is also infectious in an *Arabidopsis thaliana* leaf infiltration assay (FIGS. 1 and 2; Table I) and in a mouse full-thickness skin burn model (Tables II and III). Furthermore, we have demonstrated that null mutations in UCBPP-PA14 degP and gacA genes significantly decrease pathogenesis in all three models. Thus, we have provided the first evidence for the existence of common virulence factors for pathogenicity in plants and animals. Such virulence factors make possible the isolation of compounds that interfere with virulence factor function (e.g., through direct reduction of pathogenicity or enhancement of a host response), and also make possible the identification of these compounds in simple experimental systems (e.g., Caenorhabditis).

In addition, screening systems described above can also be used to identify virulence factors of virtually any pathogenic fungus (e.g., Aspergillus, Candida, including *Candida parapsilosis, Candida glabrata*, and *Candida albicans*, Cryptococcus, including *Cryptococcus neoformans*, Histoplasma, Plastomyces, Rhodotorula, including *Rhodotorula mucilaginosa*, Saccharomyces, including *Saccharomyces cerevisiae*, and *Saccharomyces pastorianus*), which are required for infection in mammals. In one working example, mutant isolates of *C. neoformans* with reduced virulence in *C. elegans* are identified using the above-described method of exposing the nematode to yeast lawns and comparing *C. elegans* killing on lawns of mutant *C. neoformans* relative to lawns of *C. neoformans* H99. This was accomplished by generating a library of mutant yeast having reduced virulence according to standard methods. In one working example, *C. neoformans* is mutagenized by restriction enzyme mediated integration (REMI) according to standard methods (Kuspa and Loomis (1994) *Genetics* 138: 665–674; Tang et al. (1992) *Mol. Microbiol.* 6: 1663–1671, 1992; Lu, *Proc. Natl. Acad. Sci., USA* 91: 12649–12653, 1994; Bolker (1995) *Mol. Gen. Genet.* 248: 547–552. Mutant isolates are cultured clonally on plates. *C. elegans* are then transferred to the mutant lawns, cultured, and assayed for viability at twenty-four hour intervals.

Mutant fungal strains having reduced virulence in the *C. elegans* model system are taken as candidates for the identification of fungal pathogen virulence factors. Fungal virulence factors are identified according to standard methods, for example, by inverse PCR using the inserted DNA and subsequent sequencing of the adjacent fungal DNA. *C. neoformans* with reduced virulence in *C. elegans* is then tested for reduced virulence in plants and higher animals, and common virulence factors are identified. The use of *C. elegans* as a screening system permits the relatively rapid and inexpensive identification of important fungal virulence factors.

*C. elegans* is also useful for the identification of candidate compounds that reduce the lethality of a fungal pathogen virulence factor. In one working example, *C. elegans* are cultured on lawns of a fungal pathogen (e.g. Cryptococcus, Aspergillus, Plastomyces, Histoplasma, Saccharomyces, and Candida) in the presence of a test compound. *C. elegans* killing by the fungal pathogen is then compared between plates cultured in the presence or absence of the test compound. A test compound that reduces *C. elegans* killing is taken as useful in the invention.

Screening Systems for Identifying Common Virulence Genes Using a Nematode "Fast Killing" Assay Evidence described above shows that *P. aeruginosa* strain UCBPP-PA14 is capable of killing *C. elegans* over a period of 2.5–5 days when the PA14 lawn is grown on NGM agar. The rate of killing observed under these conditions is defined as "slow killing." Briefly, under the slow killing conditions, 5 μl of an overnight liquid culture of PA14 is spread on the center of an NGM (or M9) agar plate and grown for 37° C. for 24 hours. The plates are then allowed to cool to room temperature for several hours. Worms at the fourth larval stage (L4) are added to the agar but not in contact with the bacterial lawn. The worms typically move toward the bacterial lawn and commence feeding. In contrast, when PA14 worms were grown on peptone-glucose-sorbitol (PGS), a richer medium of higher osmolarity, a different result was obtained. When L4 worms were placed on PGS plates, the worms became sluggish, then paralyzed, and then died within 4–24 hours (FIG. 10). Some worms died even before coming into direct contact with the bacterial lawn. This more rapid killing on PGS agar is termed "fast killing."

To determine whether the difference in the kinetics between fast and slow killing was due to differences in the underlying mechanisms, or whether fast killing was simply an acceleration of the process seen in slow killing, the effects of PA14 bacterial mutants were tested in these conditions. Selected killing curves are shown in FIGS. 11A–11H, and the data are summarized in Table V.

TABLE V

Ability to Kill *C. elegans* under these conditions

| Strain | Fast | Slow | Gene Identity |
|---|---|---|---|
| PA 14 | + | + | |
| Pathogenic in both Fast and Slow Killings | | | |
| PA14plcS | + | + | PlcS |
| PA14algDΔ4 | + | + | AlgD |
| 16G12 | + | + | no matches |
| 25A12 | + | + | no matches |
| 33A9 | + | + | no matches |
| 33C7 | + | + | no matches |
| Delayed only in Slow Killing | | | |
| PA14toxA | + | ± | ToxA |
| 35A9 | + | ± | no matches |
| 44B1 | + | ± | not sequenced |
| 25F1 | + | ± | no matches |
| 41A5 | + | ± | no matches |

TABLE V-continued

Ability to Kill *C. elegans* under these conditions

| Strain | Fast | Slow | Gene Identity |
|---|---|---|---|
| 41C1 | + | ± | not sequenced |
| 34H4 | + | ± | no matches |
| Impaired only in Slow Killing | | | |
| PA14gacA | + | − | GacA |
| 50E12 | + | − | dst* of invA |
| rpn7-lasR | + | − | LasR |
| Impaired only in Fast Killing | | | |
| 49H2 | − | + | not sequenced |
| Impaired in Fast Killing and Delayed in Slow Killing | | | |
| PA14degP | − | ± | DegP |
| pho15 | − | ± | DsbA |
| 34B12 | − | ± | dst* of phnB |
| Impaired in Fast and Slow Killing | | | |
| pho23 | − | − | no matches |

As shown in FIGS. 11A–11H, mutations in the PA14 gacA or the lasR genes, both of which are transcriptional regulators of extracellular virulence factors (Gambello et al. (1993) *Infect. Immun.* 61;1180–1184; Rahme et al. (1995), *Science* 268:1899–1902), completely abolished slow killing but had no effect on fast killing (FIGS. 11A–11D). Conversely, a mutation in the PA14 degP gene, which encodes a periplasmic protease, and a TnphoA insertion in an uncharacterized gene (TnphoA mutant 49H2), dramatically reduced fast killing but only delayed slow killing (FIGS. 11E–11H). The data shown in FIGS. 11A–11H and Table V are most consistent with the hypothesis that PA14 employs different mechanisms in killing *C. elegans* depending on the medium in which the bacteria are grown.

Pathogenicity of Other Species and Strains of Pseudomonas

It has been shown that, similar to *E. coli, P. fluorescens* (Strains 55, 2–79 and WCS365) and *P. syringae* pv. maculicola strain ES4326 do not kill *C. elegans* under the slow-killing conditions described above; bacterial lawns are completely consumed and the nematodes develop and reproduce normally. Whereas *E. coli, P. syringae* pv. *maculicola* E4326, and *P. fluorescens* 55 were also nonpathogenic in the fast killing conditions, *P.fluorescens* 2–79 (FIG. 12A) and *P. fluorescens* WCS365 (data not shown) were as virulent as *P. aeruginosa* PA14 under the fast killing conditions. Interestingly, both *P. fluorescens* 2–79 and WCS365 are efficient root-colonizers and are being studied intensely for their ability to suppress fungal infections (Mazzola et al. (1992) *Appl. Environ. Microbiol.* 58:2616–2624).

Because different strains of *P. aeruginosa* produce different quantities of extracellular virulence factors (Hamood et al. (1992) *Infect. Immun.* 60:510–517), the virulence of different strains of *P. aeruginosa* were also tested under the fast killing conditions. As shown in FIG. 12B, none of the other *P. aeruginosa* strains tested was as virulent as PA14 under the fast killing conditions. Preston et al, (*Infect. Immun.* 63:3497–3501, 1995) showed that variants of the same parental PAO1 strain maintained in different laboratories showed significant differences in virulence in mouse corneal infections, and thus, we also tested different laboratory collections of the PAO1 strain. However, all of the PAO1 variants tested were less virulent than PA14 and not significantly different among themselves (FIG. 12C). Since the other *P. aeruginosa* strains were not as virulent as PA14, we proceeded to use PA14 for all additional experiments described below.

Factors Affecting *P. aeruginosa*-Mediated Fast Killing of *C. elegans*

Developmental stage of worms. We have shown that under the slow-killing condition, adult worms died faster than L4 worms. We therefore tested the effect of worm developmental stage on their sensitivity to fast killing. As shown in FIG. 13A, L4 worms were more susceptible to fast killing than one-day-old hermaphrodite adults. For example, at 12 hours after exposure to *P. aeruginosa* PA14, over 90% of L4 worms were dead, whereas only less than 10% of one-day-old adult worms died under equivalent conditions (FIG. 13A).

Bacterial factors. A bacterium has an incredible ability to modulate gene expression in response to changes in environmental stimuli. This type of regulation may be essential for adaptation to changes in a physical environment and/or the the expression of virulence factors. Some of the known factors that modulate gene expression in bacteria are osmolarity, temperature, iron and phosphate concentrations, and carbon source. Slow killing media (NGM or M9) are high in phosphate, whereas the fast killing medium is low in phosphate. We tested the effects of altering osmolarity, growth temperature, iron concentration, and carbon source of the M9 agar on the kinetics of slow killing. Except for iron concentration of the growth media, where an increase in iron resulted in a slight delay in killing, none of the other parameters significantly affected slow killing. This was not surprising since slow killing is a consequence of bacterial establishment and proliferation within the worm gut and the in vivo conditions are more likely to affect *P. aeruginosa* pathogenicity than the in vitro growth conditions.

Osmolarity. The rate of killing on Peptone-Glucose medium (PS) was considerably higher on drier plates. To test whether this increase in killing was a function of increased osmolarity, sorbitol was used to increase osmolarity without increasing electrolyte concentrations. Peptone-Glucose medium was used in the absence (PG) or the presence of 0.1 M and 0.15 M sorbitol (PGS). Growth rates of PA14 were the same in PG and PGS media. However, as shown in FIG. 13B, significantly higher mortality of *C. elegans* and a faster rate of killing was observed as the osmolarity of the medium increased, suggesting an increase in the production of osmolarity-regulated virulence factors. Consistent with the hypothesis that osmolarity affects the secretion of bacterial virulence factors, it has been shown for *Aeromonas hydrophila*, another opportunistic human pathogen, that cells grown at high osmolarity show increased hemolytic, cytotoxic, and caseinolytic activities, and are more virulent in fish and mouse pathogenicity models, compared to cells grown in medium with lower osmolarity (Aguilar et al. (1997) *Infect. Immun.* 65:1245–1250). An alternative hypothesis is that enhanced fast killing in high osmolarity medium was due to a decrease in tolerance of the nematode. Indeed, we observed that, when L4 *C. elegans* were placed on high osmolarity agar medium (PG with 0.15 M sorbitol) containing *E. coli* or nonpathogenic strains of PA14, the nematodes initially became paralyzed, but then recovered.

Iron. The availability of iron is an important stimulus used by many pathogenic bacteria to induce the expression of virulence factors. Iron-limiting conditions promote increased synthesis of toxin A, alkaline protease, and elastase (Bjorn et al. (1978) *Infect. Immun.* 19:785–791; Bjorn et al. (1979) *J. Bacteriol.* 138:193–200). Many of these exoproducts contribute to the virulence of *P. aeruginosa* pathogenesis. Consistent with this result, *P. aeruginosa* strain PAO1 produces significantly more corneal damage when grown in low-iron medium in comparison with damage produced when grown in high-iron medium (Woods et al. (1982) *Infect. Immun.* 35:461–464), although the virulence factor(s) involved have not been reported. To ascertain if any of the virulence factors involved in *C. elegans* fast killing were iron regulated, PA14 killing efficacy was tested under iron-limiting and iron-replete conditions. As shown in FIG. 13C, the addition of an iron chelator (400 $\mu$M of EDDA) did not significantly affect fast killing whereas the addition of 100 $\mu$M of $FeCl_3$, significantly reduced killing. Several conclusions can be drawn from these observations. First, because PGS medium is probably iron-limiting, the addition of an iron chelator did not have a significant impact on the concentration of available iron. Second, the reduction in killing in the iron-replete condition suggested that either the production of a subset of factors involved in *C. elegans* killing are iron repressed (transcriptional regulation), or the activity of one or more factors are reduced (post-translational regulation), under high iron concentration.

Temperature. The effect of growth temperature on fast killing on PGS medium was tested by growing lawns of wild-type PA14 at 20, 25, 30, and 37° C. for 36 hours. After seeding with one-day old adult worms, all plates were incubated at 25° C. As shown in FIG. 13D, no significant difference in worm mortality was seen for bacteria grown at 20, 25, or 30° C.; however, PA14 grown at these three temperatures were significantly more virulent than PA14 grown at 37° C. The difference in temperature on the rate of mortality was not obvious when the more susceptible L4 stage was used (data not shown). A similar increase in virulence has also been reported for *A. hydrophila*. In comparison to cells cultivated at 37° C., cells grown at 20° C. were more virulent in fish and mice and exhibited increased extracellular activities (Merino et al. (1992) *Infect. Immun.* 60:4343–4349). In *P. aeruginosa* strain PA103, at least one virulence factor is known to be regulated by temperature. In a study using a toxA-lacZ promoter fusion integrated into the PA103 chromosome at the toxA locus, maximal -galactosidase production occurred at 25° C. and decreased with increasing temperature (Vasil et al. (1989) *Mol. Microbiol.* 3: 371–381). In general, however, it remains to be ascertained whether particular *P. aeruginosa* virulence factors are produced at elevated levels at 20–30° C. relative to their production at 37° C. In the context of the *C. elegans* model, elucidation of the mechanism underlying the decrease in virulence when cells are grown at 37° C. may provide a clue to the puzzling fact that, despite the possession of many virulence factors, *P. aeruginosa* remains an opportunist in humans and other mammals where the optimum body temperature is 37° C.

Carbon Source. The expression of virulence determinants by many pathogenic bacteria is governed by the carbon source used for growth. In testing the effects of carbon source on PA14 virulence, the PGS media was modified by replacing glucose at 1% of total final volume (PGS) with glycerol at the same concentration (PYS). As shown in FIG. 13E, PA14 fast killing of *C. elegans* was more efficacious when PA14 was grown in Peptone-sorbitol with glucose (PGS) instead of glycerol (PYS) as a carbon source. The difference in killing efficiency was not attributable to differences in bacterial growth rate on the different carbon sources since PA14 grew just as well under both media conditions (data not shown).

Although wild-type PA14 killed more effectively on glucose than glycerol medium, a PA14 mutant containing a TnphoA insertion in the lasR gene (strain rpn7-lasR) killed more rapidly than its parent PA14 on PYS, in which glycerol, rather than glucose, was used as the carbon source (FIG. 13F). The kinetics of killing between strain rpn-lasR and wild-type PA14 were indistinguishable on PGS. Interestingly, strain rpn7-lasR grown on PYS show an increased blue-green pigmentation of the agar. We grew both rpn7-lasR and PA14 in PYS liquid medium and showed a 3–5 fold increase in the production of pyocyanin in rpn7-lasR relative to wild-type PA14. Although we did not rule out the overproduction of other pigments or compounds, this result established a correlation between increased rate of killing and increased pyocyanin production.

Bacterial Factors Involved in PA14-mediated Fast Killing

The rapid killing and the observation that some worms died even before being in direct contact with bacteria prompted us to test if diffusible toxins played an important role in fast killing. *P. aeruginosa* was grown on PGS agar medium under similar conditions as in previous tests except that, after growth, the bacterial lawn was scraped off the agar surface and the remaining bacteria killed by exposing them to chloroform vapor. Prior to the addition of worms, residual chloroform was removed by venting the plates for one hour in a fume hood. *E. coli* strain DII5α was used to control for treatment effects on the worms. As shown in FIG. 14A, the killing efficacy was the same with or without live PA14 bacteria. Chloroform treatment had no deleterious effects on the nematodes since none of the worms died on chloroform treated DH5α plates. Similar results were obtained by killing PA14 with UV irradiation (data not shown). These results showed that, after a period of bacterial growth on PGS agar, one or more compounds that had diffused into the agar were sufficient for fast killing. The same chloroform experiment was done on bacteria grown on NG agar, the slow killing media, and none of the worms died. This suggested that diffusible toxins, if present at all in the NGM agar, were in such low concentrations that they had no impact on worm killing under slow killing conditions.

To determine if the compounds responsible for fast killing could be inactivated by high temperature, we heated plates containing a PA14 bacterial lawn at 65° C. for 30 minutes or 60 minutes. As shown in FIG. 14B, there was no significant difference in killing between heated plates and non-heated controls, suggesting that the main factors responsible for fast killing were relatively heat stable.

To further support the hypothesis that diffusible toxins are involved in fast killing, we tested the susceptibility of a *C. elegans* P-glycoprotein mutant (strain NL130 [pgp-1(pk17);pgp-3(pk18)]) to PA14-mediated fast killing. P-glycoproteins belong to an evolutionarily conserved family of ATP binding membrane transporters and are thought to protect cells from exogenous toxins by actively extruding them from cells (Higgins (1995) *Cell* 82:693–696). Strain NL130 has the pgp-1 and pgp-3 genes deleted, and has been shown to be more sensitive to the cytotoxic agent colchicine and the antimalarial/antiprotozoal agent chloroquine (Broeks et al. (1995) *EMBO J*. 14:1858–1866). NL130 is also more sensitive to the fungal toxin fumonisin $B_1$. Susceptibility of L4 stage worms of strain NL130 to PA14 grown on PGS agar was compared to the susceptibility of the parent wild-type strain N2. In parallel, we also tested both NL130 and N2 under the slow killing conditions. As shown in FIG. 15A, consistent with the hypothesis that fast killing is mediated by a diffusible toxin, 70% of N2 worms were still alive after 4 hours of exposure to PA14 under the fast killing condition, while less than 5% of NL130 worms survivied. In contrast, such a dramatic increase in susceptibility was not observed for NL130 under the slow-killing conditions where the mechanism of killing appeared to involve bacterial colonization and proliferation in the worm gut (FIG. 15B).

Alginate is not Important for Fast Killing

As described above, a PA14 degP mutant was significantly impaired in its ability to cause fast killing. In addition to the attenuated pathogenicity phenotype, the PA14 degP mutant was significantly more mucoid than wild-type on PGS agar due to the overproduction of the exopolysaccharide alginate. Consistent with the mucoidy phenotype, DNA sequence analysis of the UCBPP-PA14 degP gene, as well as independent DNA sequence analysis in a different *P. aeruginosa* strain by Boucher et al (*J. Bacteriol*. 178:511–523, 1996), showed that degP lies tightly clustered with four other genes that have been shown to be involved in the regulation of alginate. To address the question of whether the attenuated pathogenicity phenotype of the PA14degP mutant was due simply to the overproduction of alginate, a double PA14degP algD mutant was constructed and tested under fast and slow *C. elegans* killing conditions. The algD gene encodes the enzyme, GDP mannose dehydrogenase that catalyzes an early step in alginate biosynthesis (Deretic et al. (1987) *Nucleic Acids Res*. 15:4567–4581; Lightfoot and J. L. (1993) *Mol Microbiol*. 8:771–782). Strain PA14algD 4 was constructed by marker-exchanging an algD in-frame deletion with the wild-type algD gene in PA14. PA14algD 4 was not mucoid on Pseudomonas Isolation Agar (PIA) confirming the absence of alginate (Yorgey and Ausubel, unpublished). As shown in FIGS. 16A and 16B, PA14algD 4 killed *C. elegans* at the same rate as wild-type PA14 in both the fast and slow killing assays, indicating that alginate was not required for either fast or slow killing. Moreover, the PA14degP algDD4 double mutant exhibited the same attenuated pathogenicity phenotype as the degP mutant in both fast and slow killing, suggesting that degP is likely to be involved in the regulation of other virulence-related factors in addition to alginate.

In addition to these data, two additional PA14 mutants, a toxA mutant and a plcS mutant, were also indistinguishable from wild-type in the fast killing assay (Table V). Therefore, hemolytic phospholipase C (encoded by plcS) and exotoxin A (encoded by toxA) are also not essential for fast killing.

Phenazines Contribute to the Fast Killing Process

As described in detail in Materials and Methods below, we conducted a screen to isolate PA14::TnphoA transposon insertion mutants that were defective in fast killing. This led to the identification of five mutants out of a total of 2400 screened (a frequency of 0.21%) that exhibited an attenuated fast killing phenotype compared to the wild-type PA14 parental control. Analysis of these and several other PA14 mutants suggested that fast killing by PA14 was multifactorial, and that one of these factors belongs to a group of pigments collectively known as phenazines.

DNA sequence obtained from an 800 bp IPCR product 3' to the TnphoA insertion of one of the mutants, 3E8, has been cloned and sequenced. Preliminary analysis of the DNA sequence reveals that mutant 3E8 defines a TnphoA insertion in a phzB-like gene; 177 bp of sequence immediately downstream of the TnphoA insertion showed 69% identity at the nucleotide level to the phzB gene, one of the genes involved in the biosynthesis of phenazines in the closely related *P. fluorescens* strain 2–79 (NRRL B-15132). *P. aeruginosa* is also a phenazine producer, and the best characterized phenazine produced by *P. aeruginosa*, pyocyanin, has been implicated to play an important role in animal pathogenesis (Sorensen and Joseph (1993) Phenazine pigments in *Pseudomonas aeruginosa* infection. In *Pseudomonas aeruginosa* as an opportunistic pathogen, Campa, Bendenelli and Friedman, eds. (New York: Plenum Press), pp. 43–57). Importantly, PA14 mutant 3E8, which is reduced in fast killing, is also defective in pyocyanin production, synthesizing only 50% of the wild-type levels (Table VI).

TABLE VI

| Strain | Gene Mutated | Pyocyanin[a] (proportion of PA14) | % Worms killed[b] |
|---|---|---|---|
| PA14 wild-type | | 1.00 | 87 |
| PA14phnAphnB | phnAphnB | 0.50 | 50 |
| 3E8 | phzB-like | 0.50 | 10 |
| 34B12 | unknown | 0.03 | 50 |
| 49H2 | unknown | 0.11 | 0 |

[a]Pyocyanin quantitation is based on the measurement of absorbance at 520 nm ($OD_{520}$) in acidic solutions, modified from the method described by Essar et al., (1990) J Bacteriol 172:884–900. Values given are proportion of $OD_{520}$ readings relative to the wild-type PA14 after correcting for the number of cells per ml culture; mean of three measurements.
[b]The percentage of worms killed are mean from three replicates. Fast killing conditions are described in detail in methods.

Further support for the involvement of phenazines in the fast killing process came from analysis of two additional PA14 TnphoA mutants, 34B12 and 49H2. PA14 TnphoA mutant 34B12, which produced only 3% of the wild type levels of pyocyanin, was isolated during a screen for PA14 mutants attenuated in plant pathogenesis and was significantly impaired in fast killing (Table V). Mutant 34B12 formed a characteristic unpigmented colony on PGS media. TnphoA mutant 49H2, which produced 11% of wild type levels of pyocyanin, was identified by virtue of the fact that it also formed unpigmented colonies and showed attenuated symptoms on lettuce. Importantly, 49H2 was also impaired in fast killing (Table V): the mean percentages of dead worms at 12 hours post-exposure for 3E8, 34B12, 49H2, and wild-type PA14 were 10%, 5%, 0% and 87%, respectively (Table VI).

To further support the conclusion that pyocyanin (and other phenazines) played an important role in fast killing, a strain, PA14 phnAphnB, was constructed which had a gentamicin cassette inserted in the overlapping region of the cotranscribed phnA and phnB genes. The phnA and phnB genes encode the α and β subunits of an anthranilate synthase, which is required for pyocyanin synthesis (Essar et al. (1990) J. Bacteriol. 172:884–900). PA14phnAphnB produced intermediate levels of pyocyanin and also displayed an intermediate fast killing phenotype (Table VI).

Finally, it is known that phosphate deficiency triggers pyocyanin synthesis by P. aeruginosa and that high concentrations of phosphate inhibit pyocyanin production (Ingledew and Campbell (1969) Can. J. Microbiol. 15:595–598). We therefore tested PA14 fast-killing in PY agar with or without the addition of 20 mM phosphate (Pi). There was no difference in growth rate of PA14 in the two media. Consistent with previous reports, less pyocyanin was produced in the phosphate-replete medium, which corresponded to an attenuation of fast killing; at 16 HPE, the mean mortality was 62% for PA14 grown on Pi-deplete media, compared to 24% for Pi-replete media (FIGS. 17A and 17B).

Host Response to Fast Killing: Resistance to Fast Killing Correlates with Resistance to Oxidative Stress We have taken advantage of previously known C. elegans mutants that are resistant or more susceptible to oxidative stress to provide additional evidence that phenazines are important toxins in PA14-mediated fast killing. Some phenazines such as pyocyanin and phenazine-1-carboxylic acid are redox active compounds. For example, under aerobic conditions, pyocyanin spontaneously undergoes one electron reduction and reoxidation with coincident univalent reduction of $O_2$ to $O_2^-$(superoxide anions) (Hassan and Fridovich (1980) J. Bacteriol. 141:1556–163; Hassett et al. (1992) Infect. Immun. 60:328–336). Accordingly, in the presence of the appropriate reducing source, pyocyanin can generate a continuous flux of cytotoxic $O_2^-$ and $H_2O_2$ in host tissues. In the presence of a siderophore-iron complex, ferripyochelin, these reactive oxygen species (ROS) are further converted into the highly toxic hydroxyl radical (Coffman et al. (1990) J. Clin. Invest. 86:1030–1037; Britigan et al. (1992) J. Clin. Invest. 90:2187–2196). It has been suggested by several studies (Hassan and Fridovich (1980) J. Bacteriol. 141:1556–163; Hassett et al. (1992) Infect. Immun. 60:328–336), but not all (see Baron et al. (1989) Curr. Microbiol. 18:223), that pyocyanin exerts its cytotoxicity via its ability to induce the formation of ROS in target cells, akin to the cytotoxic effect of another superoxide-generator, paraquat (methyl viologen).

The age-1 (hx546) mutant of C. elegans was first identified because of its long-lived phenotype (Johnson, 1990, Science 249:908–912), and subsequently shown to be resistant to $H_2O_2$ due to an increased production of catalase and superoxide dismutase (Larsen (1993) Proc. Natl Acad. Sci. USA 90:8905–8909; Vanfleteren (1993) Biochemical Journal 292:605–608). Mutants that are highly susceptible to methyl viologen have also been identified, these include mev-1 and rad-8 (Ishii et al. (1990) Mutation Res. 237:165–171; Ishii et al. (1993) Mechanisms of Aging and Development 68:1–10). We reasoned that if P. aeruginosa fast killing was mediated via pyocyanin or other redox active phenazine(s), an age-1 mutant should be resistant by virtue of its increased resistance to oxidative stress. As shown in FIG. 18A, age-1 (hx546) was significantly more resistant to killing by PA14 than its parental N2 strain. Conversely, the methyl viologen-sensitive mutants mev-1 (kn-1) and rad-8(mn63) were highly susceptible to PA14 killing (FIG. 18B). These results established that nematode susceptibility to killing by P. aeruginosa was strongly correlated with the nematode's resistance to ROS-generating compounds.

Summary of Fast Killing Assay Results

P. aeruginosa has an impressive host range and within a single host, it can cause a wide spectrum of disease depending on the tissues it infects. In humans, P. aeruginosa can infect burns or surgical wounds, the urinary tract, the gastrointestinal tract, the respiratory tract, eyes, ears, and meninges (Baltch and Smith (1994) Pseudomonas aeruginosa: infections and treatment. (New York: Marcel Dekker, Inc.). Many different virulence determinants are required for the manifestation of disease in any particular tissue, but the set of factors may differ from one tissue type to the other. For example, the hemolytic phospholipase C is an important virulence factor in causing mortality in burned mice (Rahme et al. (1995) Science 268:1899–1902), but is not essential for corneal infection in mice (Preston et al. (1995) Infect. Immun. 63:3497–3501). Analysis of different bacterial mutants suggests that killing of C. elegans by P. aeruginosa is also multifactorial. The expression of factors needed for fast killing appears to be regulated by iron, carbon source, temperature and osmolarity.

In the case of fast killing, the data described above indicate that at least some of the virulence determinants are heat-stable diffusible toxins. However, by testing isogenic toxA, plcS, and algD mutants of PA14, two known toxins, the hemolytic phopholipase C and exotoxin A, as well as the exopolysaccharide alginate were shown not to be essential for killing worms under the fast killing conditions. Furthermore, from the demonstration that a strain carrying a mutation in lasR, an important transcriptional regulator of extracellular virulence expression, was still fully virulent under the fast killing conditions, it was inferred that alkaline protease (Gambello et al. (1993) *Infect. Immun.* 61:1180–4), staphylolytic protease (Toder et al. (1991) *Mol. Microbiol.* 5:2003–10) and elastase (Gambello and Iglewski (1991) *J. Bacteriol.* 173:3000–9), which are positively regulated by lasR, were also not essential for fast killing. In addition, the virulence factors were shown not to be inactivated by heating at 65° C. for up to 60 minutes, by chloroform, or by UV irradiation, suggesting the involvement of small non-proteinaceous molecules.

Evidence that Phenazines are Involved in Fast Killing

The results described above indicate that one of the toxins involved in fast killing is a phenazine. These results are as follows.

PA14 mutants affected in pyocyanin production. Analysis of one of the mutants attenuated in fast killing, strain 3E8, showed a TnphoA insertion in the middle of a phzB-like gene. The phzB gene is thought to encode an enzyme involved in phenazine biosynthesis in *P. fluorescens* strain 2–79. Consistent with this, we showed that a TnphoA insertion in the phzB-like gene in strain 3E8 resulted in a 50% decrease in the production of pyocyanin, the best characterized phenazine in *P. aeruginosa*. Similarly, a TnphoA insertion in an unlinked gene in strain 34B12, resulted in both an attenuation of fast killing as well as a dramatic decrease in pyocyanin production. Correlation between pyocyanin deficiency and attenuation of fast killing was also shown for strain 49H2; however, the possibility that the mutation in 49H2 could be allelic to those in either 34B12 or 3E8 has not been ruled out.

Phosphate affects both pyocyanin production and fast killing. In addition to demonstrating that high concentrations of phosphate in the growth medium inhibited pyocyanin production, fast killing was also shown to be reduced in phosphate-replete medium relative to phosphate-limiting medium.

Thermostability of the toxin. The fact that the diffusible compound required for fast killing was heat-stable and was not inactivated by chloroform or UV, was consistent with the conclusion that the toxin is or has as one component a phenazine. Phenazines are thermoresistant (Dakhama et al. (1993) *J. Appl. Phycology* 5:297–306).

*C. elegans* mutants. Pyocyanin is thought to cause toxicity by inducing the production of superoxides (Hassan and Fridovich (1980) *J. Bacteriol.* 141:1556–163; Hassett et al. (1992) *Infect. Immun.* 60:328–336). As described above the worm mutant age-1 (hx546), which is more resistant to the superoxide generator paraquat, was also more resistant to fast killing by PA14. Conversely, mutations in the unlinked *C. elegans* genes mev-1(kn-1) or rad-8(mn163) led to enhanced sensitivity to paraquat (Ishii et al., 1990, *Mutation Res.* 237:165–171; Ishii et al. (1993) *Mechanisms of Aging and Development* 68:1–10) and to enhanced PA14 fast killing.

The Role of Phenazines other than Pyocyanin in Fast Killing

Taken together, the results summarized above provide compelling evidence that at least one of the phenazines, pyocyanin, plays a significant role in fast killing. However, pyocyanin is the terminal product of phenazine biosynthesis in *P. aeruginosa* (Byng et al. (1979) *J. Bacteriol.* 138:846–852). In addition to pyocyanin, other phenazines produced by *P. aeruginosa* are oxychlororaphin(e), phenazine-1-carboxylic acid, chlororaphin(e), 1-hydroxyphenazine, and pyorubin (or aeruginosin A and B) (Turner and Messenger (1986) *Adv. Microbial Physiol.* 27:211–273). A number of strains of *P. aeruginosa* were reported to produce more than one phenazine (Byng et al. (1979) *J. Bacteriol.* 138:846–852), and the relative amounts produced were affected by growth conditions (Chang and Blackwood (1969) *Can. J. Bacteriol.* 15:439–444). Since neither the identity nor the quantity of other phenazines produced by PA14 in any of the above experiments was determined, participation by other phenazines, either independently or in concert with pyocyanin, in worm killing is possible. In addition, all measurements of pyocyanin were done in KA medium but the medium used for killing worms was PGS. Since the quantities of pyocyanin and other phenazines produced are affected by a variety of factors, variations in media may have contributed to the results.

Other phenazines may also be important for killing *C. elegans*. First, as discussed above, *P. aeruginosa* produces other phenazines in addition to pyocyanin. It was shown above that *P. aeruginosa* strain PAO1 was significantly less virulent than PA14 in the fast killing condition even though it produced similar amounts of pyocyanin and pyorubin as PA14. Since *P. aeruginosa* is known to produce several other phenazines, such as phenazine-1-carboxylic acid and 1-hydroxyphenazine, the attenuated virulence of PAO1 could be due to the absence, or the reduced amount, of other phenazines. In addition, *P. fluorescens* strain 2–79 and WCS365 were shown kill *C. elegans*, but these strains did not produce pyocyanin. These strains are effective biocontrol agents against Fusarium wilt and take-all diseases (caused by *F. oxysporum* F. sp. lini and *Gaeumannomyces graminis var. tritici*, respectively). The effectiveness of *P. fluorescens* strain 2–79 as a biocontrol agent is due to the phenazine antibiotic, phenazine-1-carboxylic acid (Thomashaw and Weller (1988) *J. Bacteriol.* 170:3499–3508), one of the phenazines produced by *P. aeruginosa*. Interestingly, phenazine-1-carboxylic acid, like pyocyanin also possesses redox cycling capabilities (Turner and Messenger (1986) *Adv. Microbial Physiol.* 27:211–273) and may therefore be important for toxicity against *C. elegans*.

The interaction between *C. elegans* and bacteria is antagonistic. Since *C. elegans* uses bacteria as food, it is not surprising that some species of bacteria have evolved mechanisms to protect themselves against this predator. The results described above show that phenazines in general and pyocyanin in particular are some of the diffusible toxins used by *P. aeruginosa* against *C. elegans*. The deployment of phenazines as chemical weapons may have evolved much earlier, against other microorganisms and against protozoa such as amoeba. The antimicrobial action of pyocyanin may also help eliminate competing microorganisms in its natural environment (Hassan and Fridovich (1980) *J. Bacteriol.* 141:1556–163). The selective advantage attained from producing phenazines is so great that it is even retained at the expense of growth in some species. For example, the phenazine producing *Pseudomonas phenazinium* forms smaller colonies and lower maximum cell densities (but does not have a lower growth rate) compared to its non-producing mutants. In addition, non-producing mutants have greater survival than their producing parent in nutrient-limiting milieu. Yet, when grown together, the producing parents out-compete the non-producing mutants (Messenger and Turner (1981) *Soc. Gen. Microbiol. Quarterly* 8:2263–264), and by extension would also out compete other non-producing competitors of other species. Using *P. aeruginosa* strains that produce pyocyanin and other phenazines, several studies showed that amoebas that have engulfed these bacteria either encyst or die. In some cases, the phenazine bacteria are not eaten (Singh (1945) Br. J Expt. Pathol. 26:316–325; Groscop and Brent (1964) Can. J. Microbiol. 10:579–584). From the results described herein, the requirement of phenazines for nematicidal effects also suggests that phenazine production by P. fluorescens and P. aeruginosa may aid in survival against bacteria-feeding nematodes. It is possible that a secondary metabolite, which was first invented for survival against simple eukaryotes, has subsequently been coopted over the course of evolution to protect P. aeruginosa from bacteria-feeding nematodes such as C. elegans and from phagocytes during mammalian infections. Indeed, the pyocyanin defective mutants, 49H2, 34B12 and 3E8 are also attenuated in pathogenicity in a mouse burn infection model.

Materials and Methods

Strains and Plasmids. The bacterial strains and plasmids used are listed Table VII.

TABLE VII

| Strain or plasmid | Relevant characteristics | Source or reference |
| --- | --- | --- |
| *Pseudomonas aeruginosa* | | |
| PA14 | Rif$^r$ wild-type | Rahme et al., 1995 |
| PAO1-R | Wild-type | Rahme et al., 1995 |
| PAO1-G | Wild-type | J. Goldberg |
| PAO1-V | Wild-type | M. Preston |
| PAO1-I | Wild-type | M. Preston |
| PAO1-J | Wild-type | K. Jaeger |
| PAK | Wild-type | S. Lory |
| PA29 | Wild-type | Rahme et al., 1995 |
| PO37 | Wild-type | Stevens et al., 1994 |
| PA14toxA | Gm$^r$ toxA insertional mutant of PA14 | Rahme et al., 1995 |
| PA14plcS | Gm$^r$ plcS insertional mutant of PA14 | Rahme et al., 1995 |
| PA14gacA | Gm$^r$ gacA insertional mutant of PA14 | Rahme et al., 1995 |
| PA14depP | Gm$^r$ degP insertional mutant of PA14 | This study |
| PA14algDΔ4 | algD in-frame deletion mutant of PA14 | This study |
| PA14degPalgDΔ4 | algD in-frame deletion and degP insertional double mutant of PA14 | This study |
| PA14phnAphnB | Km$^r$, anthranilate synthase mutant of PA14 | L. Rahme |
| *P. fluorescens* | | |
| 2-79 (NRRL B15132) | Phz$^+$ wild-type | E. Schott |
| 55 | wild-type | E. Schott |
| WCS365 | wild-type | G. O'Toole |
| *P. syringae* pv. *maculicola* ES4326 | Sm$^r$ wild-type | Davis et al., 1991 |

Nematode Strains and Culture Conditions. Strains were maintained and handled on NG agar with E. coli OP50 as food source (Sulston and Hodgkin (1988) Methods. In The nematode Caenorhabditis elegans, Wood ed. (Cold Spring Harbor, N.Y.: Cold Spring Harbor Laboratory), pp. 587–606; Lewis and Fleming (1995) Basic culture methods. In Caenorhabditis elegans: Modem Biological Analysis of an Organism, Vol. 48, Epstein and Shakes, eds. (San Diego, Calif.: Academic Press), pp. 4–31). Genetic nomenclature follows guidelines described by Horvitz et al. (Mol. Gen. Genet. 175:129–133, 1979). Bristol nematode strains used herein include the wild-type strain N2 (Brenner (1974) Genetics 77:71–94) and the following strains: TJ1052, age-1(hx546)II; TK22, mev-1(kn1)III; PH13, rad-8(mn163)I. These strains were provided by the Caenorhabditis Genetics Center.

Media and antibiotics. Complete media for bacteria culture and maintenance were Luria broth (LB) and King's broth (KB) (King et al. (1954) J. Lab. Clin. Med. 44:301–307; Miller, 1972, Experiments in Molecular Genetics (Cold Spring Harbor, N.Y.: Cold Spring Harbor Laboratory)), and minimal medium was M9 (Miller (1972) Experiments in Molecular Genetics (Cold Spring Harbor, N.Y.: Cold Spring Harbor Laboratory)). Pseudomonas isolation agar (PIA) was obtained from Difco. The NGM media is described in Sulston and Hodgkin (1988, Methods. In The nematode Caenorhabditis elegans, Wood, ed. (Cold Spring Harbor, N.Y.: Cold Spring Harbor Laboratory), pp. 587–606). Peptone-sorbitol (PGS), unless noted otherwise was the media used for fast killing; it consisted of 1% Bacto Peptone (Difco), 1% NaCl, 1% glucose, 0.15 M sorbitol (Fischer Scientific) and 1.7% Bacto Agar (Difco). Antibiotics concentrations used for P. aeruginosa PA14, rifampicin at 100 μg/ml, neomycin at 200 μg/ml, and carbenicillin at 300 μg/ml.

Nematode Killing Assay. Worm killing by P. aeruginosa was performed in a plate assay. For the fast killing assay, 5 μl of an overnight King's B (King et al. (1954) J. Lab. Clin. Med. 44:301–307) culture of PA14, or the test strains, were spread on 3.5 cm diameter plates containing PGS or PG agar. A bacterial lawn of about 2 cm diameter grew in the center of plate after incubation at 37° C. for 24 hours. After cooling to room temperature (ranges from 4–12 hours after removal from 37° C. incubator), 40 worms were added to the agar. Unless otherwise stated all worm strains were cultured at 20 C, and the fourth larval (L4) stage was used. The experiments were performed in 3–4 replicates per strain. Bristol N2 was used as the wild-type strain and E. coli OP50 for the negative control. Plates seeded with worms were incubated in 25° C. Worm mortality was scored at various time points. A worm was considered dead when no movement was detectable when touched lightly with an eye-lash pick. Slow killing assays were performed generally as described above.

Factors Affecting Killing

A. Effect of osmolarity. Overnight cultures of PA14 were plated on agar plates containing Peptone-glucose (PG) media or high osmolarity PG media containing additional 0.1 M and 0.15 M of sorbitol (Fisher).

B. Effect of iron. For the iron limiting condition, 400 μM of EDDA (Ankenbauer et al. (1986) J. Bacteriol. 167:7–11) was added to PGS to chelate whatever free iron was still available, whereas in the iron-replete condition 100 μM of FeCl3 (Meyer et al. (1996) Infect. Immun. 64:518–523) was added as an iron supplement. These were tested against a PGS control.

C. Effect of growth temperature. Overnight cultures of PA14 were plated on PGS agar and grown for 36 hours at 20° C., 25° C., 30° C. and 37° C. All plates were left at 25° C. after being seeded with worms.

D. Effect of carbon source. PGS contains 1% glucose (v/v). Only the glusoce component of the media was replaced by glycerol at 1% (v/v) to form peptone-glycerol-sorbitol agar (PYS).

Screen for PA14::TnphoA mutants defective in fast killing. Two independent PA14::TnphoA mutant libraries were generated using the broad host range carbenicillin resistant (Cb$^r$) suicide vector pRT733 (Taylor (1989) J. Bacteriol. 171:1870–1878) carrying TnphoA (which confers neomycin resistance, Nm$^r$) in E. coli strain SM101pir. This strain was used to mobilize TnphoA into PA14. Conjugation was carried out on King's B media (King et al. (1954) J. Lab. Clin. Med. 44:301–307) which yielded higher frequencies of transconjugants than LB media. To test candidate mutants, conditions similar to the fast killing assay were used, with the following exceptions. Individual clones of PA14::TnphoA mutants were plated and, on each, 5 L4 worms were added. Wild-type PA14 was used as positive control. Mutants that still contained 3–5 surviving worms after 24 hours were defined as putative attenuated mutants and subjected to the fast killing assay described above. Mutant strains that consistently gave significantly lower rates of killing relative to the wild-type parent PA14 were chosen for further characterization.

Use of the Nematode Fast Killing Assay

The nematode fast killing assay, like the slow killing assay, is useful for identifying disease-causing microbial virulence factors. In addition, the assay is useful for identifying therapeutics that are capable of either inhibiting pathogenicity or increasing an organism's resistance capabilities to a pathogen. In preferred embodiments, the fast killing assay is carried out using a nematode strain having increased permeability to a compound, e.g., a toxin such as colchicine. Examples of nematodes having such increased permeability include, without limitation, animals having a mutation in a P-glycoprotein, e.g., PGP-1, PGP-3, or MRP-1. Such mutant nematodes are useful in the fast killing assay because of their increased sensitivity to toxins that is due to increased membrane permeability. This characteristic results in an assay with an increased differential between full susceptibility and full resistance to toxic compounds.

In one working example, an F2 mutagenesis screen was used to identify mutations in C. elegans genes that confer resistance to fast killing. Six mutants were identified by screening approximately 5000 haploid genomes. These mutants are useful not only for providing information about the mechanism of fast killing, but also for providing information about C. elegans immunity.

Other Hosts for Identifying Pathogenic Virulence Factors

Galleria mellonella (Greater Wax Moth)

We have discovered that the larvae of Galleria mellonella (greater wax moth) are also useful for identifying pathogenic virulence factors of the exemplary organisms, Pseudomonas aeruginosa and Fusarium oxysporum, either alone or in combination, with any of the above-described screening assays.

Pseudomonas aeruginosa

To determine the pathogenicity of Pseudomonas aeruginosa on Galleria mellonella, bacteria were injected into G. mellonella larvae as follows. Cultures of P. aeruginosa were grown overnight in King's B medium (King et al. (1954) J. Lab. Clin. Med. 44:301–307). This culture was then diluted 1:100 in the same medium and cultured. After two hours of growth, the cultures were harvested by centrifugation, and the cells were resuspended in an equal volume of 10 mM $MgSO_4$. Each culture was subsequently diluted to an $OD_{600}$ of 0.1 (approximately $10^8$ cells/ml). Using a Hamilton syringe, five microliter volumes of serial 10-fold dilutions ($10^0$ to $10^{-6}$) were injected into one of the abdominal parapodia of G. mellonella (Lysenko (1963) Journal of Insect Pathology, 5:78–82). Bacterial counts were determined by plating according to standard methods. G. mellonella larvae were purchased from Van der Horst Wholesale, St. Mary's, Ohio.

After injection of bacteria, G. mellonella larvae were placed in petri dishes and incubated at 25° C. Lethality was visually assessed after forty-eight hours by monitoring the color change (from white to black) of each larva, and by determining larval motility. Each single non-motile black larva was scored as dead. Those larvae which were still alive after forty-eight hours generally did not die even if the time of the assay was increased.

In order to determine the $LD_{50}$, ten larvae were injected using a serial dilution of bacteria. Larval death was determined, and the data were plotted on a graph (percentage of larvae killed versus number of bacteria injected). A curve of the form: percentage killed=A+(1−A)/(1+exp(B−G×log (number of bacteria))) was fitted to the data using the Systat Ver. 5.2 computer program, where A is the fraction of larvae dying with a control injection and B and G are parameters varied to fit the curve (Systat Version 5.2 for Macintosh computer, Systat Inc., 1992, Evanston, Ill.). Using this program, B and G were determined using a computer calculated induced best fit, and then the $LD_{50}$ was calculated using the following equation: $LD_{50}=\exp(B/G) \times (1-2\times A)^{(1/G)}$.

We have injected mutant P. aeruginosa (which were isolated using the above-described plant and nematode screens, or which were constructed using previously cloned genes) into larvae of G. mellonella and have calculated the $LD_{50}$ values. The results of these experiments are presented in Table VIII (below), which shows a comparison of the $LD_{50}$ values in G. mellonella and the percent killing of mice at two different concentrations of bacteria.

TABLE VIII $LD_{50}$ of P. aeruingosa strains in G. mellonella

| PA14 strain | $LD_{50}$ in G. mellonella | % Mouse Mortality at Indicated Dose | | Origin of Mutant |
|---|---|---|---|---|
| | | $5 \times 10^3$ | $5 \times 10^5$ | |
| PA14 | 1 | 53 | 100 | Wild Type |
| 41A5 | 1 | $NT^1$ | 100 | C. elegans |
| 41C1 | 1 | NT | 85 | C. elegans |
| 35A9 | 1 | NT | 55 | C. elegans |
| 16G12 | 2 | 20 | 100 | Plant screen |
| 34H4 | 2 | 0 | 33 | Plant screen |
| toxA | 2 | 40 | NT | Constructed |
| 34B12 | 3 | 0 | 56 | Plant screen |
| LasR | 4 | NT | 50 | C. elegans |
| 49H2 | 8 | NT | 50 | C. elegans |
| 3E8 | 10 | NT | 6 | C. elegans |
| 25A12 | 10 | 11 | 87 | Plant screen |
| degP | 10 | 0 | 63 | Constructed |
| 35H7 | 10 | NT | NT | C. elegans |
| 36A4 | 20 | NT | NT | C. elegans |
| 1D7 (gacA) | 20 | 0 | 50 | Plant screen |
| 23A2 | 30 | NT | NT | C. elegans |
| 33A9 | 40 | 0 | 0 | Plant screen |
| 13C9 | 80 | NT | NT | C. elegans |
| gacA | 100 | 0 | 50 | Constructed |
| 44B1 | 500 | NT | 70 | C. elegans |
| 50E12 | 600 | NT | NT | C. elegans |
| 33C7 | 2000 | 0 | 0 | Plant screen |
| 25F1 | 2,000 | 0 | 20 | Plant screen |
| dsbA | 6,000 | 0 | 62 | Plant screen |
| pho23 | 50,000 | 0 | 10 | Plant screen |

[1]NT = not tested

The results presented in Table VIII revealed that there was a significant correlation between an increased $LD_{50}$ in G. mellonella and reduced killing in the mouse model system.

The statistical correlation that was observed between virulence of P. aeruginosa in G. mellonella and mice indicates that mammalian virulence determinants can be identified by screening for bacterial isolates which have a reduced $LD_{50}$ in G. mellonella. Such a screen can be expanded from P. aeruginosa to include other pathogens which are virulent in both insects and mammals. Two possible candidates are bacteria in the genera Serratia and Proteus which are, not only an important cause of nosocomial infections, but are also highly pathogenic in G. mellonella (Chadwick (1967) Federation Proceedings 26:1675–1679). In the case of clinical isolates of *Serratia marcescens* there is a correlation between decreased adherence to human epithelial cells and increased $LD_{50}$ in *G. mellonella* (Chadwick et al. (1990) *Journal of Invertebrate Pathology* 55:133–134).

Like the nematode and plant screening systems described above, the *G. mellonella* larval screening system can be used to identify virulence factors of *P. aeruginosa* which are required for infection in mammals. In one working example, mutant isolates of *P. aeruginosa* with reduced virulence in *G. mellonella* are identified using the above-described injection method. A library of mutant bacteria having reduced virulence are generated according to standard methods, and cultures of mutant isolates are then diluted to the point where there are 100 to 1000 bacteria in five microliters. This volume is then injected into *G. mellonella* larvae. If a particular mutant isolate fails to kill *G. mellonella* at this concentration, additional injections are performed to determine the $LD_{50}$ of the mutant strain in *G. mellonella*. Bacterial isolates having reduced virulence in the insect model system are taken as candidates for further studies to identify mammalian virulence factors of *P. aeruginosa*.

The wax moth screening system can also be used with other pathogens which infect both insects and mammals. For example, an $LD_{50}$ for the wild-type form of a particular pathogen is determined in *G. mellonella*, and then mutagenized isolates of the pathogen are injected at a concentration significantly higher than the $LD_{50}$ of the wild-type isolate. Mutants which fail to kill at the higher dose are candidates for the identification of pathogen virulence factors.

Fusarium oxysporum

The success in using larvae of *Galleria mellonella* as a model for *Pseudomonas aeruginosa* infection prompted us to also test the infectivity of the fungus, *Fusarium oxysporum*, in this system.

Pathogenicity of *Fusarium oxysporum* on *Galleria mellonella* was determined as follows. A single *F. oxysporum* spore was used to start a culture of *F. oxysporum* on a plate of potato dextrose agar (Difco) according to standard methods. The surface of the plate was washed with 2 ml of Armstrong Fusarium Medium (Armstrong and Armstrong (1948) Phytopathology 38: 808–826, and these 2 ml were added to a small flask with an additional 25 ml of the same medium. After two days at room temperature, a turbid spore culture of *F. oxysporum* developed and was used for injection experiments. Samples of this spore culture were pelleted in a microcentrifuge, and the spores were subsequently resuspended in 10 mM $MgSO_4$ with 5 mg/ml carbenicillin. Carbenicillin was included so that the *G. mellonella* larvae would not die from bacterial infections prior to succumbing to *F. oxysporum*. Ten-fold serial dilutions of the spore cultures were made with the same medium, and five-microliter samples of the dilutions ($10^0$, $10^{-1}$, $10^{-2}$, and $10^{-3}$) were injected into larvae of *G. mellonella* using a Hamilton syringe. The number of spores in each dilution were determined according to standard methods, for example, by plating an aliquot of the dilution series on Armstrong Fusarium Medium and counting the number of which germinated spores. As a control, 10 mM $MgSO_4$ with 5 mg/ml carbenicillin was also injected into an additional set of larvae. Injected larvae were placed in petri dishes (10 per dish). After seven days at 25 C, the deceased larvae were tallied. Dead larvae became black in color and frequently had a fuzzy white coating of fungus.

The $LD_{50}$ for *F. oxysporum* in *G. mellonella* was calculated by fitting a curve of the larval killing data to the equation which is described above using the Systat program. The results from two independent injection experiments are shown below in Table IX and a representative killing curve is shown in FIG. 19. The Systat computer program was used to fit a curve to the data points as described above (where b=4.51, g=1.11), and the LD50 for *F. oxysporum*. in *G. mellonella* was calculated to be 60 spores.

TABLE IX

| Number of Spores Injected | Larvae Killed (Out of 20) |
| --- | --- |
| 1700 | 20 (100%) |
| 170 | 13 (65%) |
| 17 | 2 (10%) |
| 1.7 | 1 (5%) |
| 0 | 0 (0%) |
| 1800 | 20 (100%) |
| 180 | 18 (90%) |
| 18 | 6 (30%) |
| 1.8 | 2 (10%) |
| 0 | 0 (0%) |

The $LD_{50}$ (approximately 60 spores) of *F. oxysporum* in *G. mellonella* that was determined in these experiments indicated that this system was useful in screens designed to identify *F. oxysporum* virulence factors. In one working example, *F. oxysporum* is mutagenized by restriction enzyme mediated integration (REMI) according to standard methods (Kuspa and Loomis (1994) *Genetics* 138: 665–674; Tang et al. (1992) *Mol. Microbiol.* 6: 1663–1671, 1992; Lu, *Proc. Natl. Acad. Sci.*, USA 91: 12649–12653, 1994; and Bolker (1995) *Mol. Gen. Genet.* 248: 547–552). A library of fungi mutagenized in this manner are then screened for reduced virulence by injection into *G. mellonella* larvae, and fungal genes that affect virulence are identified according to standard methods, for example, by inverse PCR using the inserted DNA and subsequent sequencing of the adjacent fungal DNA. *F. oxysporum* with reduced virulence in *G. mellonella* is then tested for reduced virulence in plants and higher animals, and common virulence factors are identified. The use of *G. mellonella* as a screening system permits the relatively rapid and inexpensive identification of important fungal virulence factors.

Cyptococcus

Cryptococcal virulence was also tested using the wax moth caterpillar assay as follows. Caterpillars were wound-inoculated using a sterilized syringe loaded with a five or ten µl suspension of yeast cells in saline containing 120 µg/ml tetracycline to prevent concomittant bacterial superinfection. The concentration of yeast cell bodies was estimated by visual inspection with a hemacytometer. The actual colony-forming units present in one syringe volume was later determined by the serial dilution of the syringe contents, and culture on YPD agar plates. The syringe was inserted into the last proleg of the caterpillar, and the yeast cells were injected into the haemocoel. The wound-inoculated caterpillars were then placed in a sterile container, incubated at 37° C., and assayed twice daily for viability. Wounded caterpillars began to die four days after inoculation with Cryptococcus. Caterpillar mortality is expressed as the dose of fungal cells that resulted in the death of fifty percent of inoculated caterpillars at six days ($LD_{50}$). In this experiment, the $LD_{50}$ of caterpillars inoculated with Cryptococcus H99 was 200 cells. No lethality was observed in caterpillars inoculated with either saline or 100,000 cfu of heat-killed Cryptococcal cells.

We next tested Cryptococcal mutant strains ade2 (adenine auxotroph) and gpa1 (G protein alpha), which were known to have reduced virulence in mice, for virulence in *Galleria*

*mellonella*. We found that Cryptococcus H99 had an $LD_{50}$ of 130 yeast cell (95% confidence interval is 63 to 290). We found that ade2 and gpa1 were attenuated for virulence in *G. mellonella* with $LD_{50}$s of 630 yeast cells, and 42,000 yeast cells, respectively. Expression of the wild-type GPA1 gene in the mutant gpa1 strain restored its virulence; the $LD_{50}$ of the reconstructed strain was 3,200 yeast cells (FIG. 20). We also tested Cryptococcus containing mutations in ras (RAS), pka (protein kinase A), and cna1 (calcineurin), which were known to have reduced virulence in mice, and found they also had reduced virulence in *G. mellonella*.

Advantages of the *G. mellonella* Screening System

The use of *G. mellonella* is advantageous as a host system for identifying mammalian virulence factors of *P. aeruginosa*, *F. oxysporum*, and other pathogens. As noted above, one important advantage provided by this system is that mutant pathogen isolates can be rapidly and inexpensively screened. In various experiments, up to 250 *G. mellonella* have been injected per hour with samples of *P. aeruginosa*. This rapid throughput makes it possible to assay large numbers of mutant pathogens in a relatively short amount of time. In addition, it is possible with *G. mellonella* to determine an $LD_{50}$ for a pathogen. Such a determination facilitates an assessment of the relative virulence of different pathogenic isolates. In yet another advantage, the killing of mice by *P. aeruginosa* shows a better correlation to virulence in *G. mellonella* than other model organisms that have been used. Accordingly, a screen for pathogen mutants using this system is highly likely to identify mammalian (e.g., human) virulence determinants. Finally, the use of *G. mellonella* is likely to identify virulence factors not found in other multi-host screens.

*Plutella xylostella* (Diamondback Moth)

We have also discovered that the larvae of *Plutella xylostella* (diamondback moth) are useful for identifying pathogenic virulence factors of *Pseudomonas aeruginosa*.

The pathogenicity of *P. aeruginosa* on *Plutella xylostella* was determined using a larval mustard green feeding assay. Larvae of *Plutella xylostella* were fed mustard leaves infiltrated with *Pseudomonas aeruginosa* as follows. *P. aeruginosa* was cultured in King's B medium (King et al. (1954) *J. Lab. Clin. Med.* 44:301–307). Overnight cultures were pelleted in a microcentrifuge and were then washed twice in 10 mM $MgSO_4$. Cells were then resuspended in 10 mM $MgSO_4$ and were diluted to an $OD_{600}$ of 0.1. *Pl. xylostella* larvae were maintained on a semisynthetic wheat germ based diet according to standard methods (Shelton et al. (1991) *J. Ent. Sci.*, 26:17–26).

Mustard greens (from Cambridge Natural Foods, Cambridge, Mass.) were cut into pieces of about 10 cm² and were submersed in 10 mM $MgSO_4$ containing *P. aeruginosa*. The submersed leaves were placed under vacuum, and the vacuum was released suddenly to infiltrate the bacterial solution into the leaves. As a control, leaves were also infiltrated with only 10 mM $MgSO_4$. Infiltrated leaf material was incubated at 23° C. in a petri dish with twenty *Pl. xylostella* larvae, which Were allowed to feed at will. Deceased larvae were scored after forty-eight hours. Larvae which did not move after being touched with a pipette tip were scored as dead.

Wild-type *P. aeruginosa* strains PA14 and PA01 caused mortality nearing one-hundred percent killing of *Pl. xylostella* larvae. Three mutant isolates of PA14, however, showed greatly reduced killing. These results indicated that (1) *P. aeruginosa* was lethal after being ingested by insect larvae and (2) mutant isolates of *P. aeruginosa* strain PA14 had reduced virulence in this model system. A summary of these results is presented in Table X (below).

TABLE X

| Strain | N | Number of larvae dead at 48 hours |
|---|---|---|
| PA14 | 80 | 79 (99%) |
| PAO1 | 80 | 76 (95%) |
| PA14 dsbA | 40 | 10 (25%) |
| PA14pho23 | 40 | 3 (8%) |
| PA14 lasR | 40 | 8 (20%) |
| $MgSO_4$ control | 80 | 2 (3%) |

*Drosophila melanogaster* (Fruit Fly)

In yet another example, we have found that the fruit fly, *Drosophila melanogaster*, is useful for evaluating pathogenesis of *Pseudomonas aeruginosa*.

The pathogenicity of *P. aeruginosa* on *Drosophila melanogaster* was determined using the following abdomen pricking assay. Fly stocks of OregonR or the marked strain yellow white (yw) were cultured under standard conditions on corn meal medium. Two different genetic backgrounds were tested since it has been demonstrated that some strains are more susceptible to bacterial challenge (Lemaitre et al. (1996) *Cell* 86: 973–983). Cultures of *P. aeruginosa* strain, PA14, and the control, *E. coli* DH5α, were grown overnight in King's B medium (King et al. (1954) *J. Lab Clin. Med.* 44:301–307). Following overnight culturing, the cells were diluted 1/10 and grown for an additional four to five hours. The cells were subsequently washed twice, resuspended in distilled water, and then used for abdomen pricking at the following four concentrations: undiluted, diluted 1/10, concentrated 10-fold, and concentrated 100-fold.

Bacterial challenge was conducted by pricking the abdomens of anaesthetized adult flys with a fine needle which was dipped in the different concentrations of PA14 or DH5α. Following bacterial challenge, flies were placed at 28° C. and monitored for death as assayed by a lack of movement. Eighteen to twenty flies were assayed at each concentration of bacteria, and the mean and standard deviations of fly death were calculated. We found that PA14 effectively killed *D. melanogaster* adults in a dose-dependent manner. Little killing was observed in experiments with the control DH5α strain. The results of these experiments using the OrR strain are summarized in FIG. 21. Similar results were observed in the yw genetic background.

As discussed above, *P. aeruginosa* was found to effectively kill *Drosophila melanogaster* in an assay involving the introduction of *P. aeruginosa* into the abdomen of adult flies using a simple needle prick. Other methods for introducing measured amounts of *P. aeruginosa* include, without limitation, direct injection and ingestion (e.g., by adding *P. aeruginosa* to the fly growth medium). If desired, larval flies may be used in pathogenesis experiments.

One advantage of using *D. melanogaster* is that the multiple molecular and genetic approaches facilitated by this model organism can used to study bacterial pathogenesis. *D. melanogaster* is an excellent model for studying the innate immune response, and many of the genes involved in this response have been cloned from this insect (Hoffmann (1995) *Curr. Biol.* 7:4–10). Mutations in these genes may be used in conjunction with mutations in bacterial virulence factors isolated from screens involving the various hosts of *P. aeruginosa* to provide valuable information about the mode of action of these virulence factors.

Screening Systems for Identifying Therapeutics or Plant Protectants

As discussed above, our experimental results demonstrate that a set of *P. aeruginosa* virulence factors are involved in pathogenicity in three diverse hosts and that these common virulence determinants define fundamental features of bacterial pathogenicity which are host independent. Based on this discovery we have developed a screening procedure for identifying therapeutic compounds (e.g., anti-pathogenicity pharmaceuticals) which can be used to inhibit pathogens capable of independently infecting either an animal (e.g., a human patient) or a plant (e.g., a commercial crop plant). In general, the method involves screening any number of compounds for therapeutically- or agriculturally-active agents by employing the multi-host animal/plant pathogen (e.g., *P. aeruginosa* UCBPP-PA14) system(s) described herein. Based on our demonstration that there are common virulence factors for pathogenicity in plants, mice, and nematodes, it will be readily understood that a compound which interferes with the function of such a virulence factor in a nematode also provides an effective therapeutic agent in a mammal (e.g., a human patient) or a plant. Whereas most antibiotics currently in use in medicine or agriculture are either bactericidal or bacteriostatic, thus favoring strains or mutants resistant to them, the compounds identified in the screening procedures described herein (e.g., the nematode system) do not kill the bacteria but instead render them non-pathogenic. Moreover, since the screening procedures of the invention are performed in vivo, it is also unlikely that the identified compounds will be highly toxic to a eukaryotic host organism.

Accordingly, the methods of the invention simplify the evaluation, identification, and development of active agents such as drugs and plant protectants for the treatment of pathogenic diseases, including diseases caused by bacteria, fungi, viruses, annelids, nematodes, platyhelminthes, and protozoans. In general, the screening methods of the invention provide a facile means for selecting natural product extracts or compounds of interest from a large population which are further evaluated and condensed to a few active and selective materials. Constituents of this pool are then purified and evaluated in the methods of the invention to determine their anti-pathogenic activity.

Below we describe screening methods for evaluating the efficacy of a compound as an anti-pathogenic agent. These examples are intended to illustrate, not limit, the scope of the claimed invention.

Test Extracts and Compounds

In general, novel anti-pathogenic drugs or plant protectants are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to have anti-pathogenic activity, further fractionation of the positive lead extract is necessary to isolate chemical constituents responsible for the observed effect. Thus, the goal of the extraction, fractionation, and purification process is the careful characterization and identification of a chemical entity within the crude extract having anti-pathogenic activity. Methods of fractionation and purification of such heterogenous extracts are known in the art. If desired, compounds shown to be useful agents for the treatment of pathogenicity are chemically modified according to methods known in the art.

There now follow examples of high-throughput systems useful for evaluating the efficacy of a molecule or compound in promoting resistance to a pathogen or inhibiting a pathogen. These examples are provided to illustrate, not limit, the invention.

Nematode Bioassay System

To enable mass screening of large quantities of natural products, extracts, or compounds in an efficient and systematic fashion, *Caenorhabditis elegans* L4 hermaphrodite larvae are cultured in wells of a microtiter plate, facilitating the semiautomation of manipulations and full automation of data collection. As is discussed above, we have discovered that *P. aeruginosa* UCBPP-PA14 infects and kills *C. elegans*, whereas *P. aeruginosa* UCBPP-PA14 carrying a mutagenized virulence gene is non-pathogenic. If a pathogen has diminished, pathogenicity then L4 worms live, develop into adult hermaphrodites, and produce thousands of live progeny. Accordingly, if *C. elegans* is incubated with the pathogen, the worms will die, unless a compound is present to reduce *P. aeruginosa* pathogenicity. The presence of such live progeny is easily detected using a variety of methods, including visual screening with standard microscopes.

To evaluate the ability of a test compound or extract to promote a host's resistance to a pathogen or to repress pathogenicity of a pathogen, a test compound or extract is inoculated at an appropriate dosage into NGM agar seeded with an appropriate amount of an overnight culture of a pathogen, e.g., *P. aeruginosa* UCBPP-PA14. If desired, various concentrations of the test compound or extract can be inoculated to assess dosage effect on both the host and the pathogen. Control wells are inoculated with non-pathogenic bacteria (negative control) or a pathogen in the absence of a test compound or extract (positive control). Plates are then incubated 24 hours at 37° C. to facilitate the growth of the pathogen. Microtiter dishes are subsequently cooled to 25° C., and two *C. elegans* L4 hermaphrodite larva are added to the plate and incubated at 25° C., the upper limit for normal physiological integrity of *C. elegans*. At an appropriate time interval, e.g., 4 to 5 days, wells are examined for surviving progeny, e.g., by monitoring motion of worms using a motion detector.

Comparative studies between treated and control larvae are used to determine the relative efficacy of the test molecule or compound in promoting the host's resistance to the pathogen or inhibiting the virulence of the pathogen. A test compound which effectively stimulates, boosts, enhances, increases, or promotes the host's resistance to the pathogen or which inhibits, inactivates, suppresses, represses, or controls pathogenicity of the pathogen and does not adversely affect the normal physiology, reproduction, or development of the worms is considered useful in the invention.

Plant Bioassay System

To enable mass screening of large quantities of natural products, extracts, or compounds in an efficient and systematic fashion, host plants (e.g., seeds, seedlings, plantlets, embryos, mature plants, or leaves) are cultured in wells of a microtiter plate or any other suitable container, facilitating the semiautomation of manipulations and full automation of data collection. Particular examples of suitable plant hosts useful in this bioassay include, without limitation, petunia, tomato, potato, tobacco, Arabidopsis, soybean, corn, wheat, rye, rice, barley, or any other plant of commercial or agricultural significance. Methods for culturing plants are known in the art (see, e.g., Vasil, I. K., *Cell Culture and Somatic Cell Genetics of Plants* Vol I, II, III, Laboratory Procedures and Their Applications, Academic Press, New York, 1984; Dixon R. A., *Plant Cell Culture—A Practical Approach*, IRL Press, Oxford University, 1985). As is discussed above, we have discovered that *P. aeruginosa* UCBPP-PA14 infects and kills *Arabidopsis thaliana*, whereas *P. aeruginosa* UCBPP-PA14 carrying a mutagenized virulence gene is non-pathogenic. Accordingly, if a pathogen has diminished pathogenicity, the plant will not develop symptoms or, alternatively, will develop attenuated symptoms relative to control plants. If *Arabidopsis thaliana* plants are incubated with the pathogen, the plants will die or have a variety of disease symptoms (e.g., chlorosis or soft-rot), unless a compound is present to reduce *P. aeruginosa* pathogenicity. The presence of such live seedlings and their associated disease symptoms is easily detected using a variety of methods, including visual screening.

To evaluate the ability of a test compound or extract to promote a host's (e.g., *Arabidopsis thaliana*) resistance to a pathogen or to repress pathogenicity of a pathogen, a test compound or extract is inoculated at an appropriate dosage into a tissue culture media (e.g., a solidified agar-based medium). In addition, if desired, the host plant can be pretreated with the candidate plant protects or anti-pathogen compound by any conventional means, e.g., a seedling or plantlet can be sprayed with a solution containing the test compound. Host plants are assayed using any standard pathogenesis screening system, e.g., the Arabidopsis and lettuce leaf infiltration assays described above, or by standard vacuum infiltration techniques. For example, host seedlings are vacuum infiltrated with the pathogen according to standard methods. After vacuum infiltration seedlings are cultured according to methods known in the art (e.g., methods for culturing Arabidopsis are found in *Methods in Arabidopsis Research*, Koncz, C., Chua, N.-H., Schell, J., eds., World Scientific Publishing Co. Pte. Ltd., Singapore, 1992). If desired, various concentrations of the test compound or extract can be inoculated to assess dosage effect on both the host and the pathogen. Control seedlings are infiltrated with non-pathogenic bacteria (negative control) or a pathogen in the absence of a test compound or extract (positive control). At an appropriate time interval, e.g., 3 to 5 days, seedlings are examined for disease symptoms. Comparative studies between treated and control seedlings are used to determine the relative efficacy of the test molecule or compound in promoting the host's resistance to the pathogen or inhibiting the virulence of the pathogen. A test compound which effectively stimulates, boosts, enhances, increases, or promotes the host's resistance to the pathogen or which inhibits, inactivates, suppresses, represses, or controls pathogenicity of the pathogen and does not adversely affect the normal physiology, reproduction, or development of the seedlings is considered useful in the invention.

Use

The methods of the invention provide a simple means for identifying microbial virulence factors and compounds capable of either inhibiting pathogenicity or enhancing an organism's resistance capabilities to a pathogen. Accordingly, a chemical entity discovered to have medicinal or agricultural value using the methods described herein are useful as either drugs, plant protectants, or as information for structural modification of existing anti-pathogenic compounds, e.g., by rational drug design. Such methods are useful for screening compounds having an effect on a variety of pathogens including, but not limited to, bacteria, viruses, fungi, annelids, nematodes, platyhelminthes, and protozoans. Examples of pathogenic bacteria include, without limitation, Aerobacter, Aeromonas, Acinetobacter, Agrobacterium, Bacillus, Bacteroides, Bartonella, Bortella, Brucella, Calymmatobacterium, Campylobacter, Citrobacter, Clostridium, Cornyebacterium, Enterobacter, Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio, and Yersinia.

Examples of pathogenic fungi include, without limitation, Alternaria, Aspergillus, Basidiobolus, Bipolaris, Blastoschizomyces, Candida, *Candida albicans, Candida krusei, Candida glabrata* (formerly called *Torulopsis glabrata*), *Candida parapsilosis, Candida tropicalis, Candida pseudotropicalis, Candida guilliermondii, Candida dubliniensis,* and *Candida lusitaniae,* Coccidioides, Cladophialophora, Cryptococcus, Cunninghamella, Curvularia, Exophiala, Fonsecaea, Histoplasma, Madurella, Malassezia, Plastomyces, Rhodotorula, Scedosporium, Scopulariopsis, Sporobolomyces, Tinea, and Trichosporon.

Anti-pathogenic compounds could be used to treat a variety of infections, for example, fungal infections. Fungi, including, but not limited to Candida, cause invasive diseases in hosts with altered immunity, such as patients with HIV infection, organ or bone marrow transplants, or neutropenia following cancer immunotherapy. There are approximately 200 species of the genus Candida, but nine cause the great majority of human infections. They are *C. albicans, C. krusei, C. glabrata* (formerly called *Torulopsis glabrata*), *C. parapsilosis, C. tropicalis, C. pseudotropicalis, C. guilliermondii, C. dubliniensis,* and *C. lusitaniae*. They cause infections of the mucous membranes, for example, thrush, esophagitis, and vagititis; skin, for example, intertrigo, balanitis, and generalized candidiasis; blood stream infections, for example, candidemia; and deep organ infections, for example, hepatosplenic candidiasis, urinary tract candidiasis, arthritis, endocarditis, and endophthamitis.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections which provide continuous, sustained levels of the drug in the patient. Treatment of human patients or other animals will be carried out using a therapeutically effective amount of an anti-pathogenic agent in a physiologically-acceptable carrier. Suitable carriers and their formulation are described, for example, in Remington's *Pharmaceutical Sciences* by E. W. Martin. The amount of the anti-pathogenic agent to be administered varies depending upon the manner of administration, the age and body weight of the patient, and with the type of disease and extensiveness of the disease. Generally, amounts will be in the range of those used for other agents used in the treatment of other microbial diseases, although in certain instances lower amounts will be needed because of the increased specificity of the compound. A compound is administered at a dosage that inhibits microbial proliferation. For example, for systemic administration a compound is administered typically in the range of 0.1 ng–10 g/kg body weight.

For agricultural uses, the compositions or agents identified using the methods disclosed herein may be used as chemicals applied as sprays or dusts on the foliage of plants. Typically, such agents are to be administered on the surface of the plant in advance of the pathogen in order to prevent infection. Seeds, bulbs, roots, tubers, and corms are also treated to prevent pathogenic attack after planting by controlling pathogens carried on them or existing in the soil at the planting site. Soil to be planted with vegetables, ornamentals, shrubs, or trees can also be treated with chemical fumigants for control of a variety of microbial pathogens. Treatment is preferably done several days or weeks before planting. The chemicals can be applied by either a mechanized route, e.g., a tractor or with hand applications. In addition, chemicals identified using the methods of the assay can be used as disinfectants.

All publications and patents mentioned in this specification are herein incorporated by reference to the same extent as if each individual publication or patent was specifically and individually indicated to be incorporated by reference.

From the foregoing description, one skilled in the art can easily ascertain the essential characteristics of this invention, can make various changes and modifications of the invention to adapt it to various usages and conditions. Thus, other embodiments are also within the claims.

Deposit

*Pseudomonas aeruginosa* strain UBCPP-PA14 has been deposited with the American Type Culture Collection on Mar. 22, 1995, and bears the accession number ATCC No. 55664. Applicants acknowledge their responsibility to replace this strain should it loose viability before the end of the term of a patent issued hereon, and their responsibility to notify the American Type Culture Collection of the issuance of such a patent, at which time the deposit will be made available to the public. Prior to that time the deposit will be made available to the Commissioner of Patents under terms of CFR §1.14 and 35 USC §112.

What is claimed is:

1. A method for identifying a fungal virulence factor, comprising
   (a) identifying a fungal pathogen which is capable of infecting at least two different eukaryotic organisms, said two different eukaryotic organisms being chosen from (i) an animal and a plant or (ii) a vertebrate and an invertebrate;
   (b) generating a mutant of said fungal pathogen;
   (c) exposing each of said organisms to said mutated pathogen;
   (d) determining whether said mutated fungal pathogen is capable of causing disease in each of said organisms, a reduction of disease in both of said organisms relative to that caused by said wild-type fungal pathogen indicating a mutation in said fungal virulence factor; and
   (e) using said mutation as a marker for identifying said fungal virulence factor.

2. A method for mutating a pathogenic fungal virulence factor, comprising
   (a) identifying a fungal pathogen which is capable of infecting at least two different eukaryotic organisms, said two different eukaryotic organisms being chosen from (i) an animal and a plant or (ii) a vertebrate and an invertebrate;
   (b) generating a mutant of said fungal pathogen;
   (c) exposing each of said organisms to said mutated fungal pathogen; and (d) determining whether said mutated fungal pathogen is capable of causing disease in each of said organisms, a reduction of disease in both of said organisms relative to that caused by said wild-type fungal pathogen indicating a mutation in said fungal virulence factor.

3. A method of reducing the virulence of a fungal pathogen, comprising (a) identifying a fungal pathogen which is capable of infecting at least two different eukaryotic organisms, said two different eukaryotic organisms being chosen from (i) an animal and a plant or (ii) a vertebrate and an invertebrate;

(b) generating a mutant of said fungal pathogen;

(c) exposing each of said organisms to said mutated fungal pathogen; and (d) determining whether said mutated fungal pathogen is capable of causing disease in each of said organisms, a reduction of disease in both of said organisms relative to that caused by said wild-type fungal pathogen indicating a reduction in fungal virulence.

4. The method of claim 1, 2, or 3, wherein said animal is a vertebrate.

5. The method of claim 4, wherein said vertebrate is a rodent.

6. The method of claim 1, 2, or 3, wherein said plant is a crucifer.

7. The method of claim 1, 2, or 3, wherein said animal is an invertebrate.

8. The method of claim 7, wherein said invertebrate is a nematode.

9. The method of claim 1, 2, or 3, wherein said plant is a crucifer.

10. The method of claim 1, 2, or 3, wherein said vertebrate is a rodent.

11. The method of claim 1, 2, or 3, wherein said invertebrate is a nematode.

12. The method of claim 1, 2, or 3, wherein said fungal pathogen is a yeast.

13. The method of claim 12, wherein said yeast is Cryptococcus.

* * * * *